US007709509B2

(12) United States Patent
Keil et al.

(10) Patent No.: US 7,709,509 B2
(45) Date of Patent: May 4, 2010

(54) OXADIAZOLONES AND DERIVATIVES THEREOF AS PEROXISOME PROLIFERATOR-ACTIVATED RECEPTOR (PPAR) DELTA AGONISTS

(75) Inventors: Stefanie Keil, Hofheim (DE); Wolfgang Wendler, Selters (DE); Maike Glien, Wiesbaden (DE); Jochen Goerlitzer, Frankfurt (DE); Karen Chandross, Somerset, NJ (US); Daniel G. McGarry, Branchburg, NJ (US); Jean Merrill, Whippany, NJ (US); Patrick Bernardelli, Villepreux (FR); Baptiste Ronan, Clamart (FR); Corinne Terrier, Livry Gargan (FR)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 12/133,405

(22) Filed: Jun. 5, 2008

(65) Prior Publication Data
US 2008/0255212 A1 Oct. 16, 2008

Related U.S. Application Data

(63) Continuation of application No. 11/535,266, filed on Sep. 26, 2006, now abandoned, which is a continuation of application No. PCT/EP2005/002950, filed on Mar. 19, 2005.

(30) Foreign Application Priority Data
Apr. 1, 2004 (EP) .................... 04007879

(51) Int. Cl.
*A61K 31/4245* (2006.01)
*A61K 31/422* (2006.01)
*A61K 31/427* (2006.01)
*C07D 277/20* (2006.01)
*C07D 271/07* (2006.01)
*C07D 263/30* (2006.01)

(52) U.S. Cl. ............. 514/364; 514/365; 514/374; 548/132; 548/202; 548/235

(58) Field of Classification Search .............. 514/364, 514/365, 374; 548/132, 202, 203, 235
See application file for complete search history.

(56) References Cited

U.S. PATENT DOCUMENTS

| 5,376,670 A | 12/1994 | Connor et al. | |
| 5,641,796 A * | 6/1997 | Dominianni et al. | ........ 514/374 |
| 2008/0262036 A1 * | 10/2008 | Keil et al. | ........ 514/314 |

FOREIGN PATENT DOCUMENTS

| WO | WO 96/13264 | 5/1996 |
| WO | WO 03/043997 | 5/2003 |
| WO | WO 2004/094393 | 11/2004 |
| WO | WO 2004/094394 | 11/2004 |
| WO | WO 2005/073199 | 8/2005 |

OTHER PUBLICATIONS

Dow, R. L., et. al., Benzyloxazolidine-2,4-Diones as Potent Hypoglycemic Agents, J. Med. Chem., (1991), vol. 34, No. 5, pp. 1538-1544.
Boschelli, D. H., et. al., 1,3,4-Oxadiazole, 1,3,4-Thiadiazole, and 1,2,4-Triazole Analogs of the Fenamates: In Vitro Inhibition of Cyclooxygenase and 5-Lipoxygenase Activities, J. Med. Chem. (1993), vol. 36, pp. 1802-1810.
Ellingboe, J. W., et. al., Antihyperglycemic Activity of Novel Naphthalenyl 3H-1,2,3,5-Oxathiadiazole 2-Oxides, J. Med. Chem. (1993) vol. 36, pp. 2485-2493.
Ellingboe, J. W., et. al., Antihyperglycemic Activity of Novel Substituted 3H-1,2,3,5-Oxathiadiazole 2-Oxides, J. Med. Chem., (1992), vol. 35, pp. 1176-1183.
Momose, Y., et. al., Novel 5-Subsituted 2,4-Thiazolidinedione and 2,4-Oxazolidinedione Derivatives as Insulin Sensitizers with Antidiabetic Activities, J. Med. Chem. 2002, vol. 45, pp. 1518-1534.
Mullican, M. D, et. al., Design of 5-(3,5-Di-Tert-Butyl-4-Hydroxyphenyl)-1,3,4-Thiadiazoles,-1,3,4-Oxadiazoles, and -1,2,4-Triazoles as Orally-Active, Nonuclerogenic Antiinflammatory Agents, J. Med. Chem., (1993), vol. 36, pp. 1090-1099.
Sohda, T., et. al., Studies on Antidiabetic Agents XII.1) Synthesis and Activity of the Metabolites of (+)-5-p-[p-2-(5-Ethyl-2Pyridyl)Ethoxy]Benzyl}-2,4-Thiazolidinedione (Pioglitazone), Chem. Pharm. Bull. vol. 43, No. 12, pp. 2168-2172 (1995).

(Continued)

Primary Examiner—Yong Chu
(74) Attorney, Agent, or Firm—Jiang Lin

(57) ABSTRACT

The invention relates to oxadiazolones and to their physiologically acceptable salts and physiologically functional derivatives showing peroxisome proliferator activator receptor (PPAR) delta agonist activity comprising compounds of formula I,

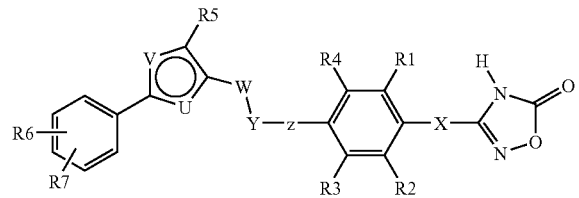

in which the R1-R7 substituents as well as the U, V, W, X Y and z radicals are as defined herein, and their physiologically acceptable salts and processes for their preparation. The compounds are suitable for the treatment and/or prevention of disorders of fatty acid metabolism and glucose utilization disorders as well as of disorders in which insulin resistance is involved; neurodegenerative diseases and/or demyelinating disorders of the central and peripheral nervous systems and/or neurological diseases involving neuro-inflammatory processes and/or other peripheral neuropathies.

32 Claims, No Drawings

OTHER PUBLICATIONS

Sohda, T., et. al., Studies on Antidiabetic Agents. 11.1 Novel Thiazolidinedione Derivatives as Potent Hypoglycemic and Hypolipidemic Agents, J. Med. Chem., (1992), vol. 35, pp. 2617-2626.

Zask, A., et. al., Synthesis and Antihyperglycemic Activity of Novel 5-(Naphthalenylsulfonyl)-2,4-Thiazolidinediones, J. Med. Chem. (1990), vol. 33, pp. 1418-1423.

* cited by examiner

OXADIAZOLONES AND DERIVATIVES THEREOF AS PEROXISOME PROLIFERATOR-ACTIVATED RECEPTOR (PPAR) DELTA AGONISTS

CROSS-REFERENCE TO RELATED APPLICATIONS

This application is a continuation of U.S. Ser. No. 11/535,266 filed on Sep. 26, 2006 which is a continuation of International Application No. PCT/EP2005/002950 filed on Mar. 19, 2005 which is incorporated herein by reference in its' entirety which also claims the benefit of priority of European Patent Application No. 04/007879.2 filed on Apr. 1, 2004.

FIELD OF THE INVENTION

The invention relates to compounds useful in the treatment of metabolic disorders and diseases affecting the central nervous system. More specifically, the present invention relates to oxadiazolones and to their physiologically acceptable salts and physiologically functional derivatives that exhibit peroxisome proliferator-activated receptor delta (PPARdelta) agonist activity.

BACKGROUND OF THE INVENTION

The peroxisome proliferator-activated receptors (PPAR) are transducer proteins belonging to the steroid/thyroid/retinoid receptor superfamily. The PPARs were originally identified as orphan receptors without known ligands, but were known for their ability to mediate the pleiotropic effects of fatty acid peroxisome proliferators. These receptors function as ligand-regulated transcription factors that control the expression of target genes by binding to their responsive DNA sequences as heterodimers with RXR. The target genes encode enzymes involved in a number of metabolic and cell growth/cell proliferation/cell differentiation inductions. These then provide targets for the development of therapeutic agents for the treatment of metabolic and central nervous system disorders, among others.

PPAR agonists are well known and have been described in the prior art, see U.S. Pat. No. 6,200,995 to De La Brouse-Elwood et. al.; WO 03/043997 to Johnston et. al. and WO 01/00603 and WO 02/092590 to Keil et. al.). Compounds comprising an oxadiazolone feature as inhibitors of factor Xa were disclosed in DE 101 12 768 A1 and oxodiazolones have also been described as oral hypoglycemic agents in WO 96/13264.

The present invention then, comprises compounds which provide therapeutic variable moderation of lipid and/or carbohydrate metabolism and are thus suitable for the prevention and/or treatment of diseases such as type-2 diabetes, atherosclerosis and the diverse disease states that are a result thereof. Another purpose of the invention is to treat neurodegenerative diseases and/or demyelinating disorders of the central and peripheral nervous systems and/or neurological diseases involving inflammation of the central nervous system and/or other peripheral neuropathies.

SUMMARY OF THE INVENTION

The present invention comprises a series of compounds which moderate the activity of peroxisome proliferators—activated receptors (PPAR) has been found. The compounds are suitable in particular for activating PPARdelta and PPA-Ralpha receptors, however the extent of the relative activation of the receptor will vary depending on the specific compound administered.

DETAILED DESCRIPTION OF THE INVENTION

Compounds of the present invention are generically described by formula I, below:

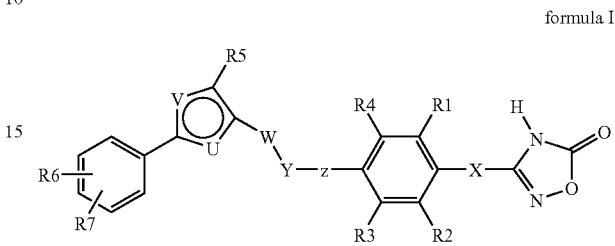

formula I wherein,

X is —$CH_2$ or a bond;

$R_1$, $R_2$, $R_3$ and $R_4$ are independently selected from the group comprising H, F, Cl, Br, —$CF_3$, ($C_1$-$C_4$)alkyl, (C0-$C_4$)alkylene-O—(C0-$C_4$)alkylene-H, $SCH_3$, $S(O)CH_3$, $S(O)_2CH_3$, CN, —$OCF_3$, —$OCHF_2$, and —$OCH_2F$;

Z is a bond or —$CH_2$;

Y is O, —S—, —S(O) or —$S(O)_2$;

W is —$CH_2$ or —$CH_2CH_2$;

one of U and V is N the other is —S— or —O—;

$R_5$ is selected from the group comprising of ($C_1$-$C_8$) alkyl, ($C_1$-$C_6$)alkylene-O—($C_0$-$C_4$) alkylene-H, ($C_0$-$C_6$)alkylene-phenyl, ($C_1$-$C_6$)alkylene-O—($C_0$-$C_4$)alkylene-phenyl, ($C_3$-$C_6$)cycloalkyl, ($C_2$-$C_8$)alkenyl, and where ($C_1$-$C_8$)alkyl or alkylene can be substituted 1-2 times by —OH or —O—($C_1$-$C_4$)alkyl;

$R_6$, $R_7$ are independently selected from the group comprising H, F, Br, —$CF_3$, —$OCF_3$, ($C_1$-$C_6$)alkyl, ($C_0$-$C_4$)alkylene-O—($C_0$-$C_4$)alkylene-H, —$SCF_3$, —$SF_5$, —$OCF_2$—$CHF_2$, —$OCHF_2$, —$OCH_2F$, O-phenyl, phenyl, $NO_2$;

as well as their physiologically acceptable salts and tautomeric forms.

Another embodiment of this invention is a compound of the formula I in which

X is a bond.

Another embodiment of this invention is a compound of the formula I wherein one or more substituents have the following meaning:

U is S and,

V is N or

U is —N— and

V is —S— or u is —O— and,

V is —N— or

U is —N— and

V is —O—;

and/or

U is —S—,

V is —N—,

Z is a bond;

and/or

U is N,

V is O,

Z is a bond,

X is a bond;

and/or

X is a bond,

Z is a bond;

and/or $R_6$ is in para position;

and/or $R_7$ is H or F, preferably H;

and/or $R_2$, $R_3$, and $R_4$ are H, and, $R_1$ is selected from the group consisting of H, F, Cl, Br, $CF_3$, $(C_1-C_4)$alkyl, $(C_0-C_4)$alkylene-O—$(C_0-C_4)$alkylene-H, —$SCH_3$, $S(O)CH_3$, $S(O)_2CH_3$, —CN;

and/or

Y is O or S, preferably O;

and/or

W is $CH_2$ and/or $R_5$ is $(C_1-C_4)$alkyl, $(C_1-C_4)$alkylene-O—$(C_0-C_4)$alkylene-H or $(C_1-C_4)$ alkylene-O—$(C_0-C_4)$alkylene-phenyl, where alkylene can be substituted by O—$(C_0-C_4)$alkylene-H.

Another embodiment of this invention is a compound of the formula I in which

X is a bond or $CH_2$, preferably a bond;

$R_1$ is selected from the group comprising H, F, Cl, Br, $CF_3$, $(C_1-C_4)$alkyl, O—$(C_1-C_4)$alkyl, $SCH_3$, $S(O)CH_3$, $S(O)_2CH_3$, CN;

$R_2$ is H or F;

$R_3$ is H, Br or O—$(C_1-C_4)$ alkyl;

$R_4$ is H;

Z is a bond or $CH_2$, preferably a bond;

Y is O, S, S(O) or S(O)2, preferably O;

W is $CH_2$ or $CH_2CH_2$, preferably $CH_2$;

U is —S— and

V is —N— or

U is —N— and

V is —S— or

U is —N— and

V is O;

$R_5$ is $(C_1-C_6)$alkyl or $(C_2-C_6)$alkenyl, wherein the $(C_1-C_6)$alkyl can be substituted 1-2 times by —OH;

$R_6$ is in para position and is $CF_3$, $SF_5$, $OCH_3$, phenyl;

R7 is H or F.

Another embodiment of this invention is a compound of the formula I in which

X is a bond;

$R_1$ is —Cl or —$CH_3$;

$R_2$, $R_3$ and $R_4$ are H;

Z is a bond;

Y is O;

W is —$CH_2$;

U is —S— and

V is N or

U is N and

V is O or

U is O and

V is N;

$R_5$ is $(C_1-C_4)$alkylene-O—$(C_1-C_4)$alkylene-H, preferably $CH_2$—O—$(C_1-C_3)$alkylene-H, or $(C_1-C_4)$alkylene-O—$(C_1-C_4)$alkylene-phenyl, where alkylene can be substituted by O—$(C_1-C_4)$alkyl, preferably methoxy or ethoxy;

$R_6$ is in para position and —$CF_3$ or —$OCH_3$;

$R_7$ is H.

Another embodiment of this invention is a compound of the formula I in which $R_1$ and $R_2$ are independently selected from the group comprising H, F, Cl, Br, —$OCH_3$, $SCH_3$, —$CF_3$, —$CH_3$, —CN, $S(O)CH_3$ and, $S(O)_2CH_3$;

X is a bond and

Z is a bond;

or

X is $CH_2$,

Z is a bond and

W is $CH_2$;

or

X is a bond and

W is $CH_2$;

$R_3$ and $R_4$ are independently selected from the group comprising H and —$OCH_3$;

$R_6$ is in the para position and is H, F, $CF_3$, $CH_3$, $SF_5$, $OCH_3$ and phenyl;

$R_7$ is H.

Another embodiment of this invention is a compound of the formula I in which

X is a bond;

$R_1$ is $OCH_3$ or F;

$R_2$, $R_3$ and $R_4$ are H;

Z is a bond;

Y is O or S;

W is —$CH_2$ or —$CH_2CH_2$;

U is S and

V is N or

U is N and

V is S or

U is O and

V is N or

U is N and

V is O;

$R_5$ is selected from the group comprising $(C_1-C_4)$alkyl, $(C_1-C_4)$alkylene-O—$(C_1-C_4)$alkylene-H or $(C_1-C_4)$alkylene-O—$(C_1-C_4)$alkylene-phenyl, where alkylene can be substituted by O—$(C_1-C_4)$alkyl;

$R_6$ is in para position and is CF3 or OCH3;

$R_7$ is H.

Another embodiment of this invention is a compound of the formula I in which

X is a bond or $CH_2$;

$R_1$ is selected from the group comprising H, F, Cl, Br, —$OCH_3$, $SCH_3$, $CF_3$, $CH_3$, CN, $S(O)CH_3$, $S(O)_2CH_3$;

$R_2$ is H, F;

$R_3$ is selected from the group comprising H, $OCH_3$, Br;

$R_4$ is H;

Z is a bond or $CH_2$;

Y is selected from the group comprising O, S, S(O) or $S(O)_2$;

W is —$CH_2$ or —$CH_2CH_2$;

U is S and

V is N or

U is N and

V is S;

$R_5$ is selected from the group comprising $(C_1-C_4)$alkyl or $(C_2-C_4)$alkenyl, where $(C_1-C_4)$alkyl can be substituted 1-2 times by —OH, e.g. —$CH_2CH_2CH(OH)CH_2OH$ or $CH_2CH_2CH_2CH_2OH$ or $R_5$ is selected from the group comprising $(C_1-C_4)$alkylene-O—$(C_1-C_4)$alkylene-H or $(C_1-C_4)$alkylene-O—$(C_1-C_4)$alkylene-phenyl, where alkylene can be substituted by O—$(C_1-C_4)$alkyl, preferably methoxy or ethoxy;

$R_6$ is para-$CF_3$ or p-$SF_5$; and $R_7$ is H.

Another embodiment of this invention is a compound of the formula I in which

X is a bond;

$R_1$ is Cl or —$CH_3$;

$R_2$ is H;

$R_3$ is H;

$R_4$ is H;

Z is a bond;

Y is —O—;

W is —$CH_2$;

U is N and

V is O or

U is O and

V is N;

$R_5$ is selected from the group comprising $(C_1-C_4)$alkyl, $(C_1-C_4)$alkylene-O—$(C_1-C_4)$alkylene-H or $(C_1-C_4)$alkylene-O—$(C_1-C_4)$alkylene-phenyl, where alkylene can be substituted by O—$(C_1-C_4)$alkyl, preferably methoxy or ethoxy;

$R_6$ is para-$OCH_3$ or p-phenyl; and $R_7$ is H.

Another embodiment of this invention is a compound of the formula I in which $R_1$ is F, Cl, —$CH_3$, —$OCH_3$, preferably F, Cl.

Another embodiment of this invention is a compound of the formula I in which $R_5$ is $(C_1-C_4)$alkyl.

Another embodiment of this invention is a compound of the formula I in which $R_6$ is selected from the group comprising $CF_3$, $SF_5$, phenyl, $OCH_3$, preferably $CF_3$.

The most preferred compounds of the present claimed invention are:

3-{2-Fluoro-4-[4-methyl-2-(4-trifluoromethyl-phenyl)-thiazole-5-ylmethoxy]-phenyl}-4H-[1,2,4]oxadiazole-5-one 3-{4-[4-Methyl-2-(4-trifluoromethyl-phenyl)-thiazole-5-ylmethoxy]-phenyl}-4H-[1,2,4]oxadiazole-5-one 3-{3-Methoxy-4-[4-methyl-2-(4-trifluoromethyl-phenyl)-thiazole-5-ylmethoxy]-phenyl}-4H-[1,2,4]oxadiazole-5-one 3-{2-Chloro-4-[4-methyl-2-(4-trifluoromethyl-phenyl)-thiazole-5-ylmethoxy]-phenyl}-4H-[1,2,4]oxadiazole-5-one 3-{4-[4-Methyl-2-(4-trifluoromethyl-phenyl)-thiazole-5-ylmethylsulfanyl]-phenyl}-4H-[1,2,4]oxadiazole-5-one 3-{4-[4-Butyl-2-(4-trifluoromethyl-phenyl)-thiazole-5-ylmethoxy]-2-chloro-phenyl}-4H-[1,2,4]oxadiazole-5-one 3-{4-[4-Butyl-2-(4-pentafluorosulfanyl-phenyl)-thiazole-5-ylmethoxy]-2-chloro-phenyl}-4H-[1,2,4]oxadiazole-5-one 3-{2-Chloro-4-[4-methyl-2-(4-pentafluorosulfanyl-phenyl)-thiazole-5-ylmethoxy]-phenyl}-4H-[1,2,4]oxadiazole-5-one 3-(4-{2-[4-Butyl-2-(4-trifluoromethyl-phenyl)-thiazol-5-yl]-ethoxy}-2-chloro-phenyl)-4H-[1,2,4]oxadiazol-5-one 3-{4-[4-Butyl-2-(4-trifluoromethyl-phenyl)-thiazol-5-ylmethoxy]-2-chloro-benzyl}-4H-[1,2,4]oxadiazol-5-one 3-{2-Methoxy-4-[4-methyl-2-(4-trifluoromethyl-phenyl)-thiazol-5-ylmethoxy]-phenyl}-4H-[1,2,4]oxadiazol-5-one 3-{4-[4-Butyl-2-(4-trifluoromethyl-phenyl)-thiazol-5-ylmethoxy]-2-fluoro-phenyl}-4H-[1,2,4]oxadiazol-5-one 3-{4-[4-Butyl-2-(4-trifluoromethyl-phenyl)-thiazol-5-ylmethoxy]-2,6-difluoro-phenyl}-4H-[1,2,4]oxadiazol-5-one 3-{4-[4-Butyl-2-(4-trifluoromethyl-phenyl)-thiazol-5-ylmethylsulfanyl]-phenyl}-4H-[1,2,4]oxadiazol-5-one 3-{4-[4-Butyl-2-(4-trifluoromethyl-phenyl)-thiazol-5-ylmethoxy]-2-trifluoromethyl-phenyl}-4H-[1,2,4]oxadiazol-5-one 3-{4-[4-Butyl-2-(4-trifluoromethyl-phenyl)-thiazol-5-ylmethoxy]-2-methyl-pheny}-4H-[1,2,4]oxadiazol-5-one 3-{2-Bromo-4-[4-butyl-2-(4-trifluoromethyl-phenyl)-thiazol-5-ylmethoxy]-phenyl}-4H-[1,2,4]oxadiazol-5-one 3-{4-[4-Butyl-2-(4-trifluoromethyl-phenyl)-thiazol-5-yl-methoxy]-2-methoxy-phenyl}-4H-[1,2,4]oxadiazol-5-one 3-{4-[4-But-3-enyl-2-(4-trifluoromethyl-phenyl)-thiazol-5-ylmethoxy]-2-chloro-phenyl}-4H-[1,2,4]oxadiazol-5-one 3-{2-Chloro-4-[4-(4-hydroxy-butyl)-2-(4-trifluoromethyl-phenyl)-thiazol-5-ylmethoxy]-phenyl}-4H-[1,2,4]oxadiazol-5-one 3-{2-Chloro-4-[4-(3,4-dihydroxy-butyl)-2-(4-trifluoromethyl-phenyl)-thiazol-5-ylmethoxy]-phenyl}-4H-[1,2,4]oxadiazol-5-one 5-[4-Butyl-2-(4-trifluoromethyl-phenyl)-thiazol-5-ylmethoxy]-2-(5-oxo-4,5-dihydro-[1,2,4]oxadiazol-3-yl)-benzonitrile 3-{4-[4-Butyl-2-(4-trifluoromethyl-phenyl)-thiazol-5-ylmethoxy]-2-methylsulfanyl-phenyl}-4H-[1,2,4]oxadiazol-5-one 3-{4-[4-Butyl-2-(4-trifluoromethyl-phenyl)-thiazol-5-ylmethoxy]-2-methylsulfinyl-phenyl}-4H-[1,2,4]oxadiazol-5-one 3-{4-[4-Butyl-2-(4-trifluoromethyl-phenyl)-thiazol-5-ylmethoxy]-2-methanesulfonyl-phenyl}-4H-[1,2,4]oxadiazol-5-one 3-{4-[4-Butyl-2-(4-trifluoromethyl-phenyl)-thiazol-5-ylmethanesulfinyl]-phenyl}-4H-[1,2,4]oxadiazol-5-one 3-{4-[4-Butyl-2-(4-trifluoromethyl-phenyl)-thiazol-5-ylmethylsulfonyl]-phenyl}-4H-[1,2,4]oxadiazol-5-one 3-{4-[4-Butyl-2-(4-trifluoromethyl-phenyl)-thiazol-5-ylmethoxymethyl]-2-fluoro-phenyl}-4H-[1,2,4]oxadiazol-5-one 3-{4-[4-Methyl-2-(4-trifluoromethyl-phenyl)-thiazol-5-ylmethoxymethyl]-phenyl}-4H-[1,2,4]oxadiazol-5-one 3-[4-(2-Biphenyl-4-yl-5-methyl-oxazol-4-ylmethoxy)-2-chloro-phenyl]-4H-[1,2,4]oxadiazol-5-one 3-{2-Chloro-4-[2-(4-methoxy-phenyl)-5-methyl-oxazol-4-ylmethoxy]-phenyl}-4H-[1,2,4]oxadiazol-5-one 3-(2-Chloro-4-{2-[5-methyl-2-(4-trifluoromethyl-phenyl)-thiazol-4-yl]-ethoxy}-phenyl)-4H-[1,2,4]oxadiazol-5-one.

3-{2-Chloro-4-[4-methoxymethyl-2-(4-trifluoromethyl-phenyl)-thiazol-5-ylmethoxy]-phenyl}-4H-[1,2,4]oxadiazol-5-one 3-{2-Chloro-4-[4-(2-methoxy-ethoxymethyl)-2-(4-trifluoromethyl-phenyl)-thiazol-5-ylmethoxy]-phenyl}-4H-[1,2,4]oxadiazol-5-one 3-{2-Chloro-4-[4-(2-ethoxy-ethoxymethyl)-2-(4-trifluoromethyl-phenyl)-thiazol-5-ylmethoxy]-phenyl}-4H-[1,2,4]oxadiazol-5-one 3-{2-Chloro-4-[4-(3-methoxy-propoxymethyl)-2-(4-trifluoromethyl-phenyl)-thiazol-5-ylmethoxy]-phenyl}-4H-[1,2,4]oxadiazol-5-one 3-{4-[5-Methoxymethyl-2-(4-methoxy-phenyl)-oxazol-4-ylmethoxy]-2-methyl-phenyl}-4H-[1,2,4]oxadiazol-5-one 3-{4-[5-(2-Methoxy-ethoxymethyl)-2-(4-methoxy-phenyl)-oxazol-4-ylmethoxy]-2-methyl-phenyl}-4H-[1,2,4]oxadiazol-5-one 3-{4-[4-Methoxymethyl-2-(4-methoxy-phenyl)-oxazol-5-ylmethoxy]-2-methyl-phenyl}-4H-[1,2,4]oxadiazol-5-one 3-{4-[4-(2-Methoxy-ethoxymethyl)-2-(4-methoxy-phenyl)-oxazol-5-ylmethoxy]-2-methyl-phenyl}-4H-[1,2,4]oxadiazol-5-one 3-{4-[4-(2-Ethoxy-ethoxymethyl)-2-(4-methoxy-phenyl)-oxazol-5-ylmethoxy]-2-methyl-phenyl}-4H-[1,2,4]oxadiazol-5-one 3-{4-[2-(4-Methoxy-phenyl)-4-(3-methoxy-propoxymethyl)-oxazol-5-ylmethoxy]-2-methyl-phenyl}-4H-[1,2,4]oxadiazol-5-one 3-{4-[4-Ethoxymethyl-2-(4-methoxy-phenyl)-oxazol-5-ylmethoxy]-2-methyl-phenyl}-4H-[1,2,4]oxadiazol-5-one 3-{4-[4-Benzyloxymethyl-2-(4-methoxy-phenyl)-oxazol-5-ylmethoxy]-2-methyl-phenyl}-4H-[1,2,4]oxadiazol-5-one 3-{2-Chloro-4-[5-methoxymethyl-2-(4-methoxy-phenyl)-oxazol-4-ylmethoxy]-phenyl}-4H-[1,2,4]oxadiazol-5-one 3-{2-Chloro-4-[5-(2-methoxy-ethoxymethyl)-2-(4-methoxy-phenyl)-oxazol-4-ylmethoxy]-phenyl}-4H-[1,2,4]oxadiazol-5-one 3-{2-Chloro-4-[4-methoxymethyl-2-(4-methoxy-phenyl)-oxazol-5-ylmethoxy]-phenyl}-4H-[1,2,4]oxadiazol-5-one 3-{2-Chloro-4-[2-(4-methoxy-phenyl)-4-(3-methoxy-propoxymethyl)-oxazol-5-ylmethoxy]-phenyl}-4H-[1,2,4]oxadiazol-5-one 3-{5-Bromo-2-methoxy-4-[4-methyl-2-(4-trifluoromethyl-phenyl)-thiazol-5-ylmethoxy]-phenyl}-4H-[1,2,4]oxadiazol-5-one 3-{4-[4-(3-Benzyloxy-propyl)-2-(4-trifluoromethyl-phenyl)-thiazol-5-ylmethoxy]-2-chloro-phenyl}-4H-[1,2,4]oxadiazol-5-one 3-{2-chloro-4-[4-(3-hydroxy-propyl)-2-(4-trifluoromethyl-phenyl)-thiazol-5-ylmethoxy]-phenyl}-4H-[1,2,4]oxadiazol-5-one This invention also encompasses all combinations of preferred aspects of the invention described herein.

The alkyl and alkenyl radicals in the substituents $R_1$, $R_2$, $R_3$, $R_4$, $R_5$, $R_6$ and $R_7$ may be either straight-chain or branched.

The compounds of the formula I may exist in the form of their racemates, racemic mixtures, pure enantiomers, diastereomers and mixtures of diastereomers as well in their tautomeric forms. The present invention encompasses all these isomeric and tautomeric forms of the compounds of the formula I as well as mixtures thereof. These isomeric forms can be obtained by known methods even if not specifically described in some cases.

Pharmaceutically acceptable salts are particularly suitable for medical applications, because their solubility in water is greater than that of the initial or basic compounds. These salts must have a pharmaceutically acceptable anion or cation charge. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzene sulfonic, benzoic, citric, ethane sulfonic, fumaric, gluconic, glycolic, isethionic, lactic, lactobionic, maleic, malic, methane sulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts), and salts of trometamol (2-amino-2-hydroxymethyl-1,3-propanediol), di-ethanolamine, lysine or ethylenediamine.

Salts with a pharmaceutically unacceptable anion are such as, for example, trifluoroacetate likewise fall within the scope of the invention as useful intermediates for the preparation or purification of pharmaceutically acceptable salts and/or for use in non-therapeutic, for example in vitro, applications.

The term "physiologically functional derivative" used herein refers to any physiologically tolerated derivative of a compound of the formula I of the invention, for example an ester, which on administration to a mammal such as, for example, a human, is able to form (directly or indirectly) a compound of the formula I or an active metabolite thereof.

Physiologically functional derivatives also include prodrugs of the compounds of the invention, as described, for example, in H. Okada et al., Chem. Pharm. Bull. 1994, 42, 57-61. Such prodrugs can be metabolized in vivo to a compound of the invention. These prodrugs themselves may be active or not.

The compounds of the invention may also exist in various polymorphous forms, for example as amorphous and crystalline polymorphous forms. All polymorphous forms of the compounds of the invention fall within the scope of the invention and are a further aspect of the invention.

All references to "compound(s) of formula I" hereinafter refer to compound(s) of the formula I as described above, and their salts, solvates and physiologically functional derivatives as described herein.

Use

This invention relates further to the use of compounds of the formula I and their pharmaceutical compositions as peroxisome proliferators—activator receptor (PPAR) ligands. The PPAR ligands of the invention are suitable as modulators of PPAR activity.

Peroxisome proliferator-activated receptors (PPAR) are transcription factors which can be activated by ligands and belong to the class of nuclear hormone receptors. There are three PPAR isoforms, PPARalpha, PPARgamma and PPARdelta (identical to PPARbeta), which are encoded by different genes (Peroxisome proliferator-activated receptor (PPAR): structure, mechanisms of activation and diverse functions: Motojima K., Cell Struct Funct., 1993, 18(5), 267-77).

In humans, PPARgamma exists in three variants, PPAR-gamma$_1$, gamma$_2$, and gamma$_3$, which are the result of alternative use of promoters and differential mRNA splicing. Different PPARs have different tissue distribution and modulate different physiological functions. The PPARs play a key role in various aspects of the regulation of a large number of genes, the products of which genes are directly or indirectly crucially involved in lipid and carbohydrate metabolism. Thus, for example, the PPARalpha receptor plays an important part in the regulation of fatty acid catabolism or lipoprotein metabolism in the liver, while PPARgamma is crucially involved for example in regulating adipose cell differentiation. In addition, however, PPARs are also involved in the regulation of many other physiological processes, including those which are not directly connected with carbohydrate or lipid metabolism. The activity of different PPARs can be modulated by various fatty acids, fatty acid derivatives and synthetic compounds to varying extents. For relevant reviews about functions, physiological effects and pathophysiology, see: Berger, J. et al., Annu. Rev. Med., 2002, 53, 409-435; Wilson, T. et al., J. Med. Chem., 2000, 43 (4), 527-550; Kliewer, S. et al., Recent Prog Horm Res., 2001, 56, 239-63; Moller, D. E. and Berger, J. P., Int J Obes Relat Metab Disord., 2003, 27 Suppl 3, 17-21; Ram, V. J., Drugs Today, 2003, 39(8), 609-32).

Among the three PPAR-isoforms the physiological functions of PPARdelta have long remained an enigma. The first proposed pharmacological role for PPARdelta has been the regulation of cholesterol homeostasis. It was shown that the somewhat selective PPARdelta ligand L-165041 raises plasma cholesterol in a diabetic animal model (Berger J. et al., J. Biol. Chem., 1999, 274, 6718-6725; Leibowitz M. D. et al., FEBS Lett., 2000, 473(3), 333-336). In obese, insulin resistant rhesus monkeys, the potent and selective PPARdelta ligand GW501516 raises HDL-cholesterol, decreases plasma LDL-cholesterol, triglycerides and insulin levels (Oliver, W. et al., Proc. Natl. Acad. Sci., 2001, 98, 5306-5311). The dual PPARdelta/PPARalpha agonist YM-16638 significantly lowers plasma lipids in rhesus and cynomolgus monkeys (Goto, S. et al., Br. J. Pharm., 1996, 118, 174-178) and acts in a similar manner in two weeks clinical trials in healthy volunteers (Shimokawa, T. et al., Drug Dev. Res., 1996, 38, 86-92). More recent publications underline that PPARdelta is an important target for the treatment of dyslipidemia, insulin resistance, type 2 diabetes, atherosclerosis and syndrom X (Wang,Y.-X. et al., Cell, 2003, 113, 159-170; Luquet, S. et al., FASEB J., 2003, 17, 209-226; Tanaka, T. et al., PNAS, 2003, 100, 15924-15929; Holst, D. et al., BioChem. Biophys. Acta, 2003, 1633, 43-50; Dressel, U. et al., Mol. Endocrin., 2003, 17, 2477-2493; Lee, C. H. et al., Science, 2003, 302, 453-457).

Besides its actions as a regulator of the lipid-, glucose- and cholesterol-metabolism PPARdelta is known to play a role in embryonic development, implantation and bone formation (Lim, H. and Dey, S. K., Trends Endocrinol Metab., 2000, 11(4), 137-42; Ding, N. Z. et al., Mol Reprod Dev., 2003, 66(3), 218-24; Mano, H. et al., J Biol. Chem., 2000, 275(11), 8126-32).

Numerous publications demonstrate that PPARdelta is triggering proliferation and differentiation of keratinocytes which points to its role in skin disorders and wound healing (Di-Poi, N. et al., J Steroid Biochem Mol. Biol., 2003, 85(2-5), 257-65; Tan, N. S. et al., Am J Clin Dermatol., 2003, 4(8), 523-30; Wahli, W., Swiss Med. Wkly., 2002, 132(7-8), 83-91).

PPARdelta appears to be significantly expressed in the CNS; however much of its function there still remains undiscovered. Of singular interest however, is the discovery that PPARdelta was expressed in rodent oligodendrocytes, the major lipid producing cells of the CNS (J. Granneman, et al., J. Neurosci. Res., 1998, 51, 563-573). Moreover, it was also found that a PPARdelta selective agonist was found to significantly increase oligodendroglial myelin gene expression and myelin sheath diameter in mouse cultures (I. Saluja et al., Glia, 2001, 33, 194-204). Thus, PPARdelta activators may be of use for the treatment of demyelinating and dysmyelinating diseases.

Demyelinating conditions are manifested in loss of myelin, the multiple dense layers of lipids and protein which cover many nerve fibers. These layers are provided by oligodendroglia in the central nervous system (CNS), and Schwann cells in the peripheral nervous system (PNS). In patients with demyelinating conditions, demyelination may be irreversible; it is usually accompanied or followed by axonal degeneration, and often by cellular degeneration. Demyelination can occur as a result of neuronal damage or damage to the myelin itself—whether due to aberrant immune responses, local injury, ischemia, metabolic disorders, toxic agents, or viral infections (Prineas and McDonald, Demyelinating Diseases. In Greenfield's Neuropathology, 6.sup.th ed. (Edward Arnold: New York, 1997) 813-811, Beers and Berkow, eds., The Merck Manual of Diagnosis and Therapy, 17.sup.th ed. (Whitehouse Station, N.J.: Merck Research Laboratories, 1999) 1299, 1437, 1473-76, 1483).

Central demyelination (demyelination of the CNS) occurs in several conditions, often of uncertain etiology, that have come to be known as the primary demyelinating diseases. Other of these, multiple sclerosis (MS) is the most prevalent. Other primary demyelinating diseases include adrenoleukodystrophy (ALD), adrenomyeloneuropathy, AIDS-vacuolar myelopathy, HTLV-associated myelopathy, Leber's hereditary optic atrophy, progressive multifocal leukoencephalopathy (PML), subacute sclerosing panencephalitis, Guillian-Barre syndrome and tropical spastic paraparesis. In addition, there are acute conditions in which demyelination can occur in the CNS, e.g., acute disseminated encephalomyelitis (ADEM) and acute viral encephalitis. Furthermore, acute transverse myelitis, a syndrome in which an acute spinal cord transection of unknown cause affects both gray and white matter in one or more adjacent thoracic segments, can also result in demyelination. Also, disorders in which myelin forming glial cells are damaged including spinal cord injuries, neuropathies and nerve injury.

The present invention relates to compounds of the formula I suitable for modulating the activity of PPARs, especially the activity of PPARdelta and PPARalpha. Depending on the modulation profile, the compounds of the formula I are suitable for the treatment, control and prophylaxis of the indications described hereinafter, and for a number of other pharmaceutical applications connected thereto (see, for example, Berger, J., et al., Annu. Rev. Med., 2002, 53, 409-435; Wilson, T. et al., J. Med. Chem., 2000, 43(4), 527-550; Kliewer, S. et al., Recent Prog Horm Res., 2001, 56, 239-63; Fruchart, J. C. et al., 2001, Pharmacological Research, 44(5), 345-52; Kersten, S. et al., Nature, 2000, 405, 421-424; Torra, I. P. et al., Curr Opin Lipidol, 2001, 12, 245-254).

Compounds of this type are particularly suitable for the treatment and/or prevention of:
1. Disorders of fatty acid metabolism and glucose utilization disorders.
   Disorders in which insulin resistance is involved
2. Diabetes mellitus, especially type-2 diabetes, including the prevention of the sequelae associated therewith.
   Particular aspects in this connection are
   hyperglycemia,
   improvement in insulin resistance,
   improvement in glucose tolerance,
   protection of the pancreatic β cells
   prevention of macro- and microvascular disorders
3. Dyslipidemias and their sequelae such as, for example, atherosclerosis, coronary heart disease, cerebrovascular disorders etc, especially those (but not restricted thereto) which are characterized by one or more of the following factors:
   high plasma triglyceride concentrations, high postprandial plasma triglyceride concentrations,
   low HDL cholesterol concentrations
   low ApoA lipoprotein concentrations
   high LDL cholesterol concentrations
   small dense LDL cholesterol particles
   high ApoB lipoprotein concentrations
4. Various other conditions which may be associated with the metabolic syndrome, such as:
   obesity (excess weight), including central obesity
   thromboses, hypercoagulable and prothrombotic states (arterial and venous)
   high blood pressure
   heart failure such as, for example (but not restricted thereto), following myocardial infarction, hypertensive heart disease or cardiomyopathy
5. Disorders or conditions in which inflammatory reactions are involved:
   atherosclerosis such as, for example (but not restricted thereto), coronary sclerosis including angina pectoris or myocardial infarction, stroke
   vascular restenosis or reocclusion
   chronic inflammatory bowel diseases such as, for example, Crohn's disease and ulcerative colitis
   asthma
   lupus erythematosus (LE) or inflammatory rheumatic disorders such as, for example, rheumatoid arthritis
   other inflammatory states
6. Disorders of cell cycle or cell differentiation processes:
   adipose cell tumors
   lipomatous carcinomas such as, for example, liposarcomas
   solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas etc
   acute and chronic myeloproliferative disorders and lymphomas
   angiogenesis
7. Neurodegenerative diseases and/or demyelinating disorders of the central and peripheral nervous systems and/or neurological diseases involving neuroinflammatory processes and/or other peripheral neuropathies:
   Alzheimer's disease
   multiple sclerosis
   Parkinson's disease
   adrenoleukodystrophy (ALD)
   adrenomyeloneuropathy
   AIDS-vacuolar myelopathy
   HTLV-associated myelopathy
   Leber's hereditary optic atrophy
   progressive multifocal leukoencephalopathy (PML)
   subacute sclerosing panencephalitis
   Guillian-Barre syndrome
   tropical spastic paraparesis
   acute disseminated encephalomyelitis (ADEM)
   acute viral encephalitis
   acute transverse myelitis
   spinal cord and brain trauma
   Charcot-Marie-Tooth disease
8. Skin disorders and/or disorders of wound healing processes:
   erythemato-squamous dermatoses such as, for example, psoriasis
   acne vulgaris
   other skin disorders and dermatological conditions which are modulated by PPAR
   eczemas and neurodermitis
   dermatitis such as, for example, seborrheic dermatitis or photodermatitis
   keratitis and keratoses such as, for example, seborrheic keratoses, senile keratoses, actinic keratosis, photo-induced keratoses or keratosis follicularis
   keloids and keloid prophylaxis
   warts, including condylomata or condylomata acuminata
   human papilloma viral (HPV) infections such as, for example, venereal papillomata, viral warts such as, for example, molluscum contagiosum, leukoplakia
   papular dermatoses such as, for example, Lichen planus
   skin cancer such as, for example, basal-cell carcinomas, melanomas or cutaneous T-cell lymphomas
   localized benign epidermal tumors such as, for example, keratoderma, epidermal naevi
   chilblains
   wound healing
9. Other disorders
   high blood pressure
   pancreatitis
   syndrome X
   polycystic ovary syndrome (PCOS)

asthma osteoarthritis lupus erythematosus (LE) or inflammatory rheumatic disorders such as, for example, rheumatoid arthritis vasculitis wasting (cachexia)

gout ischemia/reperfusion syndrome acute respiratory distress syndrome (ARDS)

Formulations

The amount of a compound of formula I necessary to achieve the desired biological effect depends on a number of factors, for example the specific compound chosen, the intended use, the mode of administration and the clinical condition of the patient. The daily dose is generally in the range from 0.001 mg to 100 mg (typically from 0.01 mg to 50 mg) per day and per kilogram of bodyweight, for example 0.1-10 mg/kg/day. An intravenous dose may be, for example, in the range from 0.001 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampules for injections may contain, for example, from 1 mg to 100 mg, and single-dose formulations which can be administered orally, such as, for example, capsules or tablets, may contain, for example, from 0.05 to 1000 mg, typically from 0.5 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units such as, for example, capsules, cachets, suckable tablets or tablets, each of which contain a defined amount of the compound of formula I; as powders or granules, as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing a compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single plasters which are suitable for long-term close contact with the patient's epidermis. Such plasters suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compounds of the formula I are distinguished by favorable effects on metabolic disorders. They beneficially influence lipid and sugar metabolism, in particular they lower the triglyceride level and are suitable for the prevention and treatment of type II diabetes and atherosclerosis and the diverse sequalae thereof.

Combinations with Other Medicaments

The compounds of the invention can be administered alone or in combination with one or more further pharmacologically active substances which have, for example, favorable effects on metabolic disturbances or disorders frequently associated therewith. Examples of such medicaments are 1. medicaments which lower blood glucose, antidiabetics,
2. active ingredients for the treatment of dyslipidemias,
3. anti-atherosclerotic medicaments,
4. anti-obesity agents,
5. anti-inflammatory active ingredients
6. active ingredients for the treatment of malignant tumors
7. anti-thrombotic active ingredients
8. active ingredients for the treatment of high blood pressure
9. active ingredients for the treatment of heart failure and
10. active ingredients for the treatment and/or prevention of complications caused by diabetes or associated with diabetes.

They can be combined with the compounds of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation.

Examples of suitable drugs useful in combination with the PPAR agonists of the present invention include, but are not limited to:

Antidiabetics

Suitable antidiabetics are disclosed for example in the Rote Liste 2001, chapter 12 or in the USP Dictionary of USAN and International Drug Names, US Pharmacopeia, Rockville 2001. Antidiabetics include all insulins and insulin derivatives such as, for example, Lantus® (see www.lantus.com) or Apidra®, and other fast-acting insulins (see U.S. Pat. No. 6,221,633), GLP-1 receptor modulators as described in WO 01/04146 or else, for example, those disclosed in WO 98/08871 of Novo Nordisk A/S.

The orally effective hypoglycemic active ingredients include, preferably, sulfonylureas, biguanides, meglitinides, oxadiazolidinediones, thiazolidinediones, glucosidase inhibitors, glucagon antagonists, GLP-1 agonists, DPP-IV inhibitors, potassium channel openers such as, for example, those disclosed in WO 97/26265 and WO 99/03861, insulin sensitizers, inhibitors of liver enzymes involved in the stimulation of gluconeogenesis and/or glycogenolysis, modulators of glucose uptake, compounds which alter lipid metabolism and lead to a change in the blood lipid composition, compounds which reduce food intake, PPAR and PXR modulators and active ingredients which act on the ATP-dependent potassium channel of the beta cells.

In one embodiment of the invention, the compounds of the formula I are administered in combination with insulin.

In one embodiment of the invention, the compounds of the formula I are administered in combination with substances which influence hepatic glucose production such as, for example, glycogen phosphorylase inhibitors (see: WO 01/94300, WO 02/096864, WO 03/084923, WO 03/084922, WO 03/104188)

In one embodiment, the compounds of the formula I are administered in combination with a sulfonylurea such as, for example, tolbutamide, glibenclamide, glipizide or glimepiride.

In one embodiment, the compounds of the formula I are administered in combination with an active ingredient which acts on the ATP-dependent potassium channel of the beta cells, such as, for example, tolbutamide, glibenclamide, glipizide, glimepiride or repaglinide.

In one embodiment, the compounds of the formula I are administered in combination with a biguanide such as, for example, metformin.

In a further embodiment, the compounds of the formula I are administered in combination with a meglitinide such as, for example, repaglinide.

In one embodiment, the compounds of the formula I are administered in combination with a thiazolidinedione such as, for example, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In one embodiment, the compounds of the formula I are administered in combination with a DPPIV inhibitor as described, for example, in WO98/19998, WO99/61431, WO99/67278, WO99/67279, WO01/72290, WO 02/38541, WO03/040174, in particular P 93/01 (1-cyclopentyl-3-methyl-1-oxo-2-pentaammonium chloride), P-31/98, LAF237 (1-[2-[3-hydroxyadamant-1-ylamino)acetyl]pyrrolidine-2-(S)-carbonitrile), TS021 ((2S,4S)-4-fluoro-1-[[(2-hydroxy-1,1-dimethylethyl)amino]-acetyl]pyrrolidine-2-carbonitrile monobenzenesulfonate).

In one embodiment of the invention, the compounds of the formula I are administered in combination with a PPAR-gamma agonist such as, for example, rosiglitazone, pioglitazone.

In one embodiment, the compounds of the formula I are administered in combination with compounds with an inhibitory effect on SGLT-1 and/or 2, as disclosed directly or indirectly for example in PCT/EP03/06841, PCT/EP03/13454 and PCT/EP03/13455.

In one embodiment, the compounds of the formula I are administered in combination with an α-glucosidase inhibitor such as, for example, miglitol or acarbose.

In one embodiment, the compounds of the formula I are administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

Lipid Modulators

In one embodiment of the invention, the compounds of the formula I are administered in combination with an HMGCoA reductase inhibitor such as lovastatin, fluvastatin, pravastatin, simvastatin, ivastatin, itavastatin, atorvastatin, rosuvastatin.

In one embodiment of the invention, the compounds of the formula I are administered in combination with a bile acid reabsorption inhibitor (see, for example, U.S. Pat. No. 6,245,744, U.S. Pat. No. 6,221,897, U.S. Pat. No. 6,277,831, EP 0683 773, EP 0683 774).

In one embodiment of the invention, the compounds of the formula I are administered in combination with a polymeric bile acid adsorbent such as, for example, cholestyramine, colesevelam.

In one embodiment of the invention, the compounds of the formula I are administered in combination with a cholesterol absorption inhibitor as described for example in WO 0250027, or ezetimibe, tiqueside, pamaqueside.

In one embodiment of the invention, the compounds of the formula I are administered in combination with an LDL receptor inducer (see, for example, U.S. Pat. No. 6,342,512).

In one embodiment, the compounds of the formula I are administered in combination with bulking agents, preferably insoluble bulking agents (see, for example, carob/Caromax®

(Zunft H J; et al., Carob pulp preparation for treatment of hypercholesterolemia, ADVANCES IN THERAPY (2001 September-October), 18(5), 230-6.) Caromax is a carob-containing product from Nutrinova, Nutrition Specialties & Food Ingredients GmbH, Industriepark Höechst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

In one embodiment of the invention, the compounds of the formula I are administered in combination with a PPARalpha agonist.

In one embodiment of the invention, the compounds of the formula I are administered in combination with a mixed PPAR alpha/gamma agonist such as, for example, AZ 242 (Tesaglitazar, (S)-3-(4-[2-(4-methanesulfonyloxyphenyl)ethoxy]phenyl)-2-ethoxypropionic acid), BMS 298585 (N-[(4-methoxyphenoxy)carbonyl]-N-[[4-[2-(5-methyl-2-phenyl-4-oxazolyl)ethoxy]phenyl]methyl]glycine) or as described in WO 99/62872, WO 99/62871, WO 01/40171, WO 01/40169, WO96/38428, WO 01/81327, WO 01/21602, WO 03/020269, WO 00/64888 or WO 00/64876.

In one embodiment of the invention, the compounds of the formula I are administered in combination with a fibrate such as, for example, fenofibrate, gemfibrozil, clofibrate, bezafibrate.

In one embodiment of the invention, the compounds of the formula I are administered in combination with nicotinic acid or niacin.

In one embodiment of the invention, the compounds of the formula I are administered in combination with a CETP inhibitor, e.g. CP-529, 414 (torcetrapib).

In one embodiment of the invention, the compounds of the formula I are administered in combination with an ACAT inhibitor.

In one embodiment of the invention, the compounds of the formula I are administered in combination with an MTP inhibitor such as, for example, implitapide.

In one embodiment of the invention, the compounds of the formula I are administered in combination with an antioxidant.

In one embodiment of the invention, the compounds of the formula I are administered in combination with a lipoprotein lipase inhibitor.

In one embodiment of the invention, the compounds of the formula I are administered in combination with an ATP citrate lyase inhibitor.

In one embodiment of the invention, the compounds of the formula I are administered in combination with a squalene synthetase inhibitor.

In one embodiment of the invention, the compounds of the formula I are administered in combination with a lipoprotein (a) antagonist.

Antiobesity Agents

In one embodiment of the invention, the compounds of the formula I are administered in combination with a lipase inhibitor such as, for example, orlistat.

In one embodiment, the further active ingredient is fenfluramine or dexfenfluramine.

In another embodiment, the further active ingredient is sibutramine.

In a further embodiment, the compounds of the formula I are administered in combination with CART modulators (see "Cocaine-amphetamine-regulated transcript influences energy metabolism, anxiety and gastric emptying in mice" Asakawa, A, et al., M. Hormone and Metabolic Research (2001), 33(9), 554-558), NPY antagonists, e.g. naphthalene-1-sulfonic acid {4-[(4-aminoquinazolin-2-ylamino)methyl]-cyclohexylmethyl}amide hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]-amide; (WO 01/91752)), orexin antagonists (e.g. 1-(2-methylbenzoxazol-6-yl)-3-[1,5]naphthyridin-4-ylurea hydrochloride (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]-ethanol hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexyl-ethyl)thiazole-2-ylcarbamoyl]-5,7-dimethylindol-1-yl}acetic acid trifluoroacetic acid salt (WO 99/15525)), serotonin reuptake inhibitors (e.g. dexfenfluramine), mixed serotoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tertiary butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists.

In one embodiment of the invention, the further active ingredient is leptin.

In one embodiment, the further active ingredient is dexamphetamine, amphetamine, mazindole or phentermine.

In one embodiment, the compounds of the formula I are administered in combination with medicaments having effects on the coronary circulation and the vascular system, such as, for example, ACE inhibitors (e.g. ramipril), medicaments which act on the angiotensin-renine system, calcium antagonists, beta blockers etc.

In one embodiment, the compounds of the formula I are administered in combination with medicaments having an antiinflammatory effect.

In one embodiment, the compounds of the formula I are administered in combination with medicaments which are employed for cancer therapy and cancer prevention.

It will be appreciated that every suitable combination of the compounds of the invention with one or more of the aforementioned compounds and optionally one or more other pharmacologically active substances is regarded as falling within the protection conferred by the present invention.

The activity of the compounds was tested as follows:

Determination of EC50 Values of PPAR Agonists in the Cellular PPARalpha Assay

Principle

The potency of substances which bind to human PPARalpha and activate it in an agonistic manner is analyzed using a stably transfected HEK cell line (HEK=human embryo kidney) which is referred to here as PPARalpha reporter cell line. It contains two genetic elements, a luciferase reporter element (pdeltaM-GAL4-Luc-Zeo) and a PPARalpha fusion protein (GR-GAL4-humanPPARalpha-LBD) which mediates expression of the luciferase reporter element depending on a PPARalpha ligand. The stably and constitutively expressed fusion protein GR-GAL4-humanPPARalpha-LBD binds in the cell nucleus of the PPARalpha reporter cell line via the GAL4 protein portion to the GAL4 DNA binding motifs 5'-upstream of the luciferase reporter element which is stably integrated in the genome of the cell line. There is only weak expression of the luciferase reporter gene in the absence of a PPARalpha ligand if fatty acid-depleted fetal calf serum (cs-FCS) is used in the assay. PPARalpha ligands bind and activate the PPARalpha fusion protein and thereby stimulate the expression of the luciferase reporter gene. The luciferase which is formed can be detected by means of chemiluminescence via an appropriate substrate.

Construction of the PPARalpha Reporter Cell Line

The PPARalpha reporter cell line was prepared in two stages. Firstly, the luciferase reporter element was constructed and stably transfected into HEK cells. For this purpose, five binding sites of the yeast transcription factor GAL4 (Accession # AF264724) were cloned in 5'-upstream of a 68 bp-long minimal MMTV promoter (Accession # V01175). The minimal MMTV promoter section contains a CCAAT box and a TATA element in order to enable efficient transcription by RNA polymerase II. The cloning and sequencing of the GAL4-MMTV construct took place in analogy to the description of Sambrook J. et al. (Molecular cloning, Cold Spring Harbor Laboratory Press, 1989). Then the complete Photinus pyralis gene (Accession # M15077) was cloned in 3'-downstream of the GAL4-MMTV element. After sequencing, the luciferase reporter element consisting of five GAL4 binding sites, MMTV promoter and luciferase gene was recloned into a plasmid which confers zeocin resistance in order to obtain the plasmid pdeltaM-GAL4-Luc-Zeo. This vector was transfected into HEK cells in accordance with the statements in Ausubel, F. M. et al. (Current protocols in molecular biology, Vol. 1-3, John Wiley & Sons, Inc., 1995). Then zeocin-containing medium (0.5 mg/ml) was used to select a suitable stable cell clone which showed very low basal expression of the luceriferase gene.

In a second step, the PPARalpha fusion protein (GR-GAL4-humanPPARalpha-LBD was introduced into the stable cell clone described. For this purpose, initially the cDNA coding for the N-terminal 76 amino acids of the glucocorticoid receptor (Accession # P04150) was linked to the cDNA section coding for amino acids 1-147 of the yeast transcription factor GAL4 (Accession # P04386). The cDNA of the ligand-binding domain of the human PPARalpha receptor (amino acids S167-Y468; Accession # S74349) was cloned in at the 3'-end of this GR-GAL4 construct. The fusion construct prepared in this way (GR-GAL4-humanPPARalpha-LBD) was recloned into the plasmid pcDNA3 (Invitrogen) in order to enable constitutive expression therein by the cytomegalovirus promoter. This plasmid was linearized with a restriction endonuclease and stably transfected into the previously described cell clone containing the luciferase reporter element. The finished PPARalpha reporter cell line which contains a luciferase reporter element and constitutively expresses the PPARalpha fusion protein (GR-GAL4-human PPARalpha-LBD) was isolated by selection with zeocin (0.5 mg/ml) and G418 (0.5 mg/ml).

Assay Procedure

The activity of PPARalpha agonists is determined in a 3-day assay, which is described below:

Day 1

The PPARalphareporter cell line is cultivated to 80% confluence in DMEM (# 41965-039, Invitrogen) which is mixed with the following additions: 10% cs-FCS (fetal calf serum; #SH-30068.03, Hyclone), 0.5 mg/ml zeocin (#R250-01, Invitrogen), 0.5 mg/ml G418 (#10131-027, Invitrogen), 1% penicillin-streptomycin solution (#15140-122, Invitrogen) and 2 mM L-glutamine (#25030-024, Invitrogen). The cultivation takes place in standard cell culture bottles (# 353112, Becton Dickinson) in a cell culture incubator at 37° C. in the presence of 5% $CO_2$. The 80%-confluent cells are washed once with 15 ml of PBS (#14190-094, Invitrogen), treated with 3 ml of trypsin solution (#25300-054, Invitrogen) at 37° C. for 2 min, taken up in 5 ml of the DMEM described and counted in a cell counter. After dilution to 500.000 cells/ml, 35,000 cells are seeded in each well of a 96 well microtiter plate with a clear plastic base (#3610, Corning Costar). The plates are incubated in the cell culture incubator at 37° C. and 5% $CO_2$ for 24 h.

Day 2

PPARalpha agonists to be tested are dissolved in DMSO in a concentration of 10 mM. This stock solution is diluted in DMEM (#41965-039, Invitrogen) which is mixed with 5% cs-FCS (#SH-30068.03, Hyclone), 2 mM L-glutamine (#25030-024, Invitrogen) and the previously described antibiotics (zeocin, G418, penicillin and streptomycin). Test substances are tested in 11 different concentrations in the range from 10 μM to 100 pM. More potent compounds are tested in concentration ranges from 1 μM to 10 pM or between 100 nM and 1 pM.

The medium of the PPARalpha reporter cell line seeded on day 1 is completely removed by aspiration, and the test substances diluted in medium are immediately added to the cells. The dilution and addition of the substances is carried out by a robot (Beckman FX). The final volume of the test substances diluted in medium is 100 μl per well of a 96 well microtiter plate. The DMSO concentration in the assay is less than 0.1% v/v in order to avoid cytotoxic effects of the solvent.

Each plate was charged with a standard PPARalpha agonist, which was likewise diluted in 11 different concentrations, in order to demonstrate the functioning of the assay in each individual plate. The assay plates are incubated in an incubator at 37° C. and 5% $CO_2$ for 24 h.

Day 3

The PPARalpha reporter cells treated with the test substances are removed from the incubator, and the medium is aspirated off. The cells are lyzed by pipetting 50 µl of Bright Glo reagent (from Promega) into each well of a 96 well microtiter plate. After incubation at room temperature in the dark for 10 minutes, the microtiter plates are measured in the luminometer (Trilux from Wallac). The measuring time for each well of a microtiter plate is 1 sec.

Evaluation

The raw data from the luminometer are transferred into a Microsoft Excel file. Dose-effect plots and EC50 values of PPAR agonists are calculated using the XL.Fit program as specified by the manufacturer (IDBS).

The PPARalpha EC50 values for the compounds of Examples 1 to 32 in this assay are in the range from 100 nM to >10 µM. Compounds of the invention of the formula I activate the PPARalpha receptor.

Determination of EC50 Values of PPAR Agonists in the Cellular PPARdelta Assay

Principle

The potency of substances which bind to human PPARdelta and activate it in an agonistic manner is analyzed using a stably transfected HEK cell line (HEK=human embryo kidney) which is referred to here as PPARdelta reporter cell line. In analogy to the assay described for PPARalpha, the PPARdelta reporter cell line also contains two genetic elements, a luciferase reporter element (pdeltaM-GAL4-Luc-Zeo) and a PPARdelta fusion protein (GR-GAL4-humanP-PARdelta-LBD) which mediates expression of the luciferase reporter element depending on a PPARdelta ligand. The stably and constitutively expressed fusion protein GR-GAL4-humanPPARdelta-LBD binds in the cell nucleus of the PPARdelta reporter cell line via the GAL4 protein portion to the GAL4 DNA binding motifs 5'-upstream of the luciferase reporter element which is stably integrated in the genome of the cell line. There is only little expression of the luciferase reporter gene in the absence of a PPARdelta ligand if fatty acid-depleted fetal calf serum (cs-FCS) is used in the assay. PPARdelta ligands bind and activate the PPARdelta fusion protein and thereby stimulate expression of the luciferase reporter gene. The luciferase which is formed can be detected by means of chemiluminescence via an appropriate substrate.

Construction of the PPARdelta Eporter Cell Line

The production of the stable PPARdelta reporter cell line is based on a stable HEK-cell clone which was stably transfected with a luciferase reporter element. This step was already described above in the section "construction of the PPARalpha reporter cell line". In a second step, the PPARdelta fusion protein (GR-GAL4-humanPPARdelta-LBD was stably introduced into this cell clone. For this purpose, the cDNA coding for the N-terminal 76 amino acids of the glucocorticoid receptor (Accession # P04150) was linked to the cDNA section coding for amino acids 1-147 of the yeast transcription factor GAL4 (Accession # P04386). The cDNA of the ligand-binding domain of the human PPARdelta receptor (amino acids S139-Y441; Accession # L07592) was cloned in at the 3'-end of this GR-GAL4 construct. The fusion construct prepared in this way (GR-GAL4-humanPPARdelta-LBD) was recloned into the plasmid pcDNA3 (Invitrogen) in order to enable constitutive expression by the cytomegalovirus promoter. This plasmid was linearized with a restriction endonuclease and stably transfected into the previously described cell clone containing the luciferase reporter element. The resulting PPARdelta reporter cell line which contains a luciferase reporter element and constitutively expresses the PPARdelta fusion protein (GR-GAL4-human PPARdelta-LBD) was isolated by selection with zeocin (0.5 mg/ml) and G418 (0.5 mg/ml).

Assay Procedure and Evaluation

The activity of PPARdelta agonists is determined in a 3-day assay in exact analogy to the procedure already described for the PPARalpha reporter cell line except that the PPARdelta reporter cell line and a specific PPARdelta agonist was used as a standard to control test efficacy.

PPARdelta EC50 values in the range from 0.2 nM to >10 µM were measured for the PPAR agonists of Examples 1 to 51 described in this application. Compounds of the invention of the formula I activate the PPARdelta receptor.

The following examples are provided to better explicitly describe how to make and use the compounds of the present invention and to specifically delineate bona fide embodiments of the PPAR agonits and their therapeutic value. They are for illustrative purposes only and should not be regarded as limiting the spirit and scope of the invention as recited in the claims that follow.

The examples given in Table I serve to illustrate the invention, but without limiting it.

TABLE I

Structure: R5-substituted thiazole/oxazole linked via W-Y-Z to phenyl(R1-R4) with X to 1,2,4-oxadiazol-5(4H)-one, and R6/R7-substituted phenyl.

| Example | X | Z | Y | W | U | V | R1 | R2 | R3 | R4 | R5 | R6 | R7 |
|---|---|---|---|---|---|---|---|---|---|---|---|---|---|
| 1 | — | — | O | —CH2— | S | N | F | H | H | H | CH3 | p-CF3 | H |
| 2 | — | — | O | —CH2— | S | N | H | H | H | H | CH3 | p-CF3 | H |
| 3 | — | — | O | —CH2— | S | N | H | H | CH3O | H | CH3 | p-CF3 | H |
| 4 | — | — | O | —CH2— | S | N | Cl | H | H | H | CH3 | p-CF3 | H |
| 5 | — | — | S | —CH2— | S | N | H | H | H | H | CH3 | p-CF3 | H |
| 6 | — | — | O | —CH2— | S | N | Cl | H | H | H | CH3 | p-SF5 | H |
| 7 | — | — | O | —CH2— | S | N | Cl | H | H | H | CH3 | p-SF5 | H |
| 8 | — | — | O | —CH2— | S | N | Cl | H | H | H | CH3 | p-CF3 | H |
| 9 | — | — | O | —CH2—CH2— | S | N | Cl | H | H | H | CH3—CH2—CH2—CH2— | p-CF3 | H |
| 10 | —CH2— | — | O | —CH2— | S | N | CH3O | H | H | H | CH3—CH2—CH2—CH2— | p-CF3 | H |
| 11 | — | — | O | —CH2— | S | N | F | F | H | H | CH3 | p-CF3 | H |
| 12 | — | — | S | —CH2— | S | N | H | H | H | H | CH3 | p-CF3 | H |
| 13 | — | — | O | —CH2— | S | N | CF3 | H | H | H | CH3 | p-CF3 | H |
| 14 | — | — | O | —CH2— | S | N | —CH3 | H | H | H | CH3—CH2—CH2—CH2— | p-CF3 | H |
| 15 | — | — | O | —CH2— | S | N | Br | H | H | H | CH3—CH2—CH2—CH2— | p-CF3 | H |
| 16 | — | — | O | —CH2— | S | N | CH3O | H | H | H | CH3—CH2—CH2—CH2— | p-CF3 | H |
| 17 | — | — | O | —CH2— | S | N | Cl | H | H | H | CH3—CH2—CH2—CH2— | p-CF3 | H |
| 18 | — | — | O | —CH2— | S | N | Cl | H | H | H | CH3—CH2—CH2—CH2— | p-CF3 | H |
| 19 | — | — | O | —CH2— | S | N | CN | H | H | H | CH3—CH2—CH2—CH2— | p-CF3 | H |
| 20 | — | — | O | —CH2— | S | N | CH3S— | H | H | H | CH2—CH2—CH2—CH2—CH2— | p-CF3 | H |
| 21 | — | — | O | —CH2— | S | N | CH3S(O)— | H | H | H | HO—CH2—CH2—CH2—CH2— | p-CF3 | H |
| 22 | — | — | O | —CH2— | S | N | CH3S(O)2— | H | H | H | HO—CH2—CH(OH)—CH2—CH2— | p-CF3 | H |
| 23 | — | — | O | —CH2— | S | N | H | H | H | H | CH3—CH2—CH2—CH2— | p-CF3 | H |
| 24 | — | — | O | —CH2— | S | N | Cl | H | H | H | CH3—CH2—CH2—CH2— | p-CF3 | H |
| 25 | — | — | O | —CH2— | S | N | Cl | H | H | H | CH3—CH2—CH2—CH2— | p-CF3 | H |
| 26 | — | —CH2— | S(O) | —CH2— | S | N | Cl | H | H | H | CH3—CH2—CH2—CH2— | p-CF3 | H |
| 27 | — | —CH2— | S(O)2 | —CH2— | S | N | Cl | H | H | H | CH3—CH2—CH2—CH2— | p-CF3 | H |
| 28 | — | — | O | —CH2— | O | N | F | H | H | H | CH3 | p-CF3 | H |
| 29 | — | — | O | —CH2— | S | O | H | H | H | H | CH3 | p-CF3 | H |
| 30 | — | — | O | —CH2— | N | S | Cl | H | H | H | CH3 | p-CF3 | H |
| 31 | — | — | O | —CH2—CH2— | N | N | Cl | H | H | H | CH3 | p-Phenyl | H |
| 32 | — | — | O | —CH2— | S | N | Cl | H | H | H | CH3 | p-OCH3 | H |
| 33 | — | — | O | —CH2— | S | N | Cl | H | H | H | CH3—O—CH2— | p-SF5 | H |
| 34 | — | — | O | —CH2— | S | N | Cl | H | H | H | CH3—O—CH2—CH2—O—CH2— | p-CF3 | H |
| 35 | — | — | O | —CH2— | S | N | Cl | H | H | H | CH3—O—CH2—CH2—O—CH2—O—CH2— | p-CF3 | H |
| 36 | — | — | O | —CH2— | S | N | Cl | H | H | H | CH3—O—CH2—CH2—CH2— | p-CF3 | H |
| 37 | — | — | O | —CH2— | N | O | —CH3 | H | H | H | CH3—O—CH2— | p-OCH3 | H |

TABLE I-continued

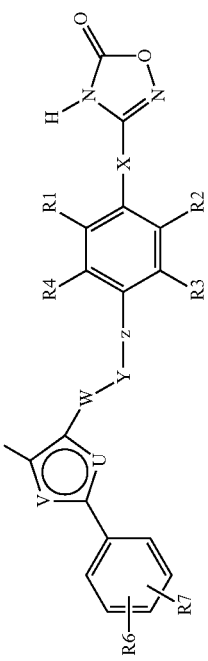

| Example | X | Z | Y | W | U | V | R1 | R2 | R3 | R4 | R5 | R6 | R7 |
|---|---|---|---|---|---|---|---|---|---|---|---|---|---|
| 38 | — | — | O | —CH2— | N | O | —CH3 | H | H | H | CH3—O—CH2—CH2—O—CH2— | p-OCH3 | H |
| 39 | — | — | O | —CH2— | O | N | —CH3 | H | H | H | CH3—O—CH2— | p-OCH3 | H |
| 40 | — | — | O | —CH2— | O | N | —CH3 | H | H | H | CH3—O—CH2—CH2— | p-OCH3 | H |
| 41 | — | — | O | —CH2— | O | N | —CH3 | H | H | H | CH3—O—CH2—CH2—O—CH2— | p-OCH3 | H |
| 42 | — | — | O | —CH2— | O | N | —CH3 | H | H | H | CH3—O—CH2—CH2—CH2—O—CH2— | p-OCH3 | H |
| 43 | — | — | O | —CH2— | O | N | —CH3 | H | H | H | CH3—CH2—O—CH2— | p-OCH3 | H |
| 44 | — | — | O | —CH2— | O | N | —CH3 | H | H | H | Ph-CH2—O—CH2— | p-OCH3 | H |
| 45 | — | — | O | —CH2— | N | O | Cl | H | H | H | CH3—O—CH2— | p-OCH3 | H |
| 46 | — | — | O | —CH2— | O | N | Cl | H | H | H | CH3—O—CH2—CH2—O—CH2— | p-OCH3 | H |
| 47 | — | — | O | —CH2— | O | N | Cl | H | H | H | CH3—O—CH2— | p-OCH3 | H |
| 48 | — | — | O | —CH2— | O | N | CH3O— | H | Br | H | CH3—O—CH2—CH2—O—CH2— | p-OCH3 | H |
| 49 | — | — | O | —CH2— | S | N | Cl | H | H | H | CH3— | p-CF3 | H |
| 50 | — | — | O | —CH2— | S | N | Cl | H | H | H | Ph-CH2—O—CH2—CH2— | p-CF3 | H |
| 51 | — | — | O | —CH2— | S | N | Cl | H | H | H | HO—CH2—CH2—CH2— | p-CF3 | H |

The potency of some of the described examples are indicated in the following table:

| Example | PPARalpha EC50 (µM) | PPARdelta EC50 (µM) |
|---|---|---|
| 4 | 1.66 | 0.056 |
| 5 | 1.33 | 0.068 |
| 10 | 0.77 | 0.011 |
| 13 | 0.36 | 0.010 |
| 15 | 0.15 | 0.003 |
| 18 | >10 | 0.015 |
| 20 | 1.56 | 0.055 |
| 28 | 0.12 | 0.023 |
| 30 | 0.25 | 0.016 |
| 32 | 0.32 | 0.31 |
| 34 | 0.23 | 0.001 |
| 50 | 0.42 | 0.0007 |

Processes

The compounds of the general formula I according to the invention can be obtained as outlined to the reaction schemes below:

Process A

A compound of the general formula A-1 where Y is —OH or —SH and X, Z, $R_1$, $R_2$, $R_3$ and $R_4$ are as defined is either reacted with an halide of general formula A-2 where R=halide and U, V, W, $R_5$, $R_6$ and $R_7$ are as defined in the presence of a base as cesium carbonate or sodium hydride in a solvent as dimethylformamide or with an alcohol of general formula A-2 where R=OH and U, V, W, $R_5$, $R_6$ and $R_7$ are as defined under Mitsunobu reaction conditions (triphenylphosphine, diethylazodicarboxylate for instance) in an apolar solvent as dichloromethane to give a compound of the general formula A-5. Alternatively the compound of general formula A-5 can be obtained by reacting a compound of general formula A-3 where R=halide, Z=—CH$_2$ and X, $R_1$, $R_2$, $R_3$ and $R_4$ are as defined with a compound of general formula A-4 where Y is —OH and U, V, W, $R_5$, $R_6$ and $R_7$ are as defined in the presence of a base as sodium hydride in a solvent as dimethylformamide. If Y=S in the compound of the general formula A-5, the sulfur atom can be oxidized (Y=SO or Y=SO2) by methods known in the art, e.g with a oxidizing agent as meta-chloroperbenzoic acid in an apolar solvent as dichloromethane. The compound of the general formula A-5 is reacted with hydroxylamine hydrochloride in the presence of a base as triethylamine in a solvent as tetrahydrofuran and methanol to obtain a compound of the general formula A-6. A

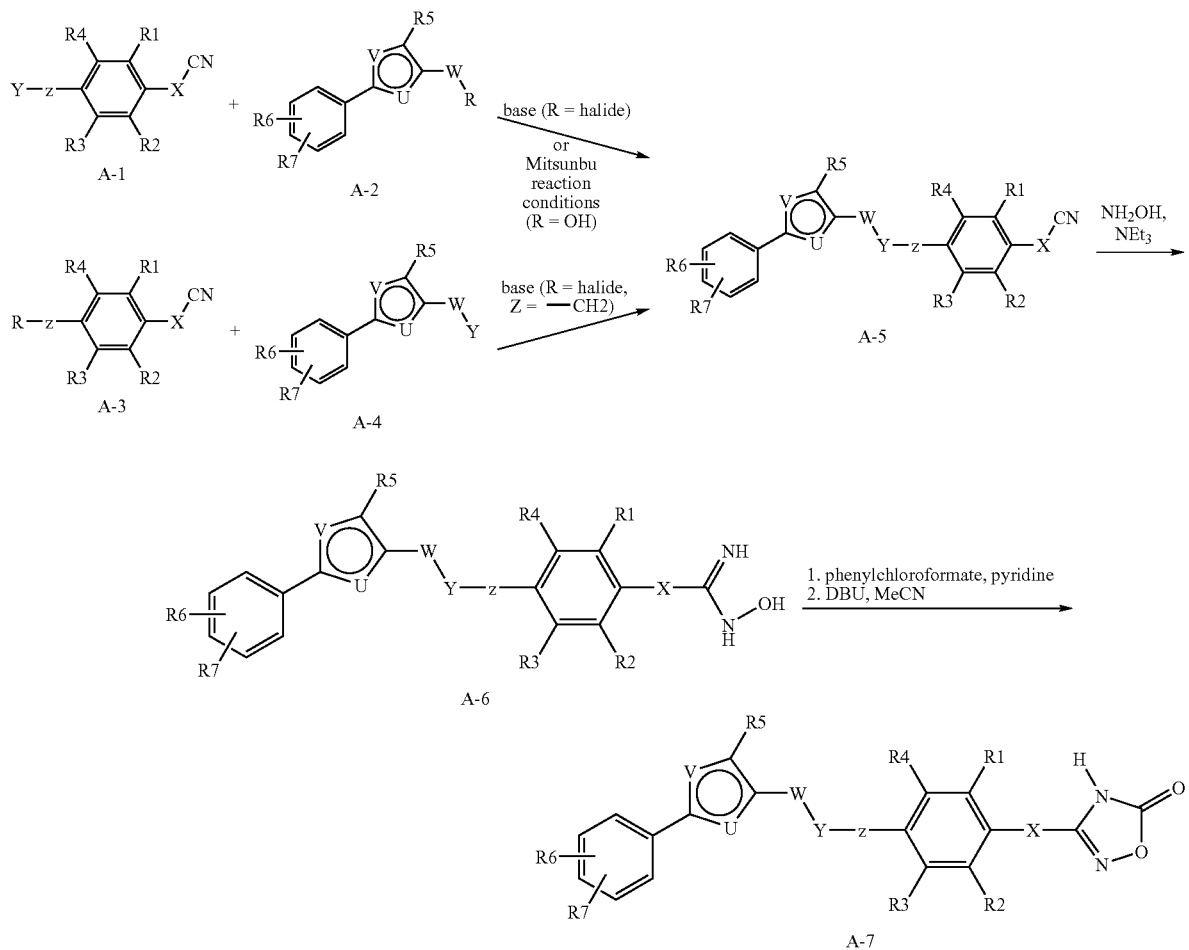

compound of the general formula A-6 is converted to the product of general formula A-7 by reaction with phenylchloroformate in the presence of a base as pyridine and treating this intermediate with a base as 1,8-diazabicyclo[5.4.0]undec-7-ene in a solvent as acetonitrile.

Examples 1-9, 12-14, 28-32 and 45-48 were obtained according to process A.

Other compounds can be obtained accordingly or by known processes.

Process B

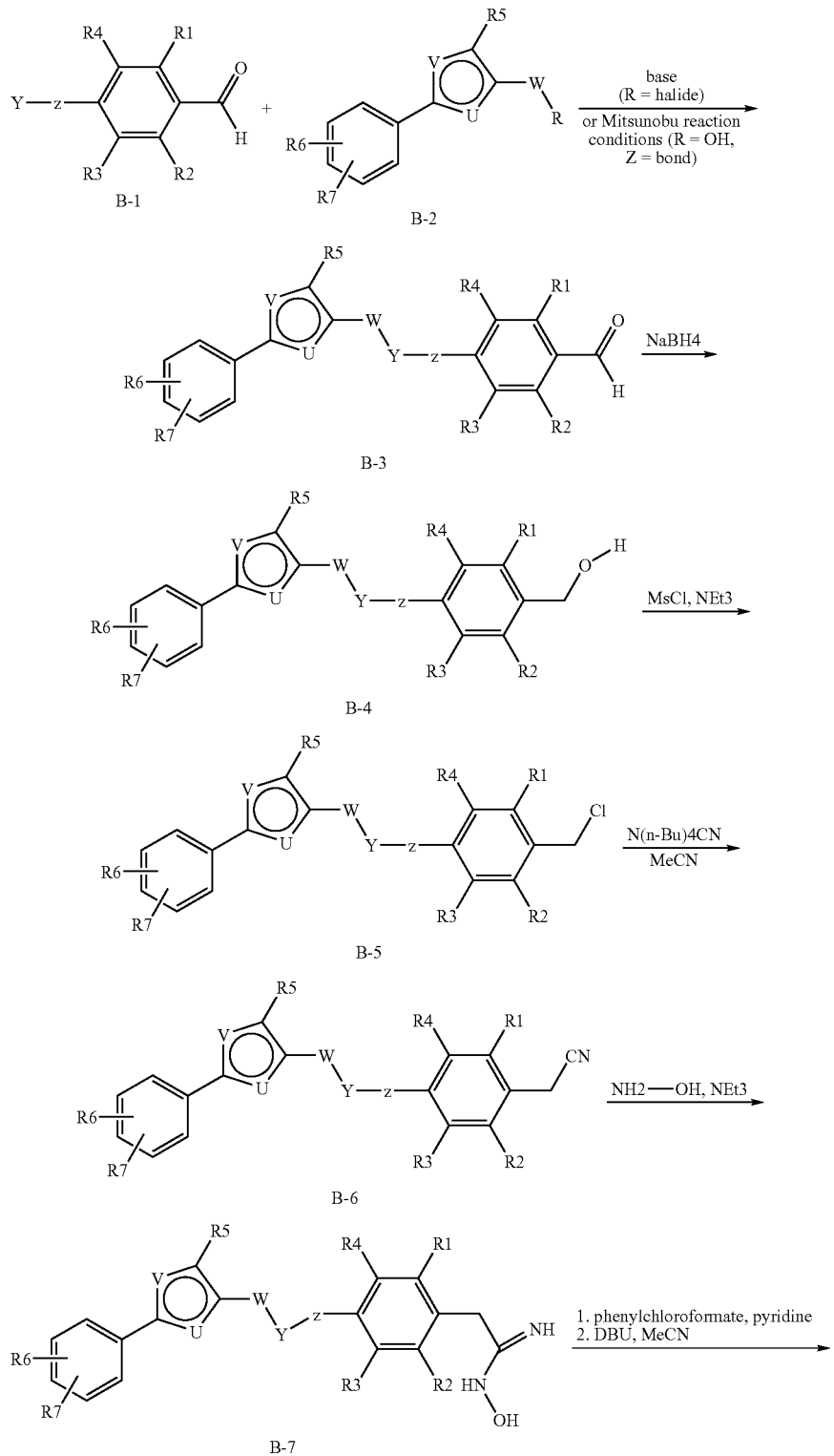

-continued

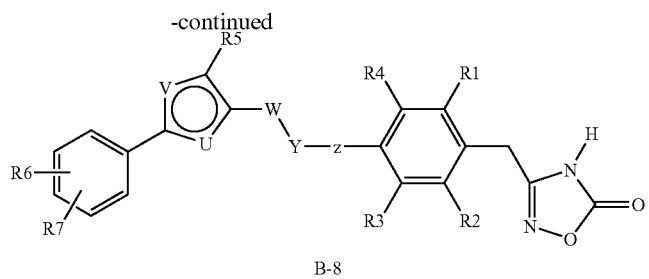

B-8

A compound of the general formula B-1 where Y is —OH or —SH and Z, R1, R2, R3 and R4 are as defined is either reacted with a halide of general formula B-2 where R=halide and U, V, W, R5, R6 and R7 are as defined in the presence of a base as cesium carbonate or sodium hydride in a solvent as dimethylformamide or with an alcohol of general formula B-2 where R=OH and U, V, W, R5, R6 and R7 are as defined under Mitsunobu reaction conditions (triphenylphosphine, diethylazodicarboxylate) in an apolar solvent as dichloromethane to give a compound of the general formula B-3. The compound of general formula B-3 is converted to the alcohol of general formula B-4 upon treatment with a reducing agent as sodium borohydride in a solvent as tetrahydrofuran. The alcohol of general formula B-4 is reacted with methanesulfonyl chloride in the presence of a base as triethylamine in a solvent as dichloromethane to obtain the compound of general formula B-5. The compound of general formula B-5 is reacted with tetrabutylammonium cyanide in a solvent as acetonitrile to obtain the compound of general formula B-6. A compound of the general formula B-6 is reacted with hydroxylamine hydrochloride in the presence of a base as triethylamine in a solvent as tetrahydrofuran and methanol to obtain a compound of the general formula B-7. A compound of the general formula B-7 is converted to the product of general formula B-8 by reaction with phenylchloroformate in the presence of a base as pyridine and treating this intermediate with a base as 1,8-Diazabicyclo[5.4.0]undec-7-ene in a solvent as acetonitrile.

Example 10 was obtained according to process B.

Other compounds can be obtained accordingly or by known processes.

Process C

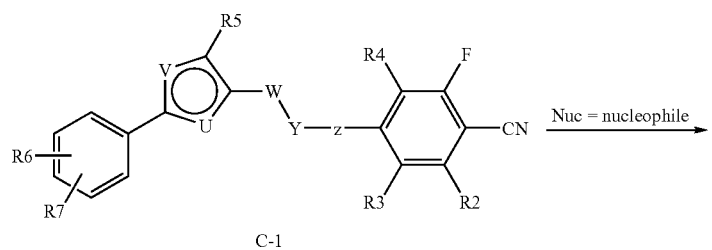

C-1

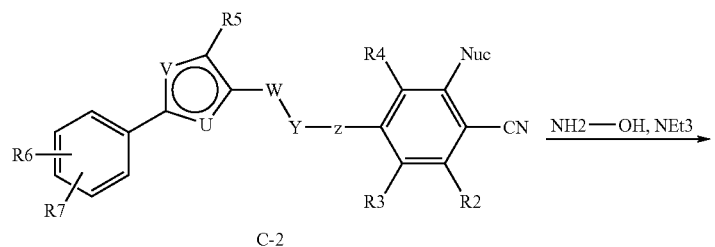

C-2

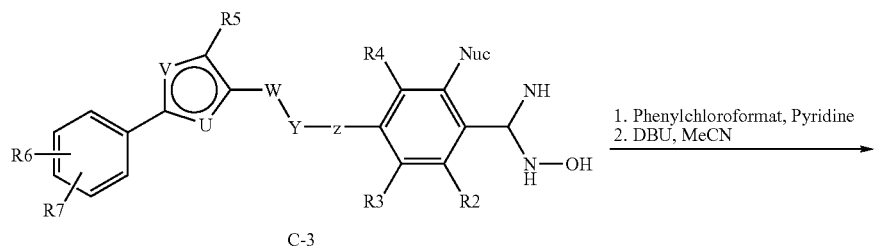

C-3

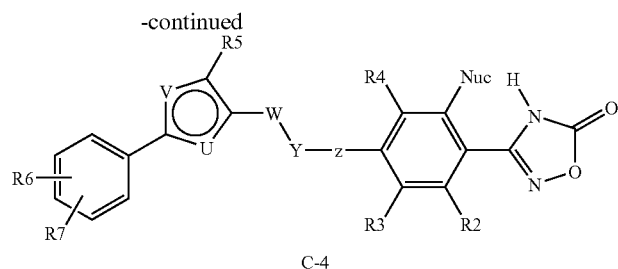

A compound of the general formula C-1 where R1=F and U, V, W, Y, Z, R2, R3, R4, R5, R6 and R7 are as defined is reacted with a nucleophile, e.g. sodium methylate, to obtain a compound of the general formula C-2. A compound of the general formula C-2 is reacted with hydroxylamine hydrochloride in the presence of a base as triethylamine in a solvent as tetrahydrofuran and methanol to obtain a compound of the general formula C-3. A compound of the general formula C-3 is converted to the product of general formula C-4 by reaction with phenylchloroformate in the presence of a base as pyridine and treating this intermediate with a base as 1,8-Diazabicyclo[5.4.0]undec-7-ene in a solvent as acetonitrile.

Example 11, 22 and 23 were obtained according to process C.

Other compounds can be obtained accordingly or by known processes.

Process D:

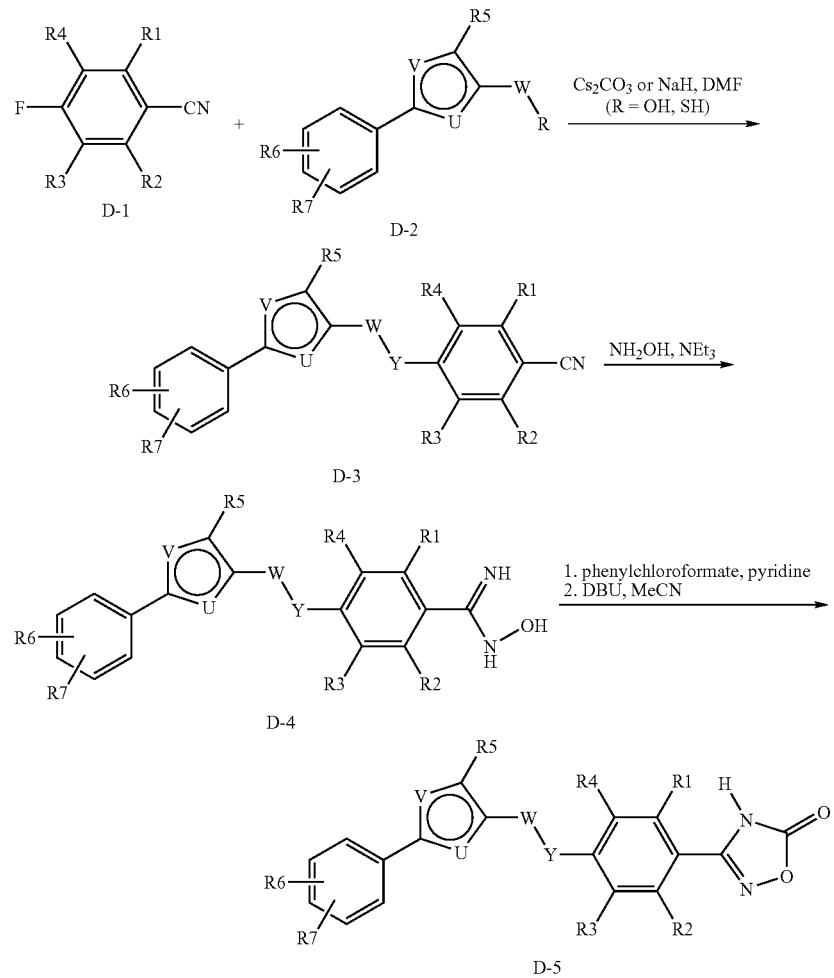

A compound of the general formula D-2 where R is —OH or —SH and U, V, W, R5, R6 and R7 are as defined above is reacted with a fluoro-nitrile of general formula D-1 where R1, R2, R3 and R4 are as defined above in the presence of a base such as cesium carbonate or sodium hydride in a solvent such as dimethylformamide to give a compound of the general formula D-3 where U, V, W, R1, R2, R3, R4, R5, R6 and R7 are as defined. If Y=S in the compound of the general formula D-3, the sulfur atom can be oxidized (Y=SO or Y=SO2) by methods known in the art, e.g with a oxidizing agent as meta-chloroperbenzoic acid in an apolar solvent as dichloromethane. As described in process A, compound D-3 is treated with hydroxylamine hydrochloride in the presence of a base such as triethylamine in a solvent as tetrahydrofuran and methanol to obtain a compound of the general formula D-4. Compound D-4 is converted to the product of general formula D-5 by reaction with phenylchloroformate in the presence of a base such as pyridine and treating this intermediate with a base such as 1,8-diazabicyclo[5.4.0]undec-7-ene in a solvent as acetonitrile.

Examples 15-19, 37-44 and 50 were obtained according to process D.

Other compounds can be obtained accordingly or by known processes.

Process E:

This process is used for synthesizing the building block E-4 where U, V, R5, R6 and R7 are as defined above.

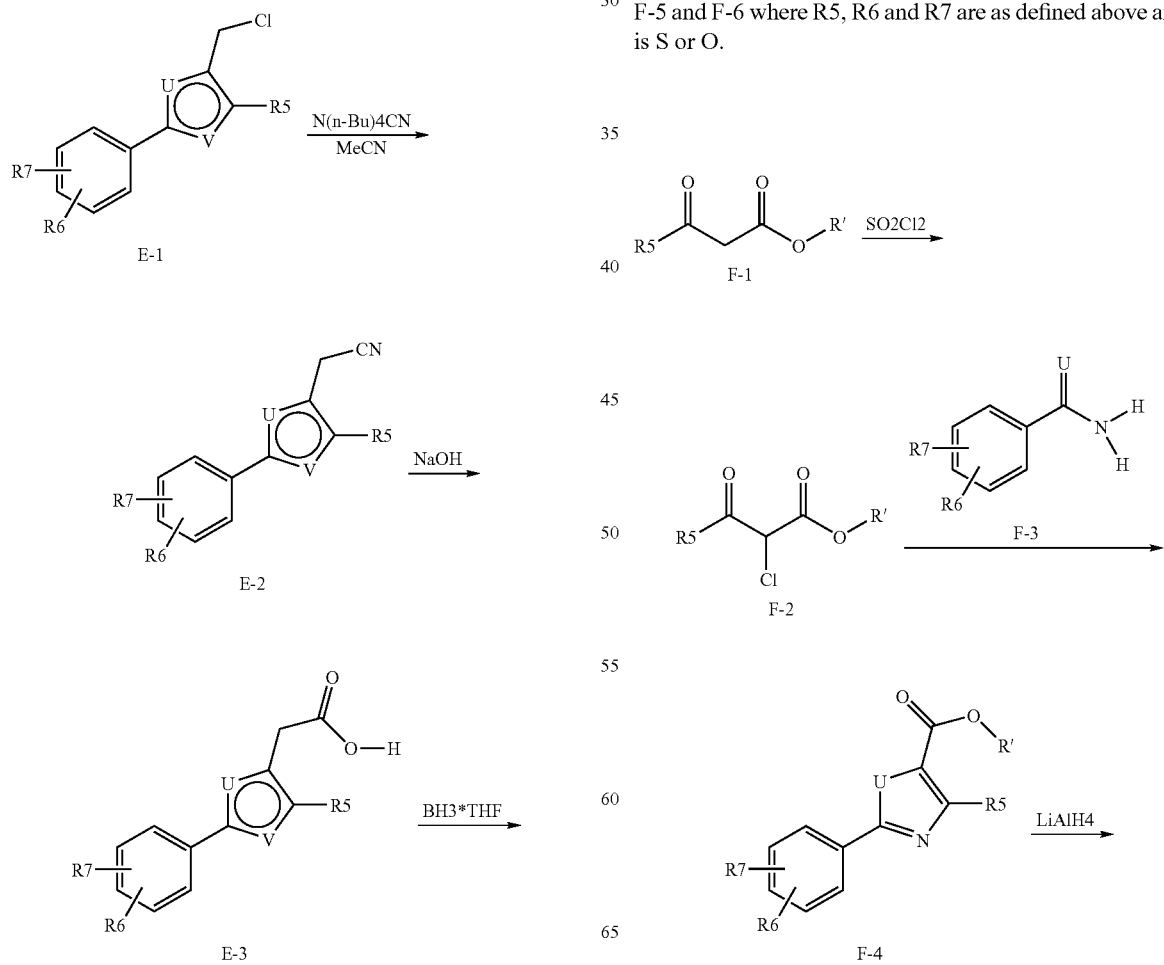

A halide of general formula E-1 where U, V, R5, R6 and R7 are as defined above is reacted with tetrabutylammonium cyanide in a solvent as acetonitrile to obtain a compound of general formula E-2. This compound of general formula E-2 is hydrolyzed with a base as sodium hydroxide to obtain the carboxylic acid of general formula E-3. The carboxylic acid of general formula E-3 is reduced with a reducing agent, e.g. borane, to the alcohol of general formula E-4.

Other compounds can be obtained accordingly or by known processes.

Process F:

This process is used for synthesizing the building blocks F-5 and F-6 where R5, R6 and R7 are as defined above and U is S or O.

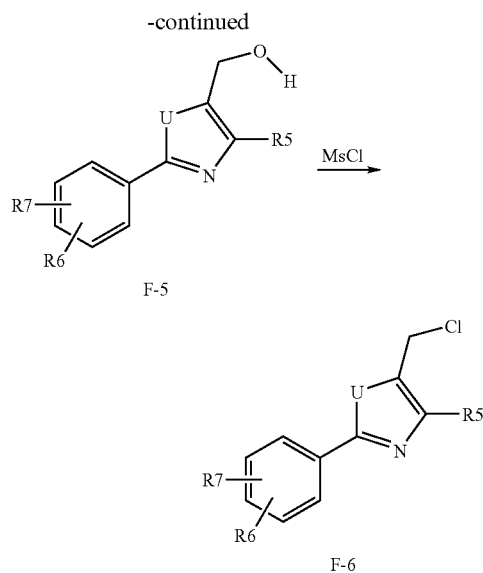

A 3-Oxo-butyric acid methyl- or ethyl ester of general formula F-1 where R5 is as defined above is reacted with sulfuryl chloride to a chlorine substituted compound of general formula F-2. This compound of general formula F-2 is reacted with a benzamide or thiobenzamide of general formula F-3, where U is S or O and R7 and R8 are as defined to obtain a phenylthiazole or phenyloxazole ester of general formula F-4. The ester of general formula F-4 is reduced with a reducing agent, e.g. lithium aluminium hydride, to the alcohol of general formula F-5. The alcohol of general formula F-5 is reacted with methanesulfonyl chloride in the presence of a base as triethylamine in a solvent as dichloromethane to obtain the building block of general formula F-6, where R5, R6 and R7 are as defined above.

Other compounds can be obtained accordingly or by known processes.

Process G:

This process is used for synthesizing the building blocks G-4 where V=S or O and R5, R6 and R7 are as defined above.

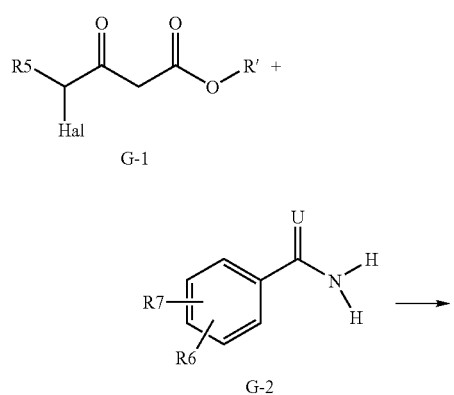

A halide of general formula G-1 where Hal=chlorine or bromine, R'=methyl or ethyl and R5 is as defined above is reacted with a benzamide or thiobenzamide of general formula G-2 where V=O or S and R6 and R7 are as defined above to obtain an ester of general formula G-3. The ester of general formula G-3 is reduced with a reducing agent, e.g. lithium aluminium hydride, to the alcohol of general formula G-4.

Other compounds can be obtained accordingly or by known processes.

Process $H^1$:

This process is used for synthesizing the building block H-4 and H-5 in which R5, R6 and R7 are as defined above.

U.S. Ser. No. 10/788,997; U.S. Ser. No. 10/788,996; U.S. Ser. No. 10/789,017

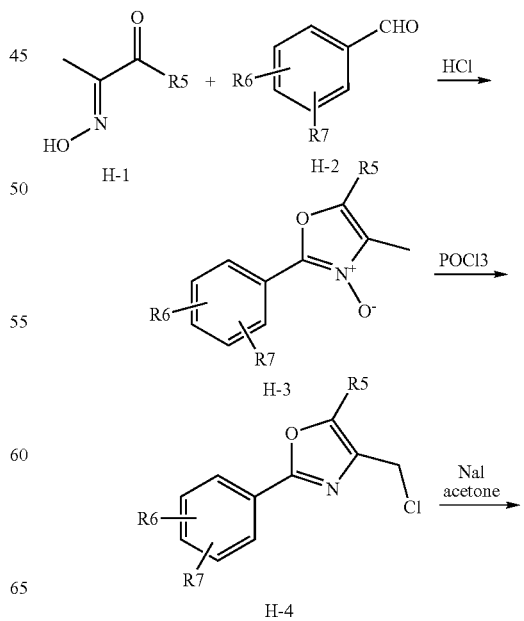

-continued

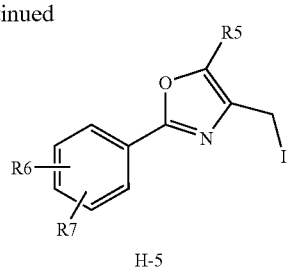

H-5

In ethanol and using hydrogen chloride, compound H-1 where R5 is as defined above is reacted with aldehyde H-2 in which R6 and R7 are as defined above, to give compound H-3.

Compound H-3 is heated to reflux in phosphoryl chloride, giving compound H-4. This is heated to reflux with sodium iodide in acetone. This gives compound H-5.

Other compounds can be obtained accordingly or by known processes.

Process I

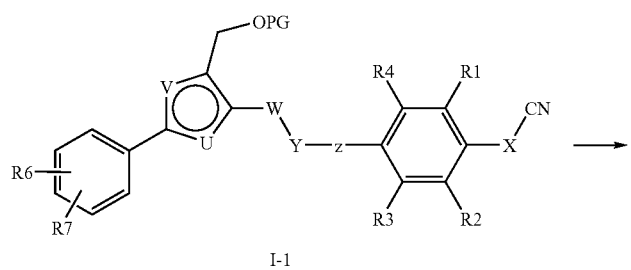

I-1

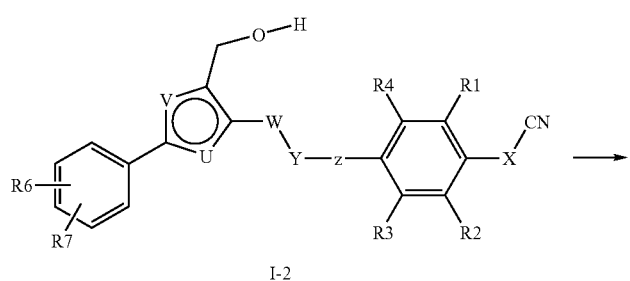

I-2

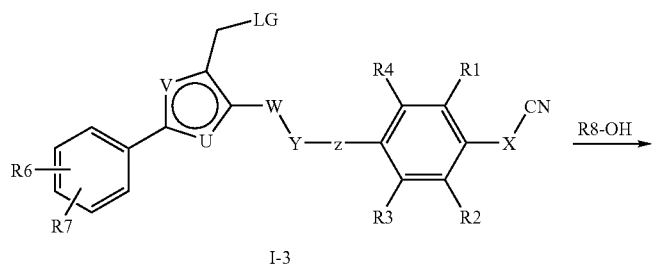

I-3

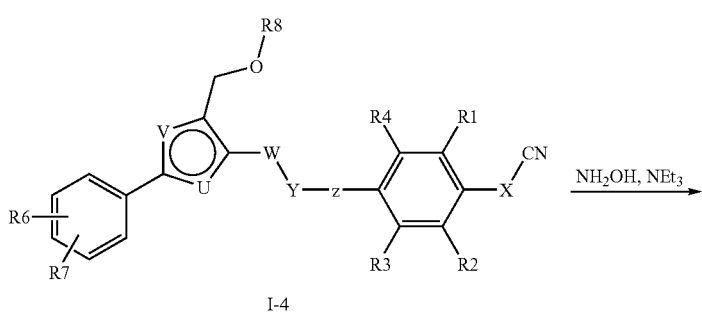

I-4

-continued

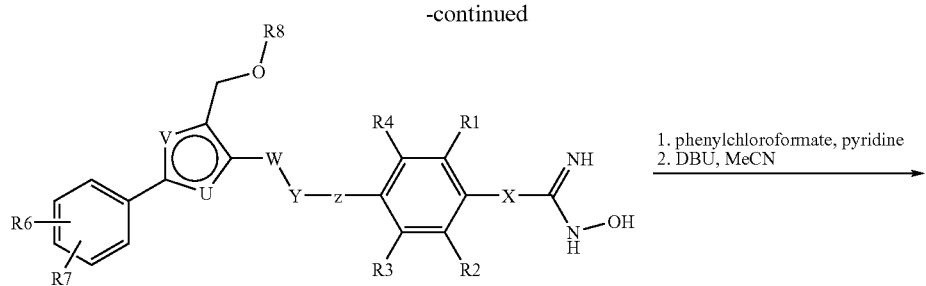

I-5

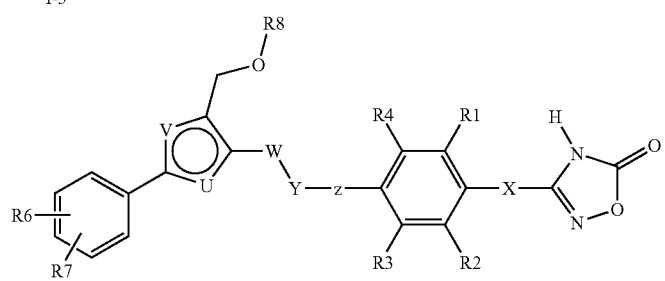

I-6

A compound of the general formula I-1 (which can be synthesized according to process A, B and D, where the substituent R5 of building blocks A-2, B-2 and D-2 is —CH2-OPG; synthesis of these building blocks is described in process J and K) where X, Y, Z, W R1, R2, R3, R4, R6 and R7 are as defined and PG means a protecting group as for example a tetrahydropyranylether. The protecting group of the compound of the general formula I-1 is removed, in case PG is a tetrahydropyranylether for example by treatment with an acid in polar solvent as methanol to obtain a compound of general formula I-2. The hydroxyl group of the compound of general formula I-2 is converted into a leaving group (LG) for example a mesylate by treatment with methanesulfonylchloride in the presence of a base as triethylamine in a solvent as dichloromethane to obtain a compound of general formula I-3. The compound of general formula I-3 is reacted with an alcohol in the presence of a base as sodium hydride to obtain a compound of general formula I-4, where the definition of —CH2-O—R8 is comprised in the definition of R5 as described. The compound of the general formula I-4 is reacted with hydroxylamine hydrochloride in the presence of a base as triethylamine in a solvent as tetrahydrofuran and methanol to obtain a compound of the general formula I-5. A compound of the general formula I-5 is converted to the product of general formula I-6 by reaction with phenylchloroformate in the presence of a base as pyridine and treating this intermediate with a base as 1,8-diazabicyclo[5.4.0]undec-7-ene in a solvent as acetonitrile.

Examples 33-36 were obtained according to process I.

Other compounds can be obtained accordingly or by known processes.

Process J:

This process is used for synthesizing the building blocks A-2, B-2 and D-2 where R5=—CH2-OPG (PG=protecting group), U is S or O, W=—CH$_2$, R=—OH or —Cl and R6 and R7 are as defined above.

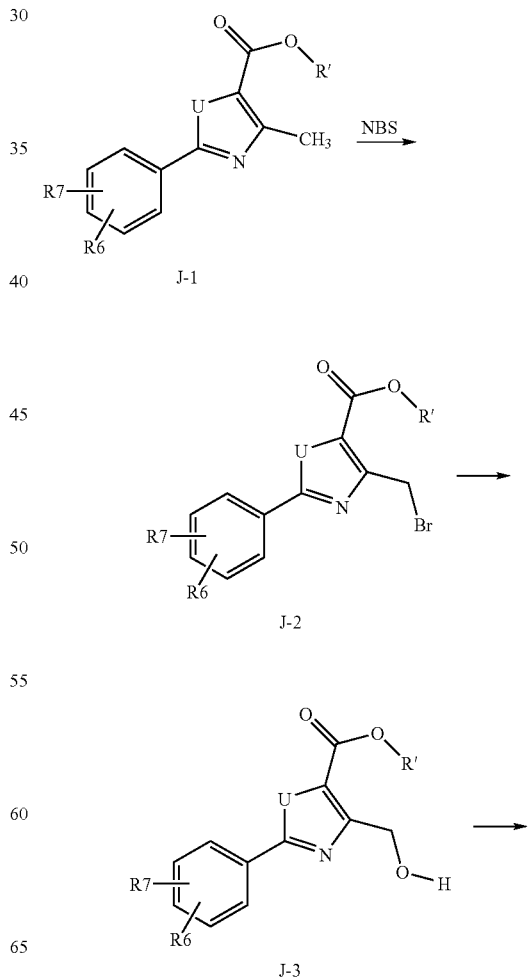

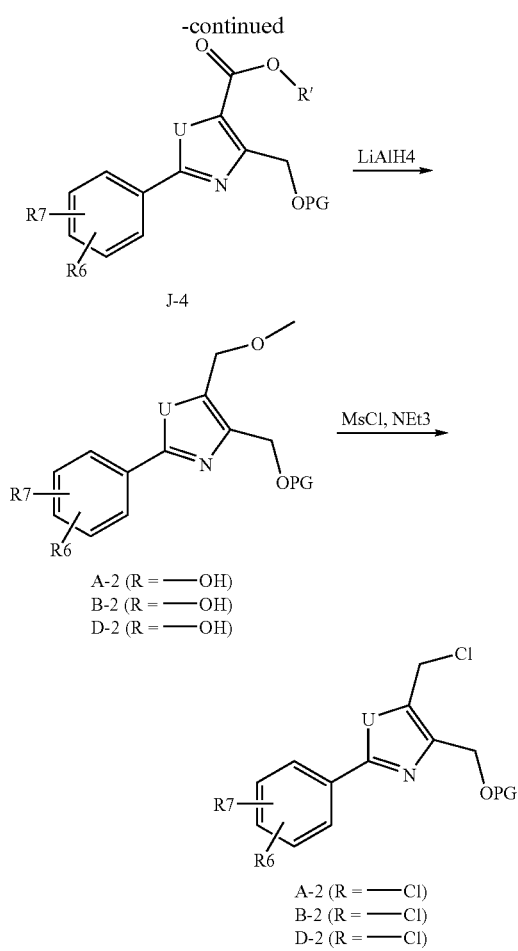

A compound of the general formula J-1 (which can be synthesized according to process F (J-1 is part of F-4)) where U is S or O, R' is alkyl as methyl or ethyl, and R6 and R7 are as defined above is brominated upon treatment with N-bromosuccinimide in an apolar solvent as tetrachloromethane to obtain a compound of general formula J-2. The bromide of general formula J-2 is converted into the alcohol of general formula J-3 upon treatment with silver trifluoroacetate in a solvent as dimethylformamide and subsequent heating of the resulting trifluoroacetate in a solvent as ethanol. The hydroxyl group of the compound of general formula J-2 is protected for example as a tetrahydropyranylether by treatment with 3,4-dihydro-2H-pyran in a solvent as dichloromethane in the presence of an acid as pyridinium para-toluenesulfonate to obtain a compound of general formula J-4. The ester of the compound of general formula J-4 is reduced with an agent as lithium aluminium hydride in a solvent as tetrahydrofuran to obtain the compound of general formula A-2, B-2 or D-2, where R is OH. The hydroxylic group can be converted into a chlorine by treatment with methanesulfonylchloride in the presence of a base as triethylamine in a solvent as dichloromethane to obtain a compound of general formula A-2, B-2 or D-2, where R is Cl.

Other compounds can be obtained accordingly or by known processes.

Process K:

This process is used for synthesizing the building blocks A-2, B-2 and D-2 where R5=—CH2-OPG (PG=protecting group), V is N and U is O, W=—CH2-, R=—OH or —Cl and R6 and R7 are as defined above.

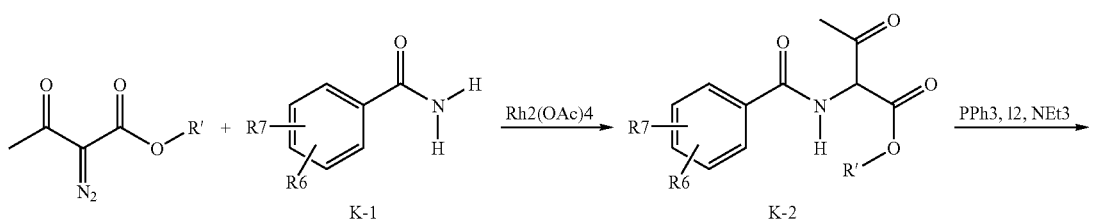

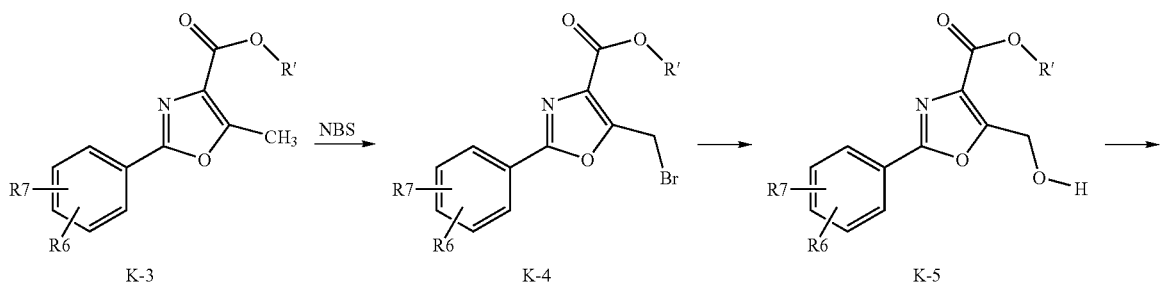

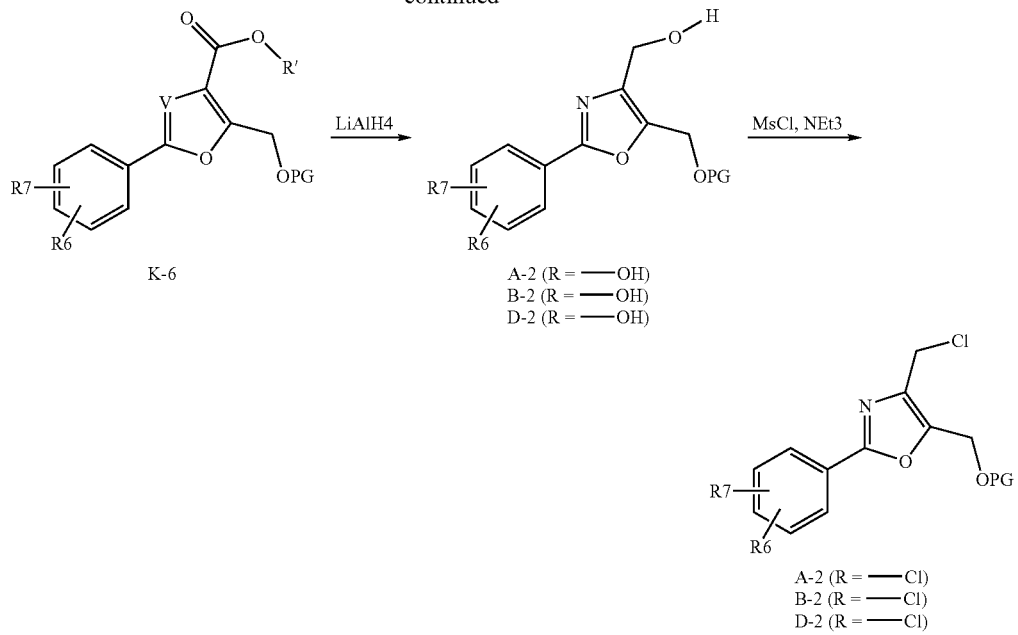

Methyl 2-diazo-3-oxobutanoate (R'=Me) or Ethyl-2-diazo-3-oxobutanoate (R'=Et) is reacted with a benzamide of general formula K-1, where R6 and R7 are as defined above in the presence of dirhodium tetraacetate in an apolar solvent as 1,2-dichloroethane to obtain a compound of general formula K-2. The compound of general formula K-2 is cyclized to obtain a compound of general formula K-3 upon treatment with triphenylphosphine and iodine in an apolar solvent as dichloromethane. The compound of the general formula K-3 is brominated upon treatment with N-bromosuccinimide in an apolar solvent as tetrachloromethane to obtain a compound of general formula K-4. The bromide of general formula K-4 is converted into the alcohol of general formula K-5 upon treatment with silver trifluoroacetate in a solvent as dimethylformamide and subsequent heating of the resulting trifluoroacetate in a solvent as ethanol. The hydroxyl group of the compound of general formula K-5 is protected for example as a tetrahydropyranylether by treatment with 3,4-dihydro-2H-pyran in a solvent as dichloromethane in the presence of an acid as pyridinium para-toluenesulfonate to obtain a compound of general formula K-6. The ester of the compound of general formula K-6 is reduced with a reducing agent as lithium aluminium hydride in a solvent as tetrahydrofuran to obtain the compound of general formula A-2, B-2 or D-2, where R is OH. The hydroxylic group can be converted into a chlorine by treatment with methanesulfonylchloride in the presence of a base as triethylamine in a solvent as dichloromethane to obtain a compound of general formula A-2, B-2 or D-2, where R is Cl.

LIST OF ABBREVIATION

Ac acetyl

Bn benzyl iBu isobutyl tBu tert-Butyl

BuLi n-butyllithium

Bz benzoyl

Cy cyclohexyl

DCI Direct chemical ionization (MS)

DCM dichloromethane

DMAP N,N-dimethylaminopyridine

DMF N,N-dimethylformamide

DMSO dimethylsulfoxide

EE ethyl acetate eq equivalents

ESI electronspray-Ionisation (MS)

FG Leaving group

Hal halogen

HPLC High performance liquid chromatography

LC-MS liquid chromatography coupled with mass-spectroscopy

LG Leaving Group

Me methyl

MS mass-spectroscopy

MsCl Methanesulfonylchloride

NBS N-bromosuccinimide

NMR Nuclear magnetic resonance p para

Pd/C palladium on carbon

PG Protecting Group iPr isopropyl nPr n-propyl

Rf retention time (TLC)

tert Tertiary

TLC Thin layer chromatography

Further compounds of the formula I can be prepared correspondingly or by known processes.

The experimental procedures for preparing the examples mentioned above are described below:

Building Block Synthesis According to Process F:

4-Butyl-5-chloromethyl-2-(4-trifluoromethyl-phenyl)-thiazole

4-Butyl-2-(4-trifluoromethyl-phenyl)-thiazol-5-carboxylic acid methyl ester

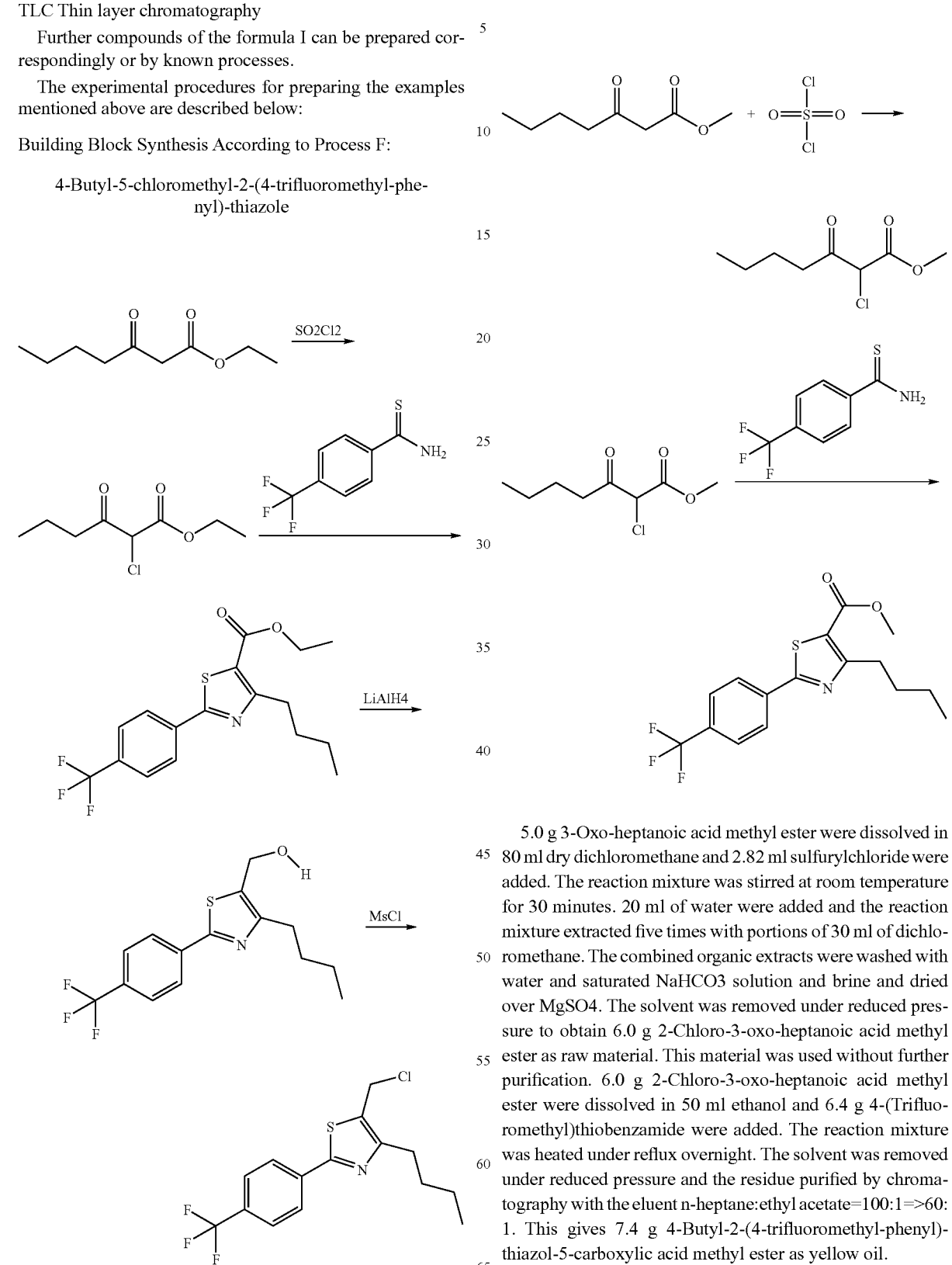

5.0 g 3-Oxo-heptanoic acid methyl ester were dissolved in 80 ml dry dichloromethane and 2.82 ml sulfurylchloride were added. The reaction mixture was stirred at room temperature for 30 minutes. 20 ml of water were added and the reaction mixture extracted five times with portions of 30 ml of dichloromethane. The combined organic extracts were washed with water and saturated NaHCO3 solution and brine and dried over MgSO4. The solvent was removed under reduced pressure to obtain 6.0 g 2-Chloro-3-oxo-heptanoic acid methyl ester as raw material. This material was used without further purification. 6.0 g 2-Chloro-3-oxo-heptanoic acid methyl ester were dissolved in 50 ml ethanol and 6.4 g 4-(Trifluoromethyl)thiobenzamide were added. The reaction mixture was heated under reflux overnight. The solvent was removed under reduced pressure and the residue purified by chromatography with the eluent n-heptane:ethyl acetate=100:1=>60:1. This gives 7.4 g 4-Butyl-2-(4-trifluoromethyl-phenyl)-thiazol-5-carboxylic acid methyl ester as yellow oil.

C16H16F3NO2S (343.37), MS (ESI): 344.1 (M+H$^+$), Rf (n-heptane:ethyl acetate=4:1)=0.62.

[4-Butyl-2-(4-trifluoromethyl-phenyl)-thiazole-5-yl]-methanol

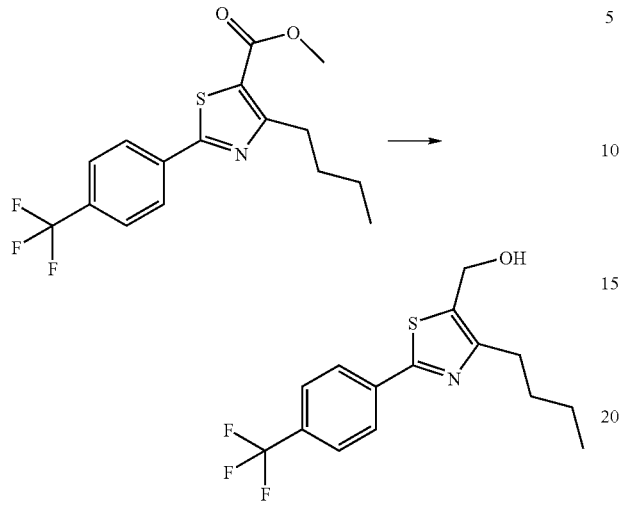

1.2 g lithium aluminium hydride was dissolved in 100 ml dry tetrahydrofuran. 5.3 g 4-Butyl-2-(4-trifluormethyl-phenyl)-thiazol-5-carboxylic acid methyl ester, dissolved in 100 ml tetrahydrofuran, were added. The reaction mixture was stirred at room temperature over a period of one hour, then 50 ml saturated ammonium chloride solution and 50 ml of a 1 molar hydrochloric acid solution were added. The reaction mixture was extracted five times with portions of 60 ml of ethyl acetate. The combined organic layers were dried over MgSO4 and the solvent removed under reduced pressure to provide 4.6 g [4-Butyl-2-(4-trifluoromethyl-phenyl)-thiazole-5-yl]-methanol as a yellow oil, which solidified upon standing at room temperature.

C15H16F3NOS (315.36), MS (ESI): 316.4 (M+H$^+$).

4-Butyl-5-chloromethyl-2-(4-trifluoromethyl-phenyl)-thiazole

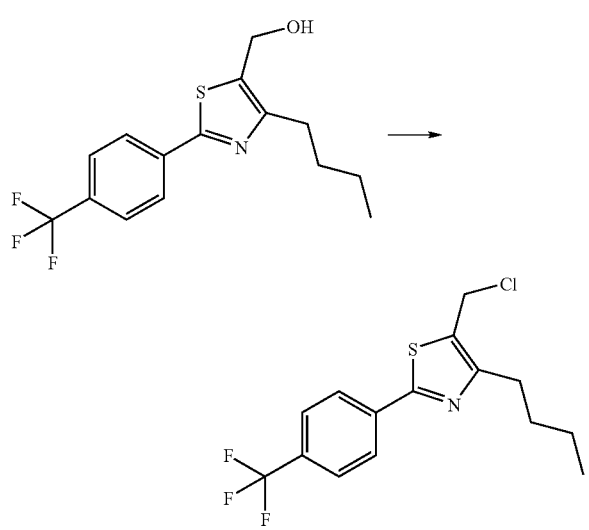

1.0 g [4-Butyl-2-(4-trifluoromethyl-phenyl)-thiazole-5-yl]-methanol were dissolved in 50 ml dichloromethane, 0.88 ml triethylamine and 0.39 ml methanesulfonyl chloride were added. The reaction mixture was stirred at room temperature for a period of three hours then 100 ml of dichloromethane were added and the reaction mixture washed with 50 ml of saturated NaHCO3 solution, water and brine. The organic layer was dried over MgSO4 and the solvent removed under reduced pressure. This provided 1.0 g 4-Butyl-5-chloromethyl-2-(4-trifluoromethyl-phenyl)-thiazole as yellow oil.

C15H15ClF3NS (333.81), MS (ESI): 334.3 (M+H$^+$).

[4-But-3-enyl-2-(4-trifluoromethyl-phenyl)-thiazol-5-yl]-methanol

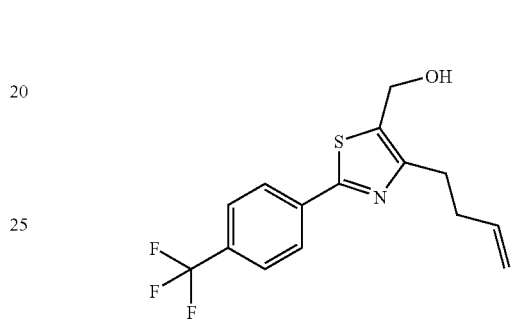

According to the method described for [4-butyl-2-(4-trifluoromethyl-phenyl)-thiazole-5-yl]-methanol, [4-but-3-enyl-2-(4-trifluoromethyl-phenyl)-thiazol-5-yl]-methanol was obtained from 3-oxo-hept-6-enoic acid ethyl ester and 4-(trifluoro)thiobenzamide.

C15H14F3NOS (313.34), MS (ESI): 312 (M−H$^+$).

[4-(3-Benzyloxy-propyl)-2-(4-trifluoromethyl-phenyl)-thiazol-5-yl]-methanol

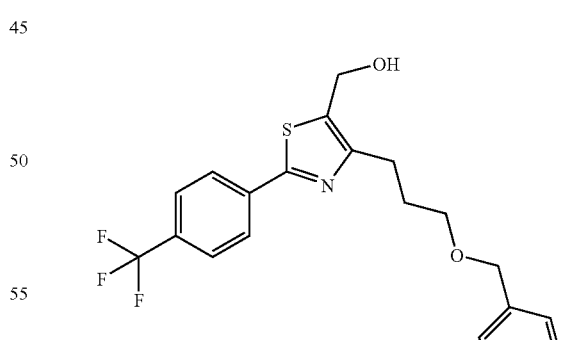

According to the method described for [4-butyl-2-(4-trifluoromethyl-phenyl)-thiazole-5-yl]-methanol, [4-(3-benzyloxy-propyl)-2-(4-trifluoromethyl-phenyl)-thiazol-5-yl]-methanol was obtained from the known 6-benzyloxy-3-oxo-hexanoic acid methyl ester and 4-(trifluoro)thiobenzamide.

C21H20F3NO2S (407.45), MS (ESI): 408 (M+H$^+$).

51

4-Butyl-5-chloromethyl-2-(4-pentafluorosulfanyl-phenyl)-thiazole

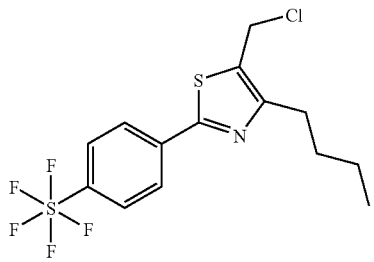

According to the method described for 4-butyl-5-chloromethyl-2-(4-trifluoromethyl-phenyl)-thiazole,4-butyl-5-chloromethyl-2-(4-pentafluorosulfanyl-phenyl)-thiazole was obtained from commercially available 3-Oxo-heptanoic acid methyl ester and 4-(pentafluorosulfanyl)thiobenzamide.

C14H15ClF5NS2 (391.86), MS (ESI): 392.3 (M+H$^+$).

5-Chloromethyl-4-methyl-2-(4-pentafluorosulfanyl-phenyl)-thiazole

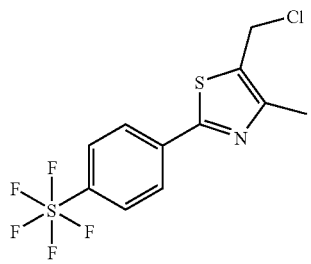

According to the method described for 4-butyl-5-chloromethyl-2-(4-trifluoromethyl-phenyl)-thiazole,5-chloromethyl-4-methyl-2-(4-pentafluorosulfanyl-phenyl)-thiazole was obtained from commercially available Ethyl 2-Chloroacetoacetate and 4-(pentafluorosulfanyl)thiobenzamide.

C11H9ClF5NS2 (349.77), MS (ESI): 350.4 (M+H$^+$).

2-(4-Methoxy-phenyl)-4-methyl-oxazole-5-carboxylic acid ethyl ester

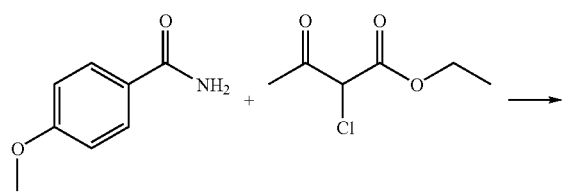

52

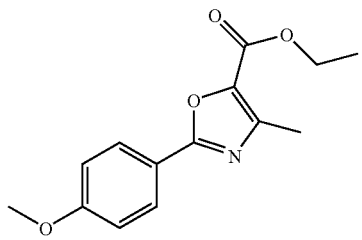

40.0 g 4-Methoxybenzamide was dissolved in 400 ml ethanol. The mixture was warmed to 50° C. and 48.8 ml ethyl-2-chloroacetoacetate was added in one portion. The resulting mixture was refluxed for four days. The reaction mixture was cooled and the solvent removed under reduced pressure. The resulting residue was purified by flash chromatography on silica gel to obtain 23.5 g 2-(4-Methoxy-phenyl)-4-methyl-oxazole-5-carboxylic acid ethyl ester as a solid.

C14H15NO4 (261.28), MS (ESI): 262.1 (M+H$^+$).

Building Block Synthesis According to Process E:

2-[4-Butyl-2-(4-trifluoromethyl-phenyl)-thiazol-5-yl]-ethanol

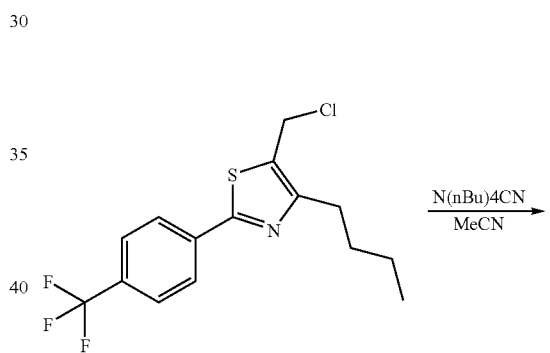

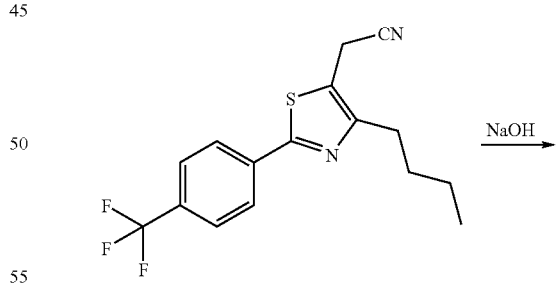

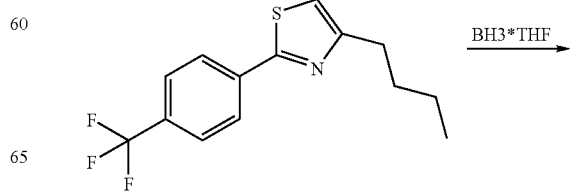

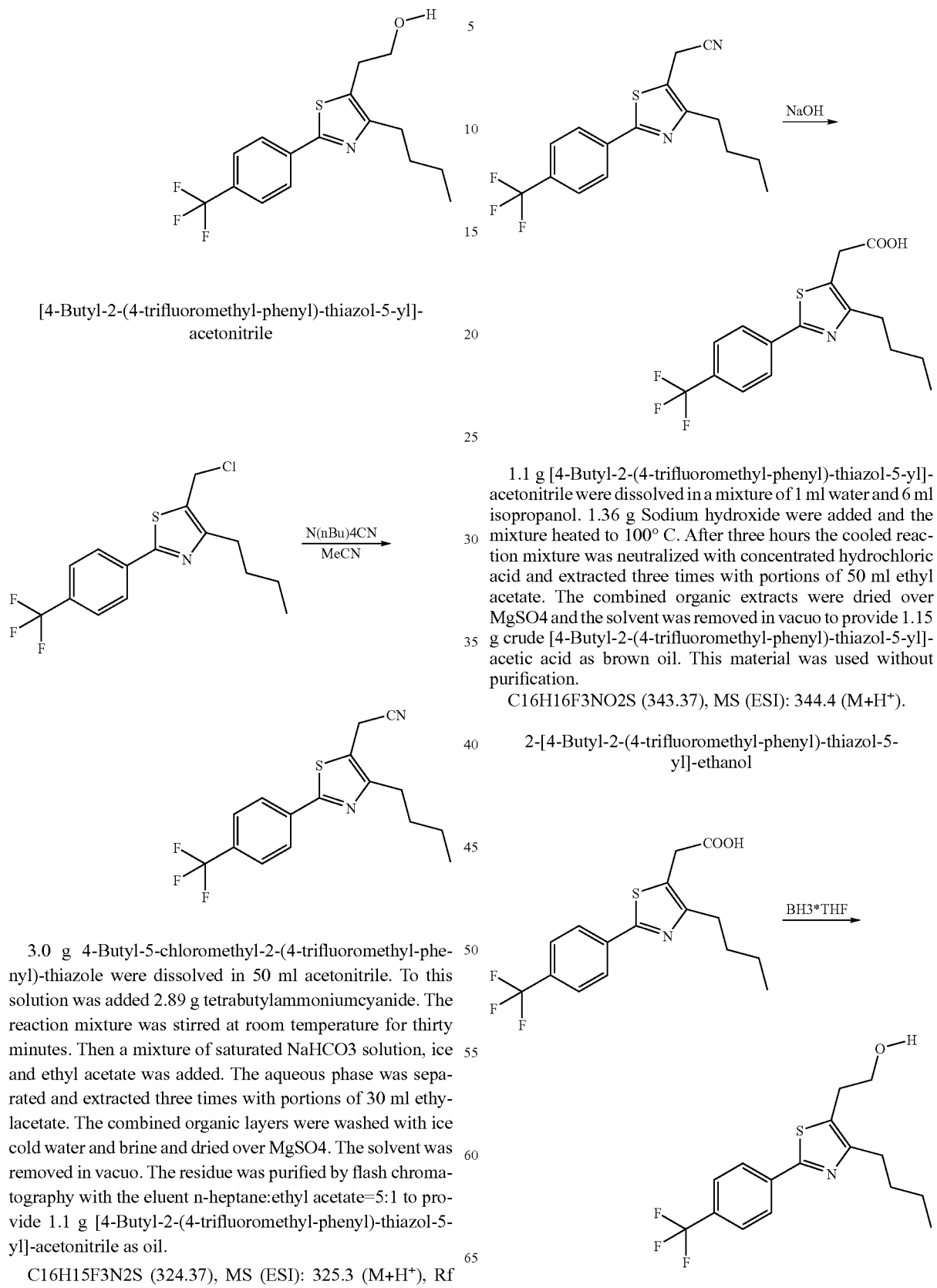

[4-Butyl-2-(4-trifluoromethyl-phenyl)-thiazol-5-yl]-acetonitrile 3.0 g 4-Butyl-5-chloromethyl-2-(4-trifluoromethyl-phenyl)-thiazole were dissolved in 50 ml acetonitrile. To this solution was added 2.89 g tetrabutylammoniumcyanide. The reaction mixture was stirred at room temperature for thirty minutes. Then a mixture of saturated NaHCO3 solution, ice and ethyl acetate was added. The aqueous phase was separated and extracted three times with portions of 30 ml ethylacetate. The combined organic layers were washed with ice cold water and brine and dried over MgSO4. The solvent was removed in vacuo. The residue was purified by flash chromatography with the eluent n-heptane:ethyl acetate=5:1 to provide 1.1 g [4-Butyl-2-(4-trifluoromethyl-phenyl)-thiazol-5-yl]-acetonitrile as oil.

C16H15F3N2S (324.37), MS (ESI): 325.3 (M+H$^+$), Rf (n-heptane:ethyl acetate=4:1)=0.32.

[4-Butyl-2-(4-trifluoromethyl-phenyl)-thiazol-5-yl]-acetic acid 1.1 g [4-Butyl-2-(4-trifluoromethyl-phenyl)-thiazol-5-yl]-acetonitrile were dissolved in a mixture of 1 ml water and 6 ml isopropanol. 1.36 g Sodium hydroxide were added and the mixture heated to 100° C. After three hours the cooled reaction mixture was neutralized with concentrated hydrochloric acid and extracted three times with portions of 50 ml ethyl acetate. The combined organic extracts were dried over MgSO4 and the solvent was removed in vacuo to provide 1.15 g crude [4-Butyl-2-(4-trifluoromethyl-phenyl)-thiazol-5-yl]-acetic acid as brown oil. This material was used without purification.

C16H16F3NO2S (343.37), MS (ESI): 344.4 (M+H$^+$).

2-[4-Butyl-2-(4-trifluoromethyl-phenyl)-thiazol-5-yl]-ethanol 1.15 g crude [4-Butyl-2-(4-trifluoromethyl-phenyl)-thiazol-5-yl]-acetic acid were dissolved in 50 ml tetrahydrofuran and cooled in an ice bath to 0° C. At 0° C. 9.3 ml 1 M solution of borane tetrahydrofuran complex were added. The reaction mixture was warmed to 55° C. and stirred for one hour at this temperature. The reaction mixture was cooled in an ice bath and 50 ml water was added. The organic layer was added. The tetrahydrofuran was removed in vacuo and the residue extracted three times with portions of 80 ml ethyl acetate. The combined organic layers were washed with brine, dried over MgSO4 and the solvent removed in vacuo to provide 1.1 g crude 2-[4-Butyl-2-(4-trifluoromethyl-phenyl)-thiazol-5-yl]-ethanol as brown oil. This material was used without purification.

C16H18F3NOS (329.39), MS (ESI): 330.4 (M+H$^+$).

Building Block Synthesis According to Process G:

2-[5-Methyl-2-(4-pentafluorosulfanyl-phenyl)-thiazol-4-yl]-ethanol

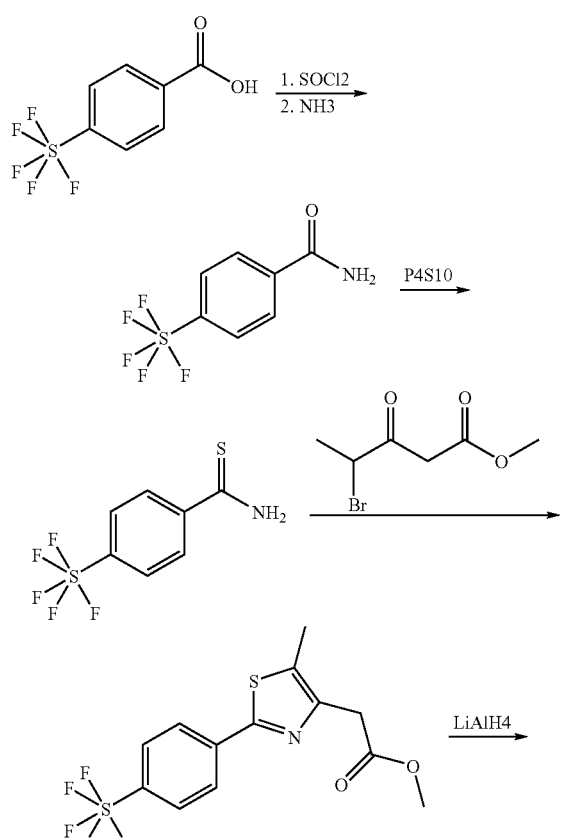

4-Pentafluorosulfanyl-benzamide

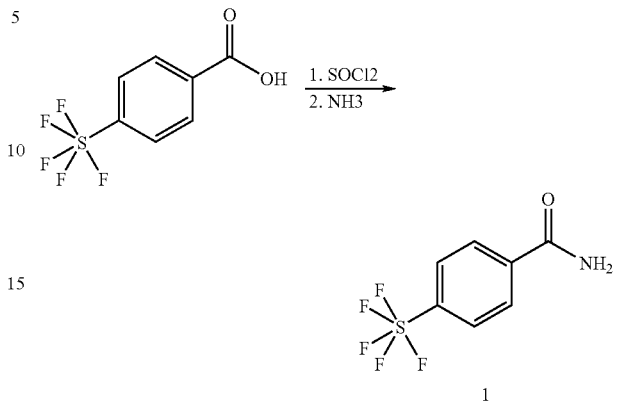

20 g 4-Pentafluorosulfanyl-benzoic acid were refluxed in 300 ml thionyl chloride for three hours. The thionylchloride was removed under reduced pressure, the resulting residue was dissolved in 100 ml tetrahydrofuran. This solution was added dropwise to 80 ml of a concentrated ammonia solution. The solvent was removed in vacuo and resulting residue was dissolved in 300 ml water and extracted three times with portions of 250 ml ethyl acetate. The combined organic layers were dried over MgSO4 and the solvent was removed in vacuo to provide 24.5 g 4-Pentafluorosulfanyl-benzamide as a yellow solid. This material was used without purification.

C7H6F5NOS (247.19), MS (ESI): 248 (M+H$^+$).

4-Pentafluorosulfanyl-thiobenzamide

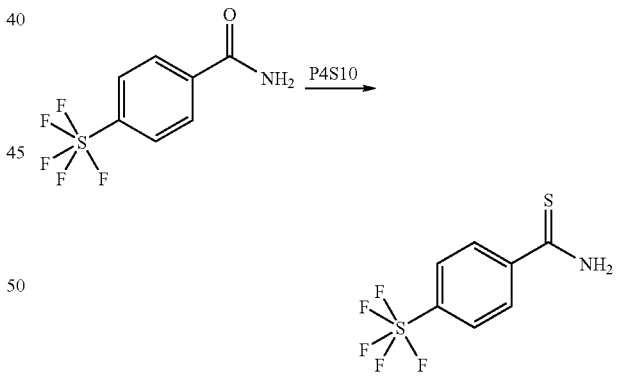

9 g Phosphorpentasulfide were dissolved in 300 ml toluene. 16.8 g NaHCO3 were added and the mixture refluxed for thirty minutes. Then 25.2 g 4-pentafluorosulfanyl-benzamide, dissolved in 200 ml toluene, were added and the reaction mixture was stirred at 90° C. for three hours. The solvent was removed in vacuo and the resulting residue was dissolved in 300 ml brine and extracted three times with portions of 250 ml dichlormethane. The combined organic layers were dried over MgSO4 and the solvent was removed in vacuo to provide 17.4 g 4-pentafluorosulfanyl-thiobenzamide as a yellow solid.

C7H6F5NS2 (263.25), MS (ESI): 264 (M+H$^+$).

[5-Methyl-2-(4-pentafluorosulfanyl-phenyl)-thiazol-4-yl]-acetic acid ethyl ester

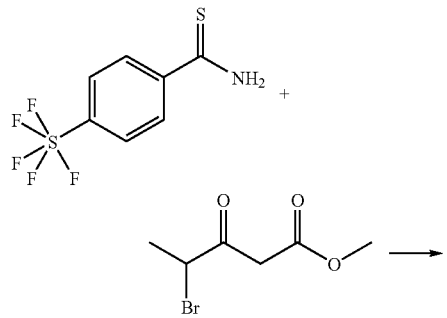

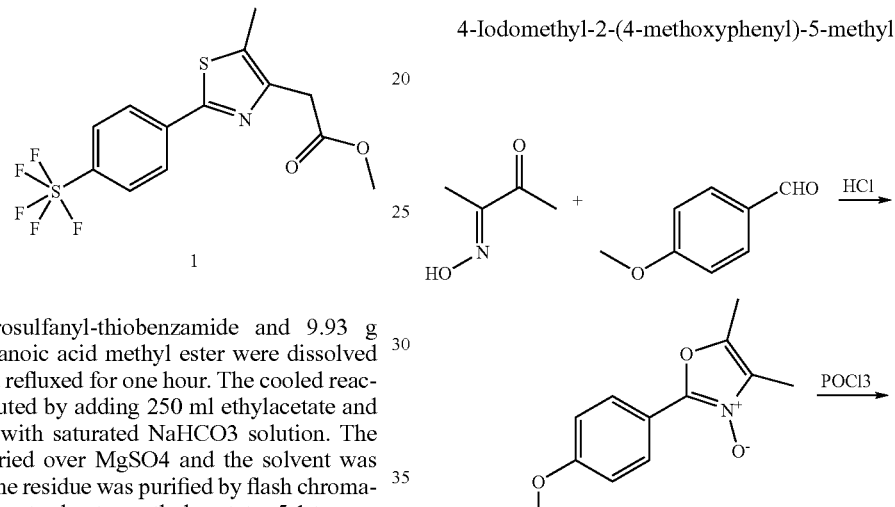

0 g 4-Pentafluorosulfanyl-thiobenzamide and 9.93 g 4-bromo-3-oxo-pentanoic acid methyl ester were dissolved in 30 ml acetone and refluxed for one hour. The cooled reaction mixture was diluted by adding 250 ml ethylacetate and washed three times with saturated NaHCO3 solution. The organic layer was dried over MgSO4 and the solvent was removed in vacuo. The residue was purified by flash chromatography with the eluent n-heptane:ethyl acetate=5:1 to provide 4.5 g [5-Methyl-2-(4-pentafluorosulfanyl-phenyl)-thiazol-4-yl]-acetic acid ethyl ester as an oil which solidified upon standing.

C13H12F5NO2S2 (373.37), MS (ESI): 374 (M+H$^+$).

2-[5-Methyl-2-(4-pentafluorosulfanyl-phenyl)-thiazol-4-yl]-ethanol 458 mg Lithium aluminium hydride were suspended in 100 ml dry tetrahydrofuran and cooled in an ice bath. To this ice cooled suspension were added 4.5 g [5-Methyl-2-(4-pentafluorosulfanyl-phenyl)-thiazol-4-yl]-acetic acid ethyl ester, dissolved in 50 ml tetrahydrofuran. The reaction mixture was stirred for one hour. Then 300 ml ethyl acetate and 20 ml saturated NH4Cl solution were added. The organic layer was separated. The aqueous phase was extracted three times with portions of 50 ml ethyl acetate. The combined organic layers were dried over MgSO4 and the solvent was removed in vacuo. The residue was purified by flash chromatography with the eluent n-heptane:ethyl acetate=2:1 to provide 1.44 g 2-[5-methyl-2-(4-pentafluorosulfanyl-phenyl)-thiazol-4-yl]-ethanol as an oil which solidified upon standing.

C12H12F5NOS2 (345.36), MS (ESI): 346 (M+H$^+$).

Building Block Synthesis According to Process H:

4-Iodomethyl-2-(4-methoxyphenyl)-5-methyloxazole

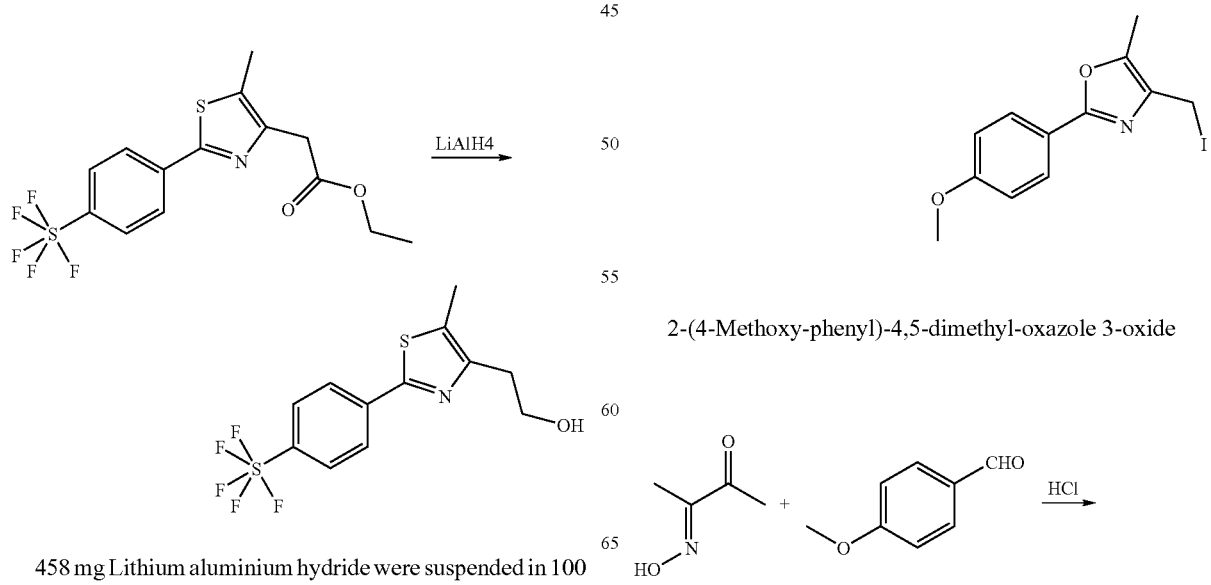

2-(4-Methoxy-phenyl)-4,5-dimethyl-oxazole 3-oxide

C12H12ClNO2 (237.69), MS (ESI)=238 (M+H⁺), Rf (n-heptane:ethyl acetate)=7:3)=0.45.

4-Iodomethyl-2-(4-methoxyphenyl)-5-methyloxazole

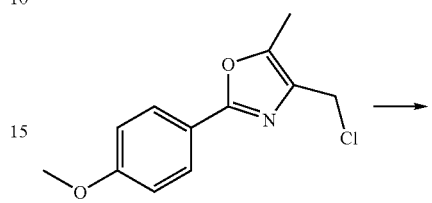

-continued

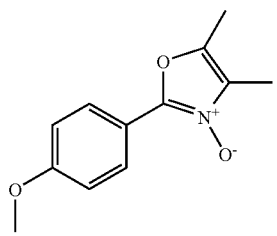

50.6 g of Diacetylmonoxime and 66.7 ml of 4-methoxybenzaldehyde are added to 100 ml of glacial acetic acid, and HCl gas is introduced for 30 minutes, with ice-cooling. The product is precipitated as the hydrochloride by addition of methyl tert-butyl ether and filtered off with suction, and the precipitate is washed with methyl tert-butyl ether. The precipitate is suspended in water and the pH is made alkaline using ammonia. The mixture is extracted three times with in each case 200 ml of dichloromethane, the combined organic phases are dried over MgSO4 and the solvent is then removed under reduced pressure. This gives 82.1 g of 2-(4-methoxyphenyl)-4,5-dimethyl-oxazole 3-oxide as a white solid. C12H13NO3 (219.24), MS (ESI)=220 (M+H⁺).

4-Chloromethyl-2-(4-methoxy-phenyl)-5-methyl-oxazole

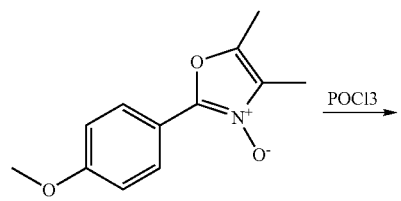

Together with 37.7 g of sodium iodide, 19.9 g of 4-chloromethyl-2-(4-methoxy-phenyl)-5-methyl-oxazole are, in 300 ml of acetone, heated at the boil under reflux for 2 hours. After cooling of the reaction mixture, the solvent was removed under reduced pressure and the residue dissolved in 300 ml of methyl tert-butyl ether, the mixture is washed three times with saturated Na2S2O3 solution and dried over MgSO4, and the solvent is then removed under reduced pressure. This gives 49.8 g of 4-Iodomethyl-2-(4-methoxyphenyl)-5-methyloxazole as a light-brown solid.

C12H12INO2 (329.14), MS (ESI): 330 (M+H⁺).

4-Iodomethyl-5-methyl-2-p-biphenyloxazole

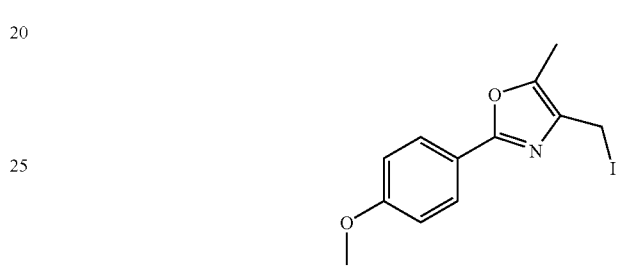

82 g of 2-(4-Methoxy-phenyl)-4,5-dimethyl-oxazole 3-oxide are dissolved in 400 ml of chloroform, 37.4 ml of phosphorus oxychloride are added and the mixture is, under reflux, heated at the boil for 30 minutes. The reaction mixture is cooled to 0° C., the pH is made slightly alkaline using ammonia and the mixture is extracted three times with in each case 100 ml of ethyl acetate. The combined organic phases are washed with water and dried over MgSO4, and the solvent then removed under reduced pressure. The residue is purified on silica gel using the mobile phase n-heptane:ethyl acetate=80:1=>5:1. This gives 46.3 g of 4-chloromethyl-2-(4-methoxy-phenyl)-5-methyl-oxazole as a yellow solid.

Analogously to the building block synthesis of 4-Iodomethyl-2-(4-methoxyphenyl)-5-methyloxazole, diacetylmonoxime and p-biphenylcarbaldehyde gave 4-iodomethyl-5-methyl-2-p-biphenyloxazole.

C12H12INO (375.21), MS (ESI): 376 (M+H⁺).

Building Block Synthesis According to Process J:

[2-(4-Methoxy-phenyl)-4-(tetrahydro-pyran-2-yloxymethyl)-oxazol-5-yl]-methanol and 5-chloromethyl-2-(4-methoxy-phenyl)-4-(tetrahydro-pyran-2-yloxymethyl)-oxazole

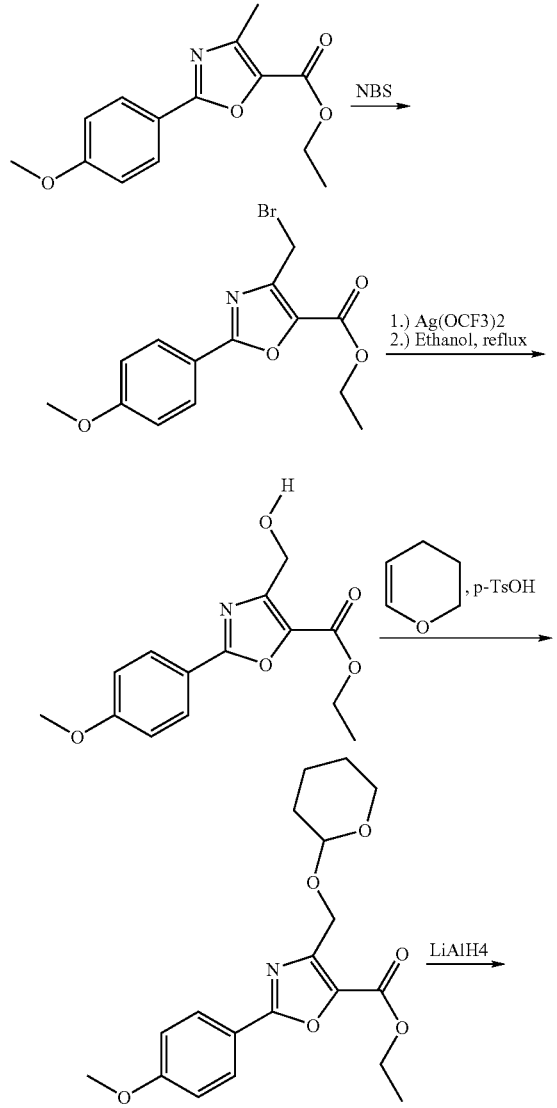

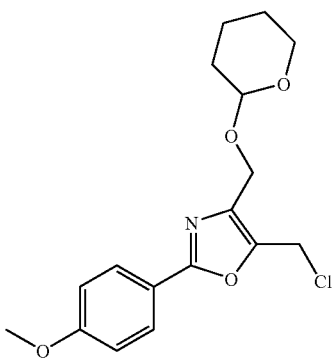

4-Bromomethyl-2-(4-methoxy-phenyl)-oxazole-5-carboxylic acid ethyl ester

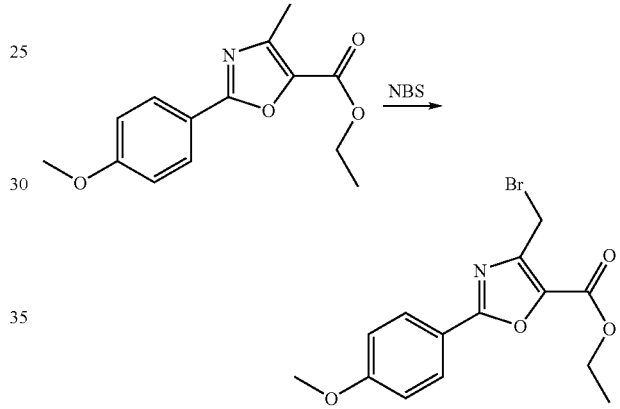

To a boiling solution of 23.5 g 2-(4-methoxy-phenyl)-4-methyl-oxazole-5-carboxylic acid ethyl ester in 250 ml tetrachloro-methane were added portionwise a mixture of 5.92 g 2,2'-azobis(2-methylpropionitrile) and 19.3 g N-bromosuccinimide. The reaction mixture was refluxed for seven hours. The cooled reaction mixture was filtered over a celite pad and the solvent removed in vacuo to obtain 30.7 g of crude 4-bromomethyl-2-(4-methoxy-phenyl)-oxazole-5-carboxylic acid ethyl ester. The material was used without further purification in the next step.

C14H14BrNO4 (340.18), MS (ESI): 340.0 and 342.0 (M+H$^+$), Rf (ethyl acetate:n-heptane=7:3)=0.43).

4-Hydroxymethyl-2-(4-methoxy-phenyl)-oxazole-5-carboxylic acid ethyl ester

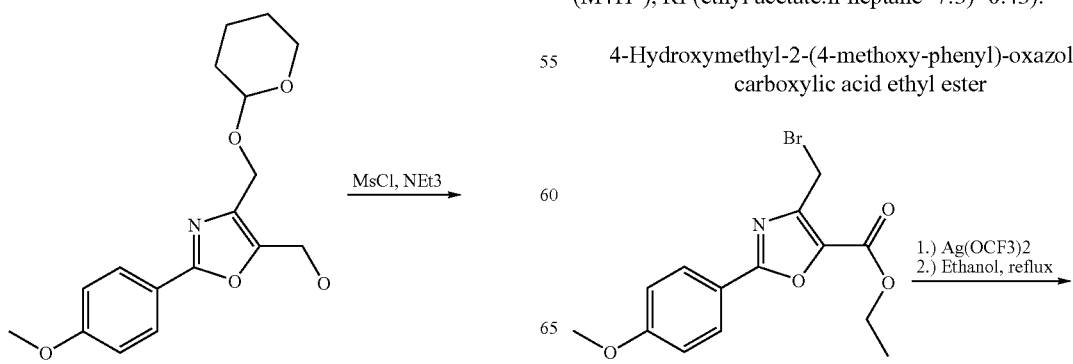

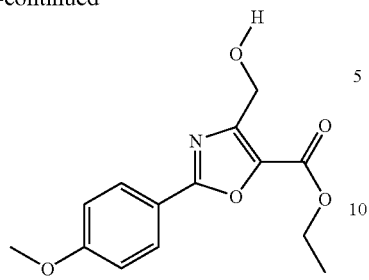

30.7 g of crude 4-Bromomethyl-2-(4-methoxy-phenyl)-oxazole-5-carboxylic acid ethyl ester were dissolved in 170 ml dry dimethylformamide. 29.95 g Silver trifluoroacetate were added and the mixture was stirred at room temperature overnight. 100 ml brine were added and the mixture was stirred for one hour. The reaction mixture was filtered through a pad of celite, the solvent removed in vacuo and the resulting residue dissolved in 200 ml ethanol. The mixture was heated to reflux for three hours. Then the solvent was removed in vacuo and the residue dissolved in water and extracted five times with ethyl acetate. The combined organic layers were dried over MgSO4, the solvent removed in vacuo and the residue purified by flash chromatography on silica gel (eluting with 1 n-heptane:ethyl acetate=5:1=>ethylacetate) to obtain 17.8 g 4-Hydroxymethyl-2-(4-methoxy-phenyl)-oxazole-5-carboxylic acid ethyl ester as a solid.

C4H15NO5 (277.28), MS (ESI): 278.1 (M+H$^+$), Rf (ethyl acetate:n-heptane=1:2)=0.11).

2-(4-Methoxy-phenyl)-4-(tetrahydro-pyran-2-yloxymethyl)-oxazole-5-carboxylic acid ethyl ester

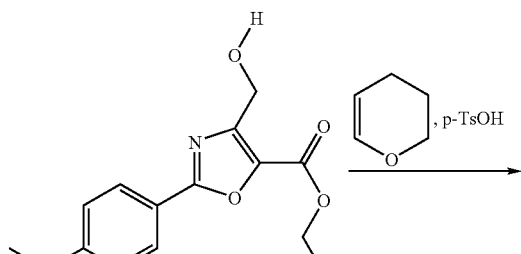

10.0 g 4-Hydroxymethyl-2-(4-methoxy-phenyl)-oxazole-5-carboxylic acid ethyl ester were dissolved in 85 ml dichloromethane. 4.0 ml 3,4-dihydro-2H-pyran and 1.85 mg pyridinium p-toluenesulfonate were added and the reaction mixture stirred at room temperature overnight. The solvent was removed in vacuo and the residue purified by flash chromatography on silica gel (eluting with n-heptane:ethyl acetate=4:1=>1:1) to obtain 12.3 g 2-(4-Methoxy-phenyl)-4-(tetrahydro-pyran-2-yloxymethyl)-oxazole-5-carboxylic acid ethyl ester as an oil.

C19H23NO6 (361.40), MS (ESI): 362.2 (M+H$^+$), 278.2 (M−THP+H+), Rf (ethyl acetate:n-heptane=1:1)=0.56).

[2-(4-Methoxy-phenyl)-4-(tetrahydro-pyran-2-yloxymethyl)-oxazol-5-yl]-methanol

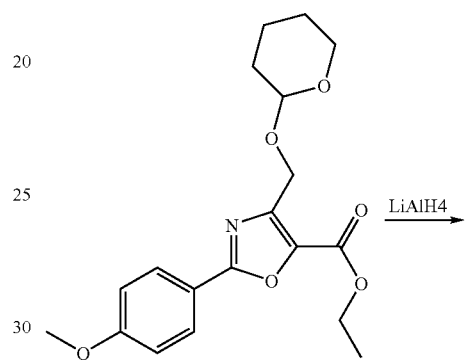

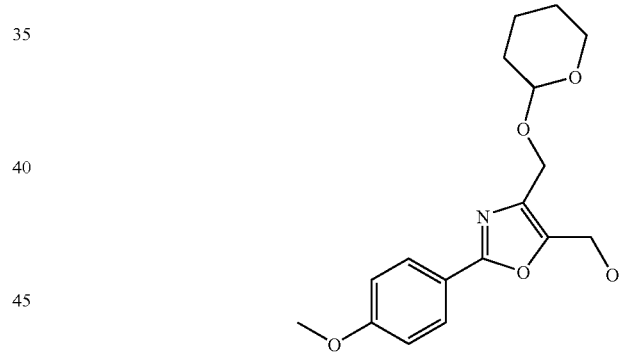

To a cooled suspension of 2.73 g lithium aluminium hydride in 180 ml tetrahydrofuran a solution of 12.3 g 2-(4-methoxy-phenyl)-4-(tetrahydro-pyran-2-yloxymethyl)-oxazole-5-carboxylic acid ethyl ester in 120 ml tetrahydrofuran were added at 0° C. The ice bath was removed and the reaction mixture stirred at room temperature for one hour. The reaction mixture was cooled in an ice bath again and 100 ml ethyl acetate were added followed by the addition of 300 ml methyl-tert.-butyl ether. Then a solution of 10.92 g sodium hydroxide in 12.3 ml water was added. Solid precipitates was filtered off through a plug of celite. The filtrate was dried over MgSO4 and then the solvent was removed in vacuo to obtain 11.8 g [2-(4-methoxy-phenyl)-4-(tetrahydro-pyran-2-yloxymethyl)-oxazol-5-yl]-methanol as a solid.

C17H21NO5 (319.36), MS (ESI): 320.2 (M+H$^+$), Rf (ethyl acetate:n-heptane=1:1)=0.18).

5-Chloromethyl-2-(4-methoxy-phenyl)-4-(tetrahydro-pyran-2-yloxymethyl)-oxazole

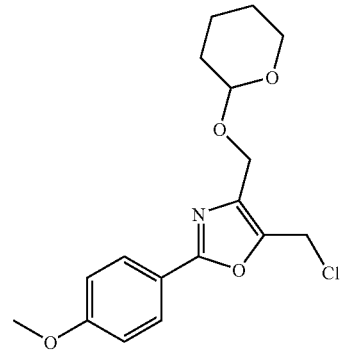

2.0 g [2-(4-Methoxy-phenyl)-4-(tetrahydro-pyran-2-yloxymethyl)-oxazol-5-yl]-methanol were dissolved in 30 ml dichloromethane and cooled in an ice bath. 0.88 ml triethylamine were added, followed by the addition of 0.49 ml methanesulfonylchloride. The ice bath was removed and the resulting mixture stirred at room temperature over night. The reaction mixture was then washed with water and brine, dried over MgSO4 and the solvent removed in vacuo to obtain 2.5 g of 5-chloromethyl-2-(4-methoxy-phenyl)-4-(tetrahydro-pyran-2-yloxymethyl)-oxazole as an oil which was used without further purification.

C17H20ClNO4 (337.81), MS (ESI): 338.2 (M+H$^+$), Rf (ethyl acetate:n-heptane=1:1)=0.42).

Building Block Synthesis According to Process K:

[2-(4-Methoxy-phenyl)-5-(tetrahydro-pyran-2-yloxymethyl)-oxazol-4-yl]-methanol and methanesulfonic acid 2-(4-methoxy-phenyl)-5-(tetrahydro-pyran-2-yloxymethyl)-oxazol-4-ylmethyl ester

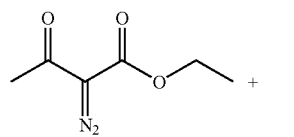

+

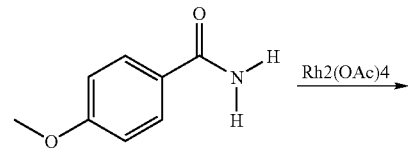

PPh3, I2, NEt3 →

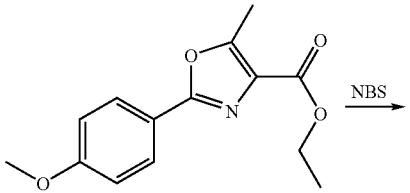

NBS →

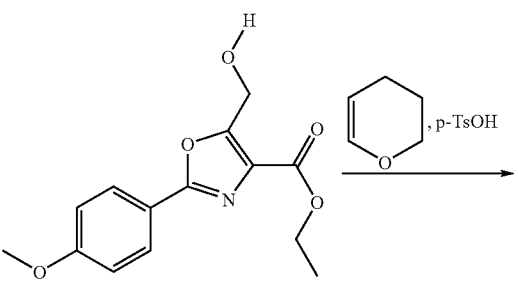

1.) Ag(OCF3)2
2.) Ethanol, reflux →

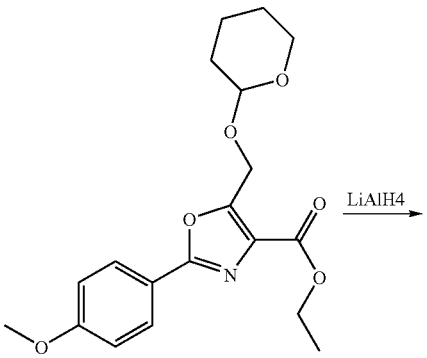

, p-TsOH →

-continued

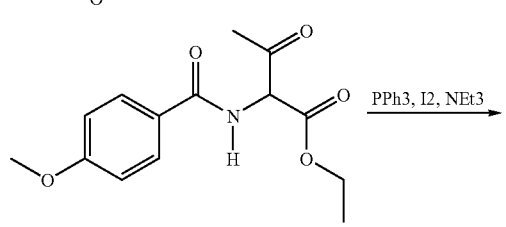

LiAlH4 →

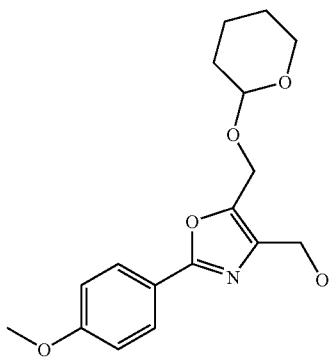

MsCl, NEt3 →

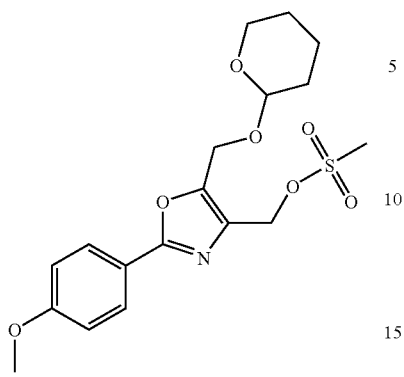

2-(4-Methoxy-benzoylamino)-3-oxo-butyric acid ethyl ester

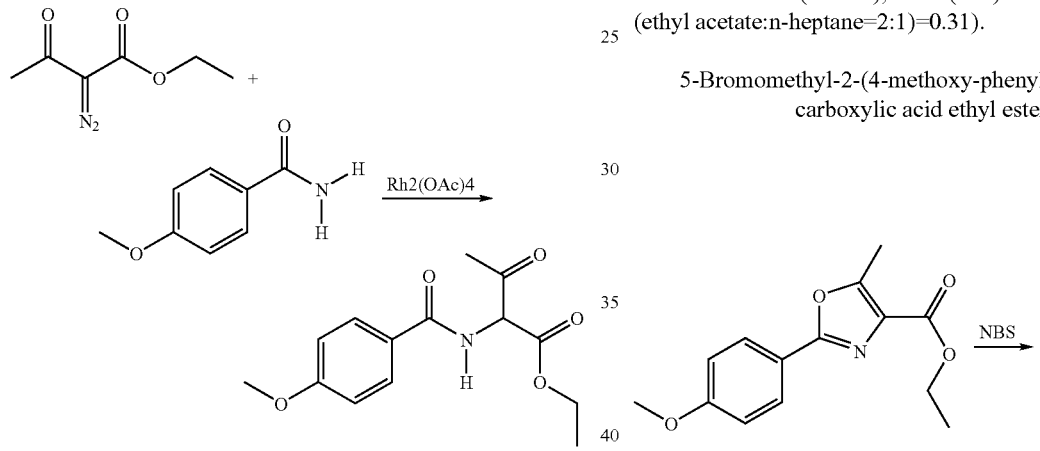

A solution of 12.1 g ethyl-2-diazo-3-oxobutanoate[2] in 100 ml 1,2-dichloroethane was added dropwise over 5 hours to a boiling solution of 9.0 g 4-methoxybenzamide and 1.05 g rhodium(II) acetate dimer in 200 ml dry 1,2-dichloroethane. The mixture was refluxed for thirty minutes, allowed to cool, evaporated in vacuo and purified by flash chromatography on silica gel to obtain 11.3 g 2-(4-Methoxy-benzoylamino)-3-oxo-butyric acid ethyl ester.

[2] J. Chem. Soc., Perkin Trans. 1, 1998, 591-600.

C14H17NO5 (279.30), MS (ESI): 280.2 (M+H$^+$), Rf (ethyl acetate:n-heptane=1:1)=0.32).

2-(4-Methoxy-phenyl)-5-methyl-oxazole-4-carboxylic acid ethyl ester

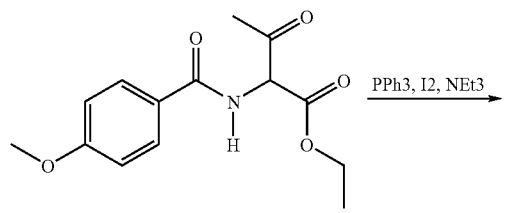

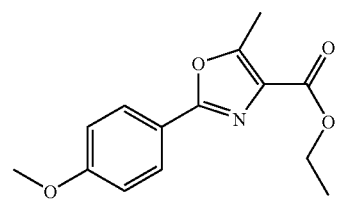

23.2 ml Triethylamine and a solution of 11.3 g 2-(4-methoxy-benzoylamino)-3-oxo-butyric acid ethyl ester in 200 ml dichloromethane were added sequentially to a stirred solution of 20.5 g iodine and 21.2 g triphenylphosphine in 500 ml dry dichloromethane. The reaction mixture was stirred at room temperature overnight. The solvent was evaporated in vacuo and the resulting residue purified by flash chromatography on silica gel to obtain 6.0 g 2-(4-methoxy-phenyl)-5-methyl-oxazole-4-carboxylic acid ethyl ester as pale yellow solid.

C14H15NO4 (261.28), MS (ESI): 262.2 (M+H$^+$), Rf (ethyl acetate:n-heptane=2:1)=0.31).

5-Bromomethyl-2-(4-methoxy-phenyl)-oxazole-4-carboxylic acid ethyl ester

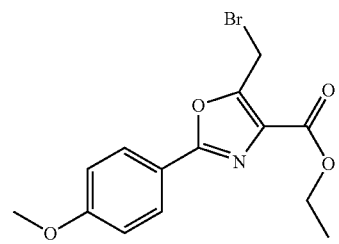

To a boiling solution of 6.0 g 2-(4-methoxy-phenyl)-5-methyl-oxazole-4-carboxylic acid ethyl ester in 100 ml tetrachloro-methane were added portionwise a mixture of 1.51 g 2,2'-azobis(2-methylpropionitrile) and 4.9 g N-bromosuccinimide. The reaction mixture was refluxed for three hours. The cooled reaction mixture was filtered over a celite pad and the solvent removed in vacuo to obtain 10.6 g of crude 5-bromomethyl-2-(4-methoxy-phenyl)-oxazole-4-carboxylic acid ethyl ester, which contains to some extend the dibrominated byproduct. The material was used without further purification in the next step.

C14H14BrNO4 (340.18), MS (ESI): 340.0 and 342.0 (M+H$^+$), Rf (ethyl acetate:n-heptane=2:1)=0.27).

5-Hydroxymethyl-2-(4-methoxy-phenyl)-oxazole-4-carboxylic acid ethyl ester

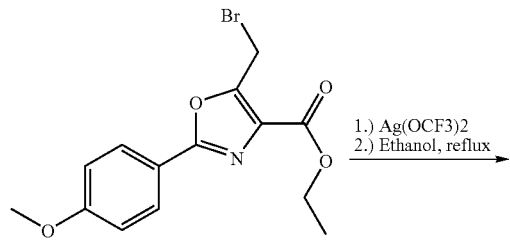

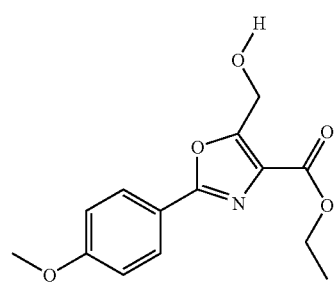

8.0 g 5-Bromomethyl-2-(4-methoxy-phenyl)-oxazole-4-carboxylic acid ethyl ester were dissolved in 50 ml dry dimethylformamide. 7.8 g Silver trifluoroacetate were added and the mixture was stirred at room temperature for two hours. 30 ml brine were added and the mixture was stirred for two hours. The reaction mixture was filtered through a pad of celite, the solvent removed in vacuo and the resulting residue dissolved in 200 ml ethanol. The mixture was heated to reflux for three hours. Then the solvent was removed in vacuo and the residue dissolved in water and extracted five times with ethyl acetate. The combined organic layers were dried over MgSO4, the solvent removed in vacuo and the residue purified by flash chromatography on silica gel (eluting with n-heptane:ethyl acetate=2:3=>ethylacetate) to obtain 4.8 g 5-hydroxymethyl-2-(4-methoxy-phenyl)-oxazole-4-carboxylic acid ethyl ester as a solid.

C14H15NO5 (277.28), MS (ESI): 278.1 (M+H$^+$), Rf (ethyl acetate:n-heptane=1:2)=0.09).

2-(4-Methoxy-phenyl)-5-(tetrahydro-pyran-2-yloxymethyl)-oxazole-4-carboxylic acid ethyl ester

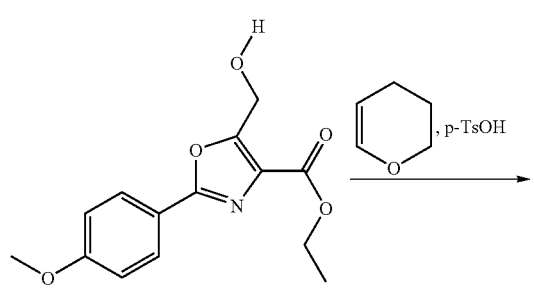

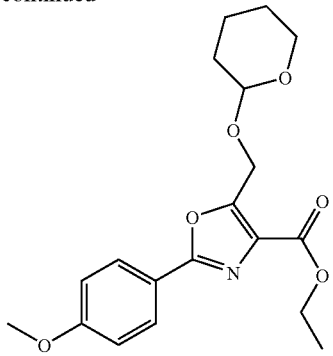

4.8 g 5-Hydroxymethyl-2-(4-methoxy-phenyl)-oxazole-4-carboxylic acid ethyl ester were dissolved in 75 ml dichloromethane. 1.9 ml 3,4-dihydro-2H-pyran and 870 mg pyridinium p-toluenesulfonate were added and the reaction mixture stirred at room temperature over night. The solvent was removed in vacuo and the residue purified by flash chromatography on silica gel (eluting with n-heptane:ethyl acetate=3:1=>1:1) to obtain 5.3 g 2-(4-methoxy-phenyl)-5-(tetrahydro-pyran-2-yloxymethyl)-oxazole-4-carboxylic acid ethyl ester.

C19H23NO6 (361.40), MS (ESI): 362.2 (M+H$^+$), 278.1 (M-THP+H+).

[2-(4-Methoxy-phenyl)-5-(tetrahydro-pyran-2-yloxymethyl)-oxazol-4-yl]-methanol

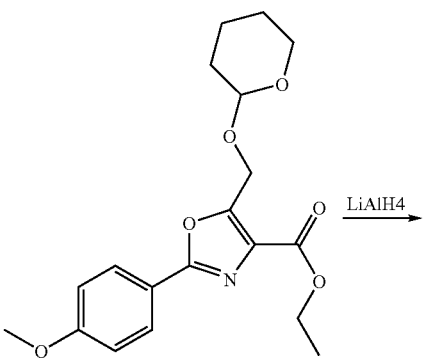

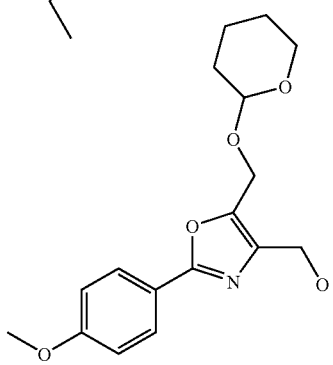

5.3 g 2-(4-Methoxy-phenyl)-5-(tetrahydro-pyran-2-yloxymethyl)-oxazole-4-carboxylic acid ethyl ester were dissolved in 100 ml tetrahydrofuran and cooled in an ice bath. 21.8 ml of a one molar solution of lithium aluminium hydride in tetrahydrofuran were added. The cooling bath was removed and the reaction mixture stirred at room temperature for thirty minutes. The reaction mixture was cooled in an ice bath again and sequentially added 6 ml water, 12 ml 15% NaOH and 18 ml water. After being stirred for one hour at room temperature the reaction mixture was filtered over a pad of celite and washed with ethyl acetate. The filtrate was dried over MgSO4 and the solvent was removed in vacuo and the residue purified by flash chromatography on silica gel (eluting with n-heptane:ethyl acetate=6:4=>9:1=>ethyl acetate) to obtain 3.0 g [2-(4-Methoxy-phenyl)-5-(tetrahydro-pyran-2-yloxymethyl)-oxazol-4-yl]-methanol.

C17H21NO5 (319.36), MS (ESI): 320.2 (M+H+).

Methanesulfonic acid 2-(4-methoxy-phenyl)-5-(tetrahydro-pyran-2-yloxymethyl)-oxazol-4-ylmethyl ester

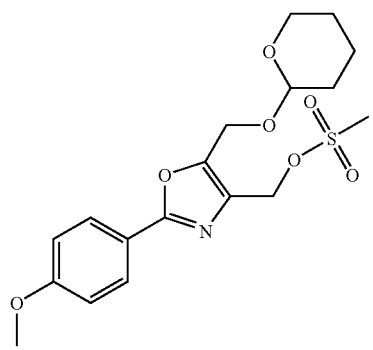

0.44 g [2-(4-Methoxy-phenyl)-5-(tetrahydro-pyran-2-yloxymethyl)-oxazol-4-yl]-methanol were dissolved in 30 ml dichloromethane and cooled in an ice bath. 0.29 ml triethylamine were added, followed by the addition of 0.13 ml methanesulfonylchloride. The reaction mixture was stirred at 0° C. for one hour then the ice bath was removed and the resulting mixture stirred at room temperature for an additional hour. The reaction mixture was then washed with water and brine, dried over MgSO4 and the solvent removed in vacuo to obtain 0.55 mg of methanesulfonic acid 2-(4-methoxy-phenyl)-5-(tetrahydro-pyran-2-yloxymethyl)-oxazol-4-ylmethyl ester as an oil which was used without further purification.

C18H23NO7S (397.45), MS (ESI): 398.2 (M+H+).

Example 1

3-{2-Fluoro-4-[4-methyl-2-(4-trifluoromethyl-phenyl)-thiazole-5-ylmethoxy]-phenyl}-4H-[1,2,4]oxadiazole-5-one

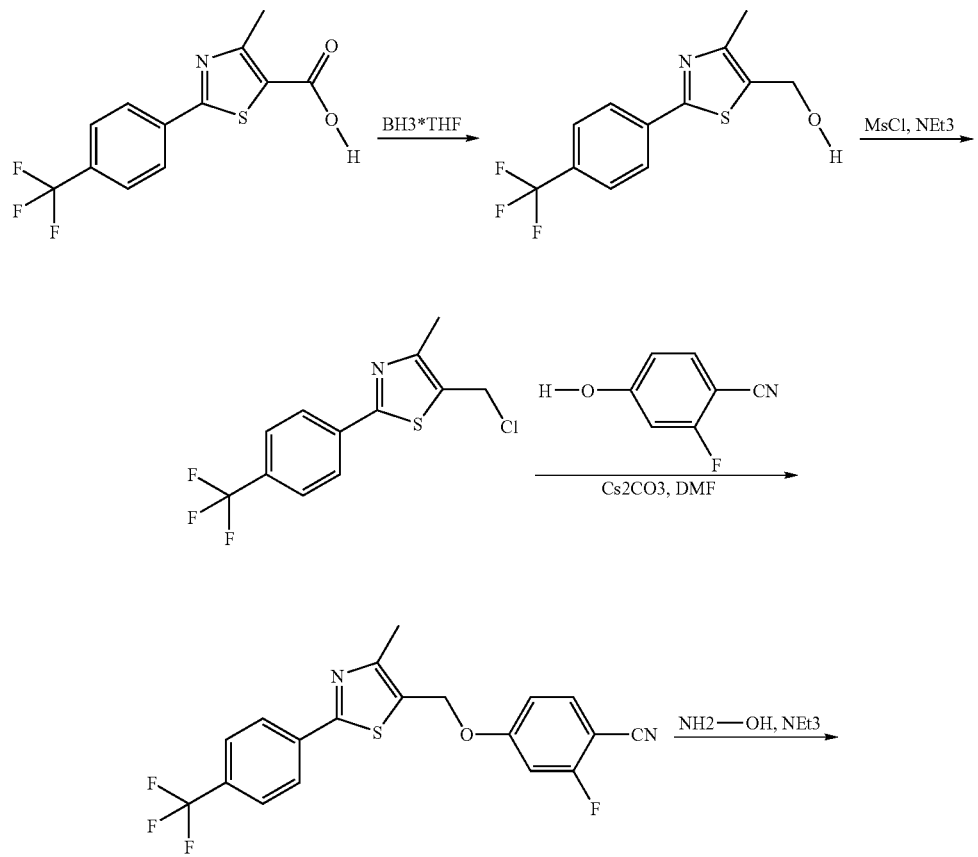

-continued

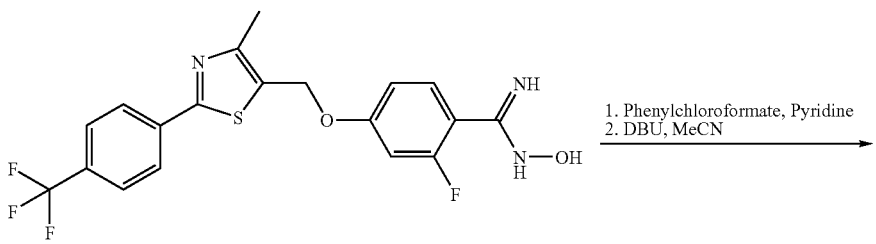

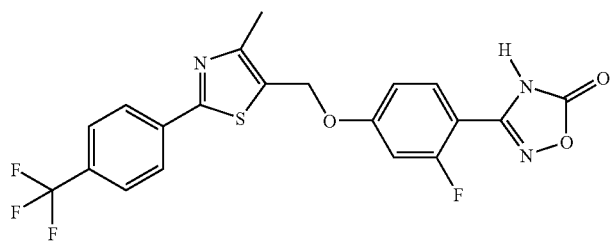

Example 1

[4-Methyl-2-(4-trifluoromethyl-phenyl)-thiazole-5-yl]-methanol

5-Chloromethyl-4-methyl-2-(4-trifluoromethyl-phenyl)-thiazole

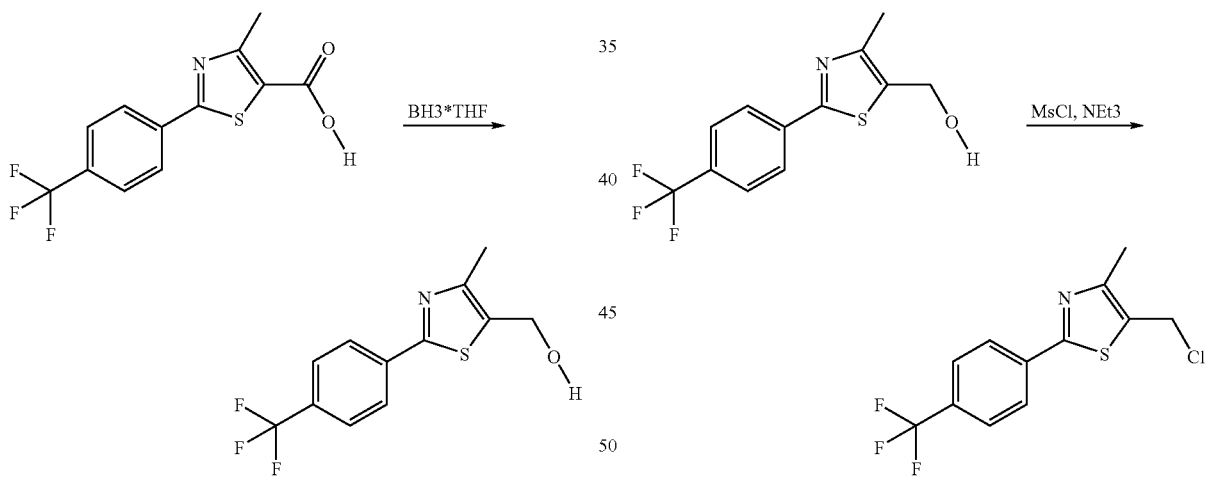

10.0 g of 4-Methyl-2-(4-trifluoromethyl-phenyl)-thiazole-5-carboxylic acid were dissolved in 50 ml tetrahydrofuran under an atmosphere of argon. 69.7 ml of boran-tetrahydrofuran complex (1 molar solution in tetrahydrofuran) was added and the mixture refluxed for three hours. Water was added to the cooled reaction mixture and the solvent removed in vacuo. The residue was extracted five times with 50 ml portions of ethyl acetate. The combined extracts were dried over MgSO4. The solvent was removed in vacuo to obtain 9.3 g of [4-Methyl-2-(4-trifluoromethyl-phenyl)-thiazole-5-yl]-methanol as a yellow solid.

C12H10F3NOS (273.28), MS (ESI): 274.2 (M+H$^+$), Rf=0.21 (n-heptane:ethyl acetate=2:1).

3.0 g of [4-Methyl-2-(4-trifluoromethyl-phenyl)-thiazole-5-yl]-methanol were dissolved in 50 ml dichloromethane, 3.0 ml of triethylamine were added followed by the addition of 1.36 ml of methanesulfonylchloride. The reaction mixture was stirred at room temperature for two hours. 100 ml dichloromethane were added and the mixture washed with saturated sodium hydrogen carbonate solution, water and brine. The organic layer was dried over MgSO$_4$. The solvent was removed in vacuo to obtain 3.3 g of crude 5-Chloromethyl-4-methyl-2-(4-trifluoromethyl-phenyl)-thiazole as a brown oil.

C12H9ClF3NS (291.72), MS (ESI): 292.2 (M+H$^+$).

2-Fluoro-4-[4-methyl-2-(4-trifluoromethyl-phenyl)-thiazole-5-ylmethoxy]-benzonitrile

2-Fluoro-N-hydroxy-4-[4-methyl-2-(4-trifluoromethyl-phenyl)-thiazole-5-ylmethoxy]-benzamidine

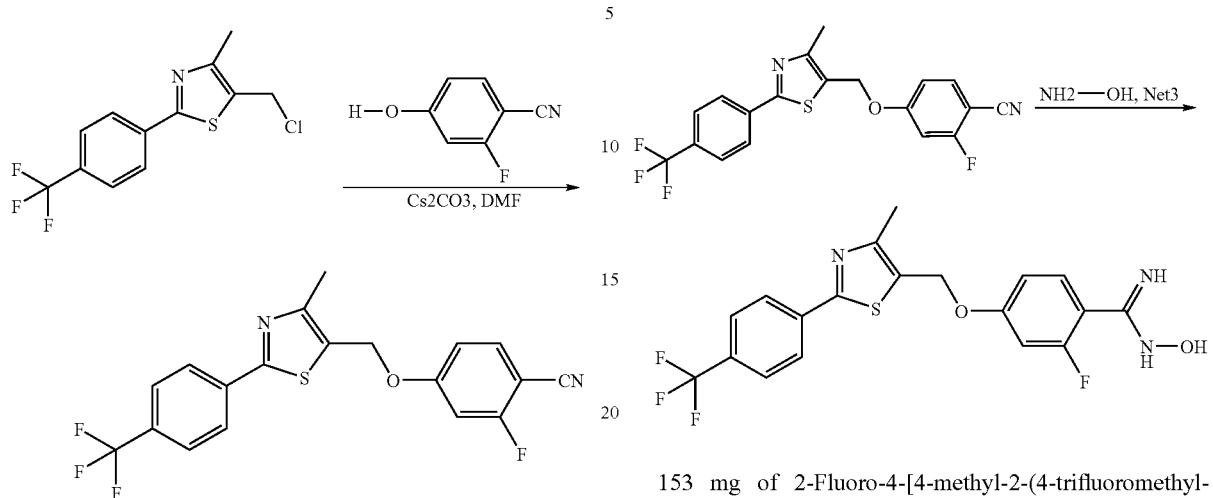

560 mg of 5-Chloromethyl-4-methyl-2-(4-trifluoromethyl-phenyl)-thiazole were dissolved in 10 ml dimethylformamide. 1.2 g of cesium carbonate and 395 mg 2-Fluoro-4-hydroxybenzonitrile was added and the mixture was stirred at room temperature for three hours. Then 50 ml of methyl-tert-butylether was added, the mixture washed with brine and dried over MgSO4. The solvent was removed in vacuo. The resulting crude material was purified by reversed phase HPLC to obtain 153 mg of 2-Fluoro-4-[4-methyl-2-(4-trifluoromethyl-phenyl)-thiazole-5-ylmethoxy]-benzonitrile as amorphous lyophilisate.

C19H12F4N2OS (392.38), MS (ESI): 393.1 (M+H$^+$).

153 mg of 2-Fluoro-4-[4-methyl-2-(4-trifluoromethyl-phenyl)-thiazole-5-ylmethoxy]-benzonitrile were dissolved in a mixture of 1 ml tetrahydrofuran and 2 ml methanol. 265 mg hydroxylamine hydrochloride was added followed by the addition of 0.5 ml triethylamine. The reaction mixture was stirred at 60° C. for twenty hours. The solvents were removed in vacuo and the resulting residue poured into water and extracted five times with ethylacetate. The combined organic extracts were washed with brine, dried over MgSO4 and the solvent was evaporated in vacuo to obtain 138 mg of 2-Fluoro-N-hydroxy-4-[4-methyl-2-(4-trifluoromethyl-phenyl)-thiazole-5-ylmethoxy]-benzamidine as crude material.

C19H15F4N3O2S (425.41), MS (ESI): 426.1 (M+H$^+$).

3-{2-Fluoro-4-[4-methyl-2-(4-trifluoromethyl-phenyl)-thiazole-5-ylmethoxy]-phenyl}-4H-[1,2,4]oxadiazole-5-one Example 1

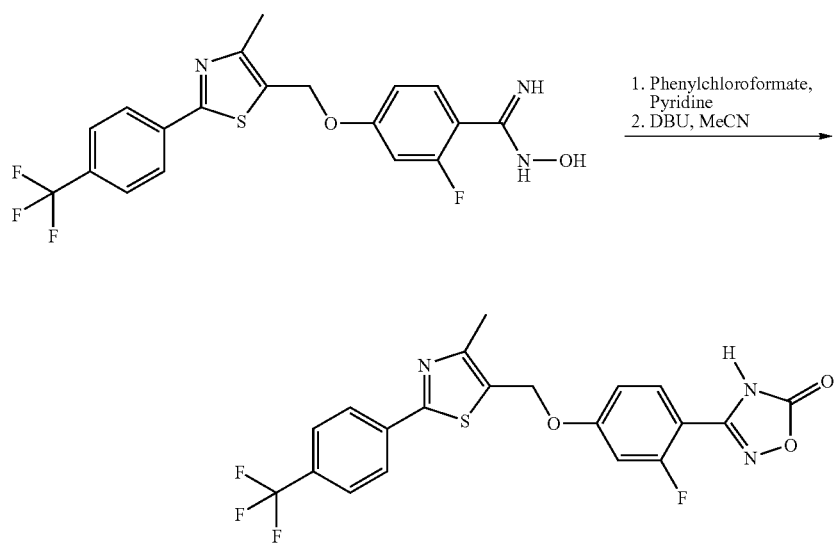

138 mg of 2-Fluoro-N-hydroxy-4-[4-methyl-2-(4-trifluoromethyl-phenyl)-thiazole-5-ylmethoxy]-benzamidine were dissolved in 2 ml dichloromethane. 35 µl pyridine and 53 µl phenylchloroformate were added and the mixture stirred at room temperature for thirty minutes. The mixture was diluted by the addition of 20 ml ethyl acetate, washed with brine and dried over MgSO4. The solvent was evaporated in vacuo. The resulting residue was dissolved in 2 ml acetonitrile and 105 µl 1,8-Diazabicyclo[5.4.0]undec-7-ene was added. The mixture was stirred at room temperature for 10 minutes. The mixture was evaporated in vacuo and the resulting crude material was purified by reversed phase HPLC to obtain 70 mg 3-{2-Fluoro-4-[4-methyl-2-(4-trifluoromethyl-phenyl)-thiazole-5-ylmethoxy]-phenyl}-4H-[1,2,4]oxadiazole-5-one as an amorphous lyophilisate.

C20H13F4N3O3S (451.40), MS (ESI): 452.1 (M+H+).

Example 2

3-{4-[4-Methyl-2-(4-trifluoromethyl-phenyl)-thiazole-5-ylmethoxy]-phenyl}-4H-[1,2,4]oxadiazole-5-one

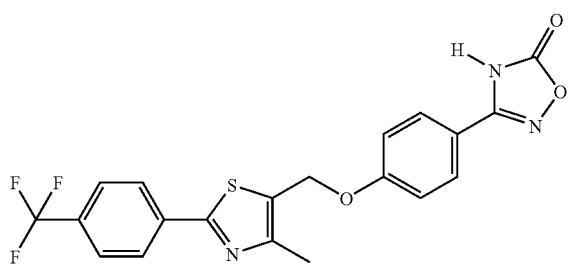

According to the method described in Example 1 3-{4-[4-Methyl-2-(4-trifluoromethyl-phenyl)-thiazole-5-ylmethoxy]-phenyl}-4H-[1,2,4]oxadiazole-5-one was obtained from 5-Chloromethyl-4-methyl-2-(4-trifluoromethyl-phenyl)-thiazole and commercially available 4-Hydroxy-benzonitrile.

C20H14F3N3O3S (433.41), MS (ESI): 434.3 (M+H+).

Example 3

3-{3-Methoxy-4-[4-methyl-2-(4-trifluoromethyl-phenyl)-thiazole-5-ylmethoxy]-phenyl}-4H-[1,2,4]oxadiazole-5-one

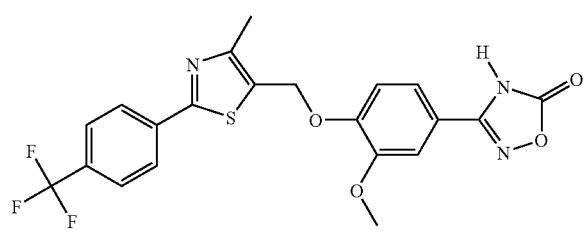

According to the method described in Example 1 3-{3-Methoxy-4-[4-methyl-2-(4-trifluoromethyl-phenyl)-thiazole-5-ylmethoxy]-phenyl}-4H-[1,2,4]oxadiazole-5-one was obtained from 5-Chloromethyl-4-methyl-2-(4-trifluoromethyl-phenyl)-thiazole and commercially available 4-Hydroxy-3-methoxy-benzonitrile.

C21H16F3N3O4S (463.44), MS (ESI): 464.2 (M+H+).

Example 4

3-{2-Chloro-4-[4-methyl-2-(4-trifluoromethyl-phenyl)-thiazole-5-ylmethoxy]-phenyl}-4H-[1,2,4]oxadiazole-5-one

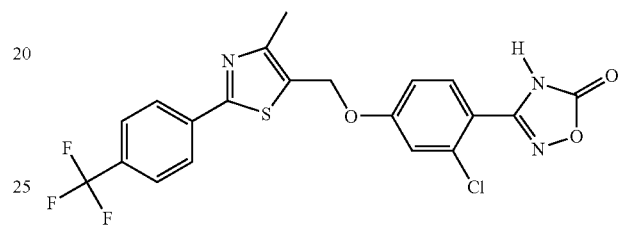

According to the method described in Example 1 3-{2-Chloro-4-[4-methyl-2-(4-trifluoromethyl-phenyl)-thiazole-5-ylmethoxy]-phenyl}-4H-[1,2,4]oxadiazole-5-one was obtained from 5-Chloromethyl-4-methyl-2-(4-trifluoromethyl-phenyl)-thiazole and commercially available 2-Chloro-4-hydroxy-benzonitrile.

C20H13ClF3N3O3S (467.86), MS (ESI): 468.2 (M+H+).

Example 5

3-{4-[4-Methyl-2-(4-trifluoromethyl-phenyl)-thiazole-5-ylmethylsulfanyl]-phenyl}-4H-[1,2,4]oxadiazole-5-one

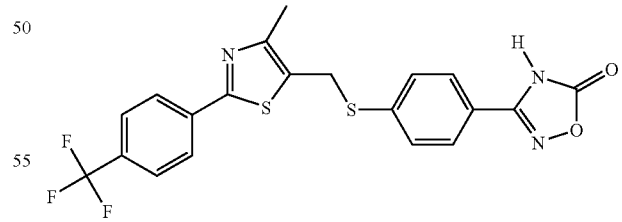

According to the method described in Example 1 3-{4-[4-Methyl-2-(4-trifluoromethyl-phenyl)-thiazole-5-ylmethylsulfanyl]-phenyl}-4H-[1,2,4]oxadiazole-5-one was obtained from 5-Chloromethyl-4-methyl-2-(4-trifluoromethyl-phenyl)-thiazole and commercially available 4-Mercapto-benzonitrile.

C20H14F3N3O2S2 (449.48), MS (ESI): 450.2 (M+H+).

Example 6

3-{4-[4-Butyl-2-(4-trifluoromethyl-phenyl)-thiazole-5-ylmethoxy]-2-chloro-phenyl}-4H-[1,2,4]oxadiazole-5-one

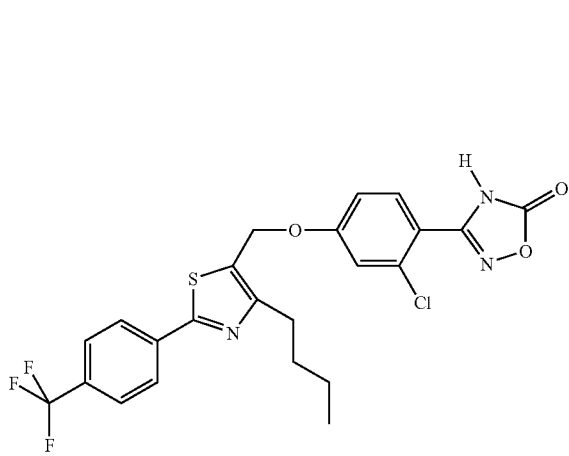

According to the method described in Example 1 3-{4-[4-Butyl-2-(4-trifluoromethyl-phenyl)-thiazole-5-ylmethoxy]-2-chloro-phenyl}-4H-[1,2,4]oxadiazole-5-one was obtained from 4-Butyl-5-chloromethyl-2-(4-trifluoromethyl-phenyl)-thiazole and commercially available 2-Chloro-4-hydroxy-benzonitrile.

C23H19ClF3N3O3S (509.94), MS (ESI): 510.3 (M+H$^+$)

Example 7

3-{4-[4-Butyl-2-(4-pentafluorosulfanyl-phenyl)-thiazole-5-ylmethoxy]-2-chloro-phenyl}-4H-[1,2,4]oxadiazole-5-one

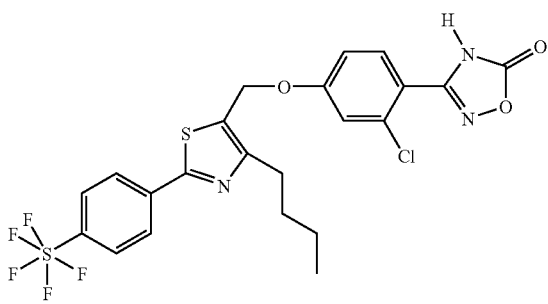

According to the method described in Example 1 3-{4-[4-Butyl-2-(4-pentafluorosulfanyl-phenyl)-thiazole-5-ylmethoxy]-2-chloro-phenyl}-4H-[1,2,4]oxadiazole-5-one was obtained from 4-Butyl-5-chloromethyl-2-(4-pentafluorosulfanyl-phenyl)-thiazole and commercially available 2-Chloro-4-hydroxy-benzonitrile.

C22H19ClF5N3O3S2 (567.4), MS (ESI): 568.1 (M+H$^+$)

Example 8

3-{2-Chloro-4-[4-methyl-2-(4-pentafluorosulfanyl-phenyl)-thiazole-5-ylmethoxy]-phenyl}-4H-[1,2,4]oxadiazole-5-one

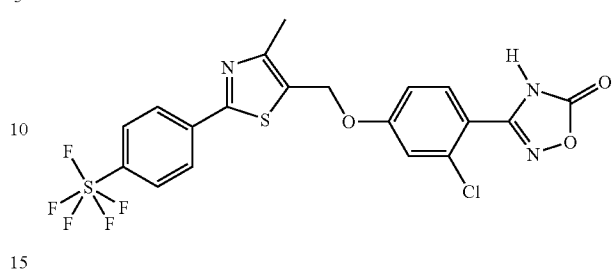

According to the method described in Example 1 3-{2-Chloro-4-[4-methyl-2-(4-pentafluorosulfanyl-phenyl)-thiazole-5-ylmethoxy]-phenyl}-4H-[1,2,4]oxadiazole-5-one was obtained from 5-Chloromethyl-4-methyl-2-(4-pentafluorosulfanyl-phenyl)-thiazole and commercially available 2-Chloro-4-hydroxy-benzonitrile.

C19H13ClF5N3O3S2 (525.91), MS (ESI): 526.0 (M+H$^+$).

Example 9

3-(4-{2-[4-Butyl-2-(4-trifluoromethyl-phenyl)-thiazol-5-yl]-ethoxy}-2-chloro-phenyl)-4H-[1,2,4]oxadiazol-5-one 4-{2-[4-Butyl-2-(4-trifluoromethyl-phenyl)-thiazol-5-yl]-ethoxy}-2-chloro-benzonitrile

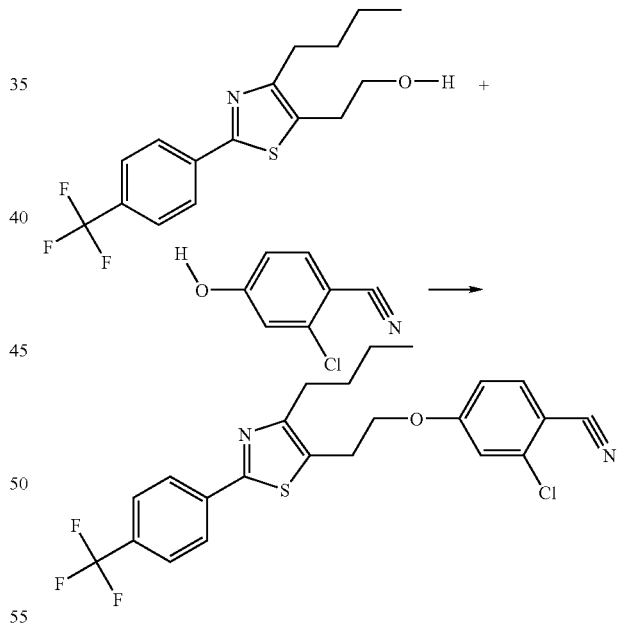

To an iced cooled solution of 1.1 g 2-[4-Butyl-2-(4-trifluoromethyl-phenyl)-thiazol-5-yl]-ethanol dissolved in 50 ml dichloromethane were added 0.56 g commercially available 2-Chloro-4-hydroxybenzonitrile and 0.95 g triphenylphosphine. To this solution was added dropwise 0.57 ml Diethylazodicarboxylate. The cooling bath was removed and reaction mixture stirred at room temperature for six hours. The solvent was removed in vacuo and the residue purified by RP-HPLC to provide 400 mg 4-{2-[4-Butyl-2-(4-trifluoromethyl-phenyl)-thiazol-5-yl]-ethoxy}-2-chloro-benzonitrile as lyophilisate.

C23H20ClF3N2OS (464.94), MS (ESI): 465.2 (M+H$^+$).

81

3-(4-{2-[4-Butyl-2-(4-trifluoromethyl-phenyl)-thiazol-5-yl]-ethoxy}-2-chloro-phenyl)-4H-[1,2,4]oxadiazol-5-one

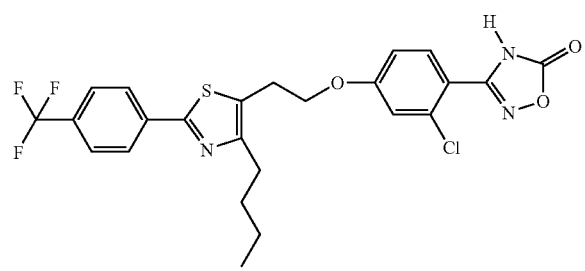

82

According to the method described in Example 1 3-(4-{2-[4-Butyl-2-(4-trifluoromethyl-phenyl)-thiazol-5-yl]-ethoxy}-2-chloro-phenyl)-4H-[1,2,4]oxadiazol-5-one was obtained from 4-{2-[4-Butyl-2-(4-trifluoromethyl-phenyl)-thiazol-5-yl]-ethoxy}-2-chloro-benzonitrile.

$C_{24}H_{21}ClF_3N_3O_3S$ (523.97), MS (ESI): 524.3 (M+H$^+$).

Example 10

3-{4-[4-Butyl-2-(4-trifluoromethyl-phenyl)-thiazol-5-ylmethoxy]-2-chloro-benzyl}-4H-[1,2,4]oxadiazol-5-one

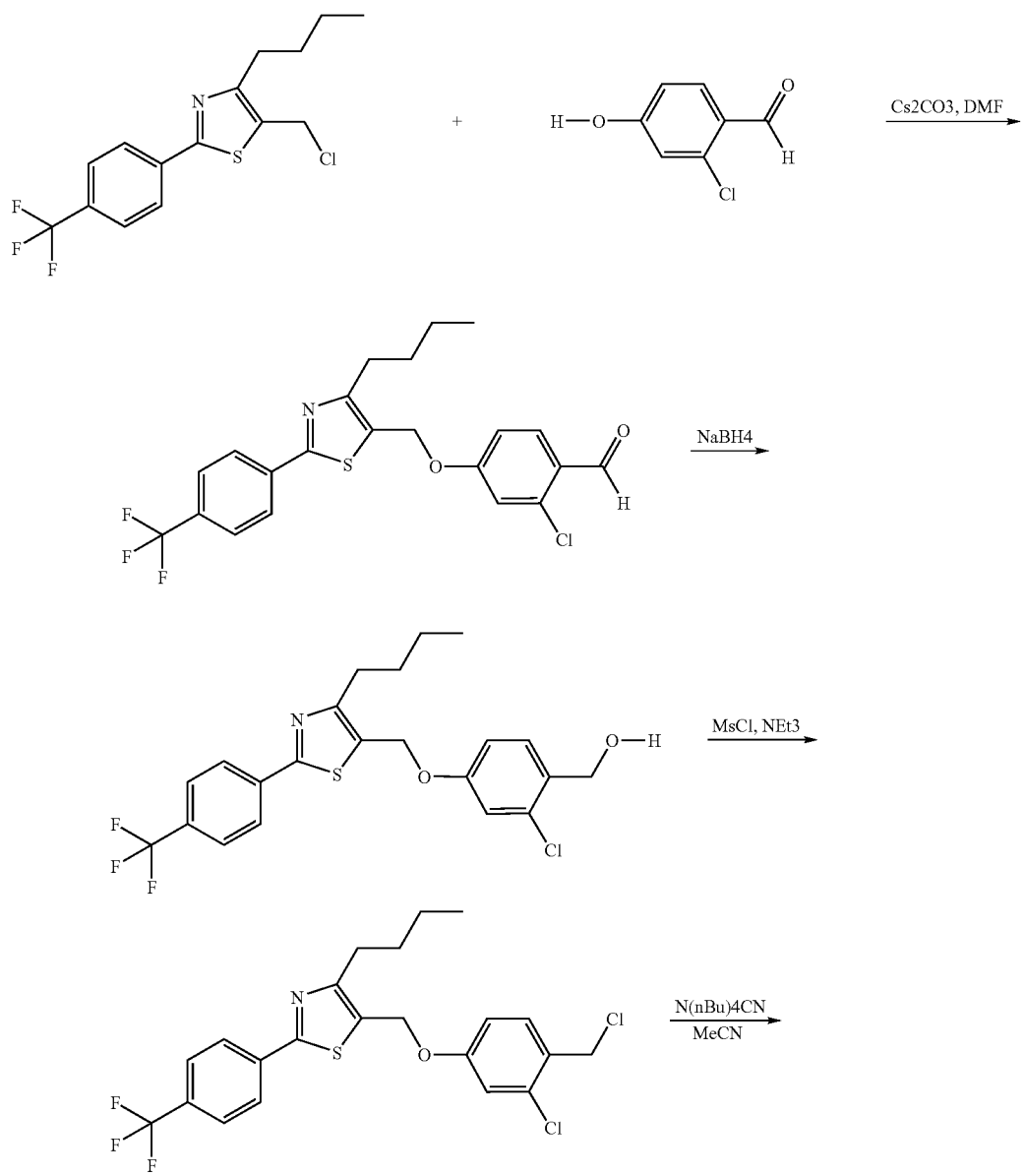

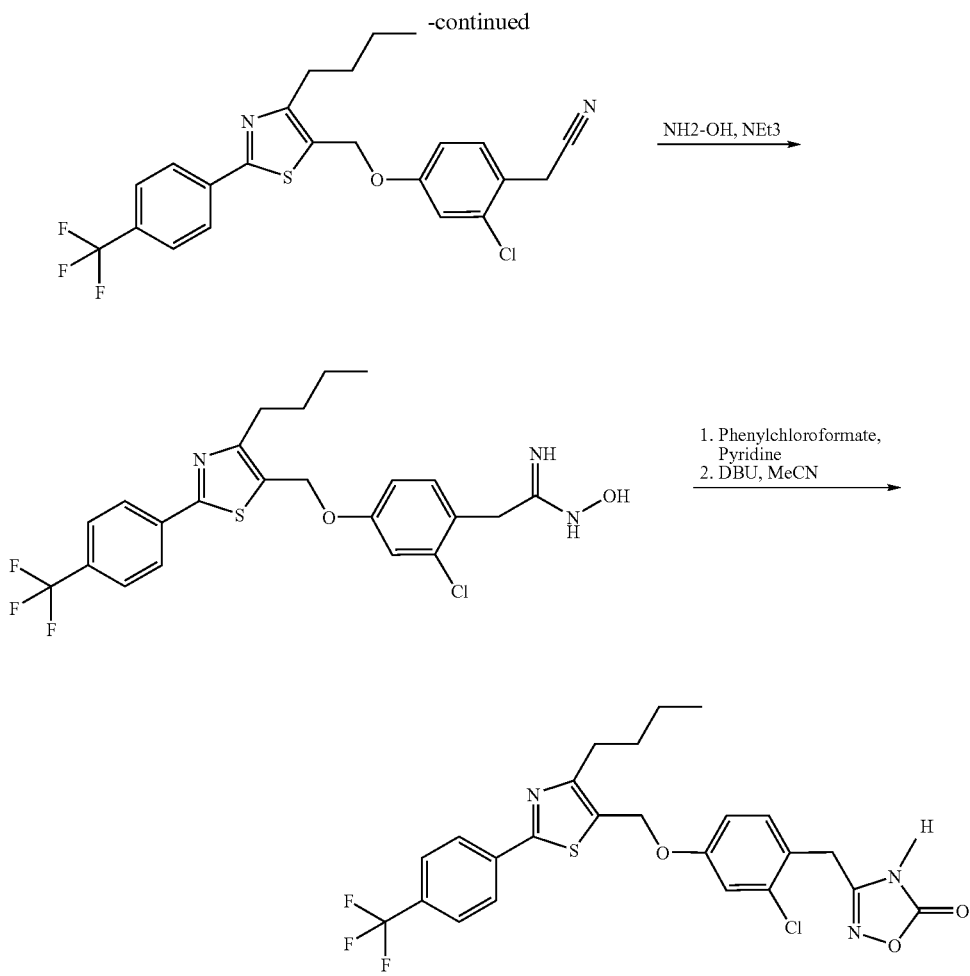

4-[4-Butyl-2-(4-trifluoromethyl-phenyl)-thiazol-5-ylmethoxy]-2-chloro-benzaldehyde

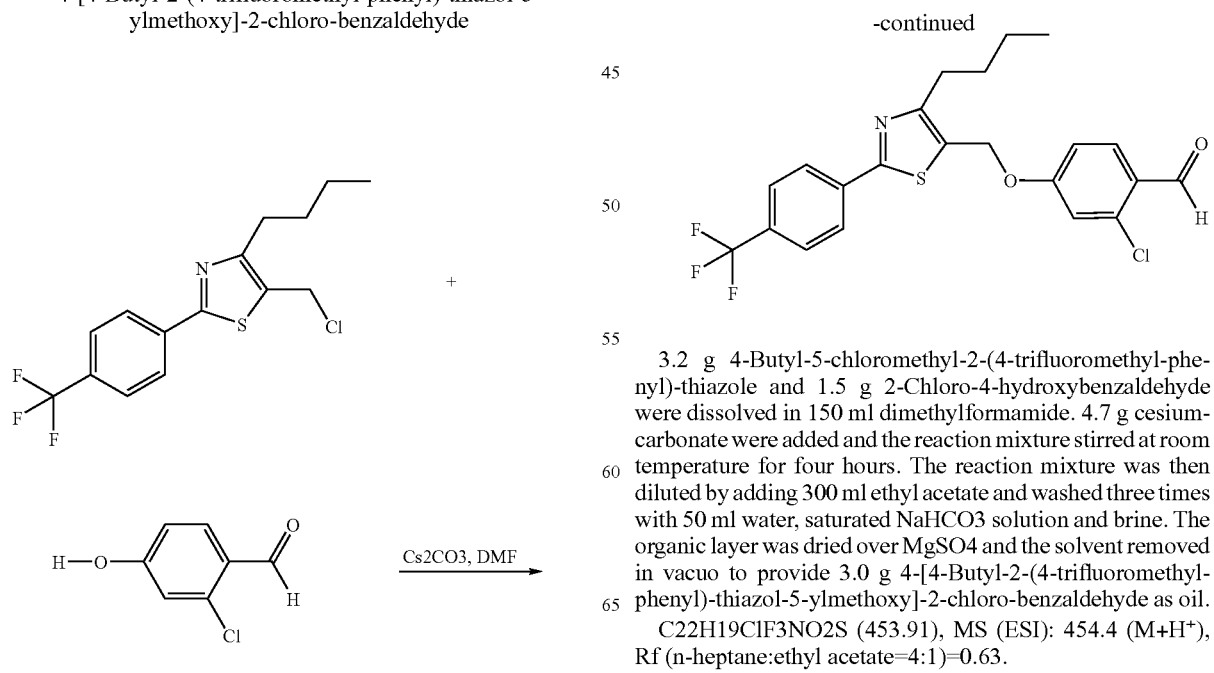

3.2 g 4-Butyl-5-chloromethyl-2-(4-trifluoromethyl-phenyl)-thiazole and 1.5 g 2-Chloro-4-hydroxybenzaldehyde were dissolved in 150 ml dimethylformamide. 4.7 g cesium-carbonate were added and the reaction mixture stirred at room temperature for four hours. The reaction mixture was then diluted by adding 300 ml ethyl acetate and washed three times with 50 ml water, saturated NaHCO3 solution and brine. The organic layer was dried over MgSO4 and the solvent removed in vacuo to provide 3.0 g 4-[4-Butyl-2-(4-trifluoromethyl-phenyl)-thiazol-5-ylmethoxy]-2-chloro-benzaldehyde as oil.

C22H19ClF3NO2S (453.91), MS (ESI): 454.4 (M+H$^+$), Rf (n-heptane:ethyl acetate=4:1)=0.63.

85

{4-[4-Butyl-2-(4-trifluoromethyl-phenyl)-thiazol-5-ylmethoxy]-2-chloro-phenyl}-methanol

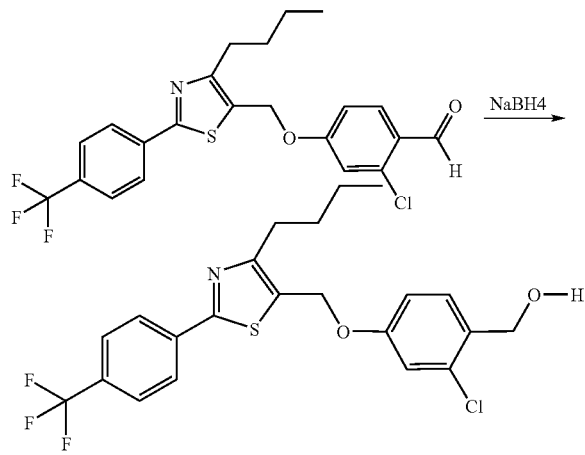

3.0 g 4-[4-Butyl-2-(4-trifluoromethyl-phenyl)-thiazol-5-ylmethoxy]-2-chloro-benzaldehyde were dissolved in 100 ml methanol and 300 mg sodium borohydride were added. The reaction mixture was stirred at room temperature for two hours, then the solvent was removed in vacuo and the residue dissolved in 100 ml ethyl acetate. This solution was washed three times with 30 ml brine, dried over MgSO4 and the solvent was removed in vacuo to provide 3.0 g {4-[4-Butyl-2-(4-trifluoromethyl-phenyl)-thiazol-5-ylmethoxy]-2-chloro-phenyl}-methanol as pale yellow solid.

C22H21ClF3NO2S (455.93), MS (ESI): 456.4 (M+H$^+$), Rf (n-heptane:ethyl acetate=1:1)=0.44.

4-Butyl-5-(3-chloro-4-chloromethyl-phenoxymethyl)-2-(4-trifluoromethyl-phenyl)-thiazole

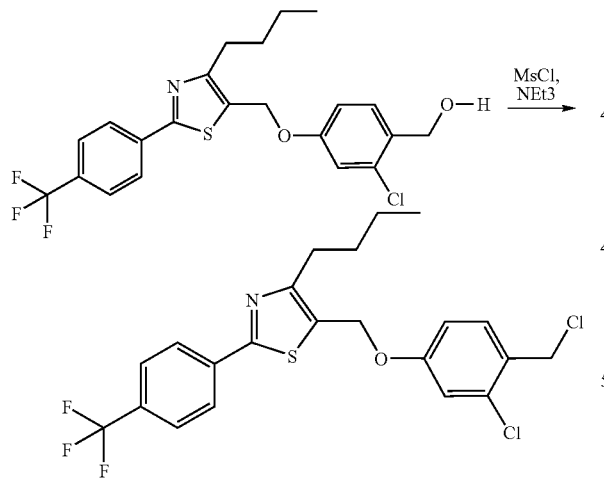

3.0 g {4-[4-Butyl-2-(4-trifluoromethyl-phenyl)-thiazol-5-ylmethoxy]-2-chloro-phenyl}-methanol and 1.84 ml triethylamine were dissolved in 150 ml dichloromethane. To this ice cooled solution were added 0.82 ml methanesulfonylchloride. The cooling bath was removed and the reaction mixture was stirred at room temperature additional three hours. The reaction mixture was washed three times with 50 ml saturated NaHCO3 solution dried over MgSO4 and the solvent was removed in vacuo to provide 3.1 g 4-Butyl-5-(3-chloro-4-chloromethyl-phenoxymethyl)-2-(4-trifluoromethyl-phenyl)-thiazole as crude material. This material was used without further purification.

C22H20Cl2F3NOS (474.38), MS (ESI): 476.4 (M+H$^+$).

86

{4-[4-Butyl-2-(4-trifluoromethyl-phenyl)-thiazol-5-ylmethoxy]-2-chloro-phenyl}-acetonitrile

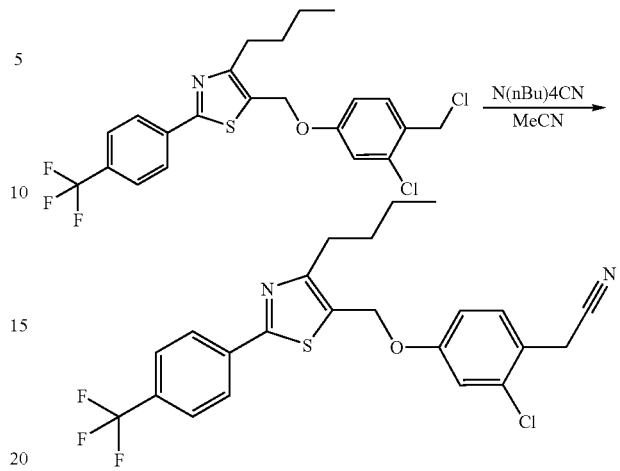

3.1 g crude 4-Butyl-5-(3-chloro-4-chloromethyl-phenoxymethyl)-2-(4-trifluoromethyl-phenyl)-thiazole was dissolved in 50 ml acetonitrile. 2.0 g tetrabutylammonium cyanide were added and the reaction mixture stirred at room temperature for one hour. Then a mixture of saturated NaHCO3 solution, ice and ethyl acetate was added. The aqueous phase was separated and extracted three times with portions of 30 ml ethylacetate. The combined organic layers were washed with ice cold water and brine and dried over MgSO4. The solvent was removed in vacuo. The residue was purified by flash chromatography with the eluent n-heptane:ethyl acetate=4:1 to provide 2.2 g {4-[4-Butyl-2-(4-trifluoromethyl-phenyl)-thiazol-5-ylmethoxy]-2-chloro-phenyl}-acetonitrile as oil.

C23H20ClF3N2OS (464.94), MS (ESI): 465.5 (M+H$^+$), Rf (n-heptane:ethyl acetate=4:1)=0.32.

2-{4-[4-Butyl-2-(4-trifluoromethyl-phenyl)-thiazol-5-ylmethoxy]-2-chloro-phenyl}-N-hydroxy-acetamidine

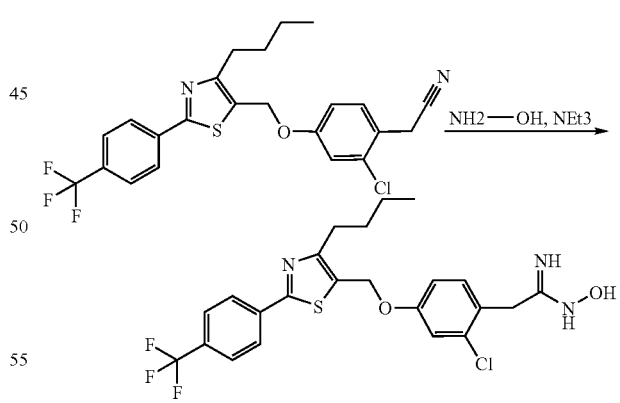

2.2 g {4-[4-Butyl-2-(4-trifluoromethyl-phenyl)-thiazol-5-ylmethoxy]-2-chloro-phenyl}-acetonitrile were dissolved in a mixture of 6 ml tetrahydrofuran and 12 ml methanol. 3.3 g hydroxylamine hydrochloride were added followed by the addition of 6.6 ml triethylamine. The reaction mixture was stirred at 60° C. for two hours. The solvents were removed in vacuo and the resulting residue poured into water and extracted five times with portions of 30 ml ethylacetate. The combined organic extracts were dried over MgSO4 and the solvent was evaporated in vacuo to provide 2.3 g 2-{4-[4-

Butyl-2-(4-trifluoromethyl-phenyl)-thiazol-5-ylmethoxy]-2-chloro-phenyl}-N-hydroxy-acetamidine as crude material. C23H23ClF3N3O2S (497.97), MS (ESI): 498.5 (M+H$^+$).

3-{4-[4-Butyl-2-(4-trifluoromethyl-phenyl)-thiazol-5-ylmethoxy]-2-chloro-benzyl}-4H-[1,2,4]oxadiazol-5-one

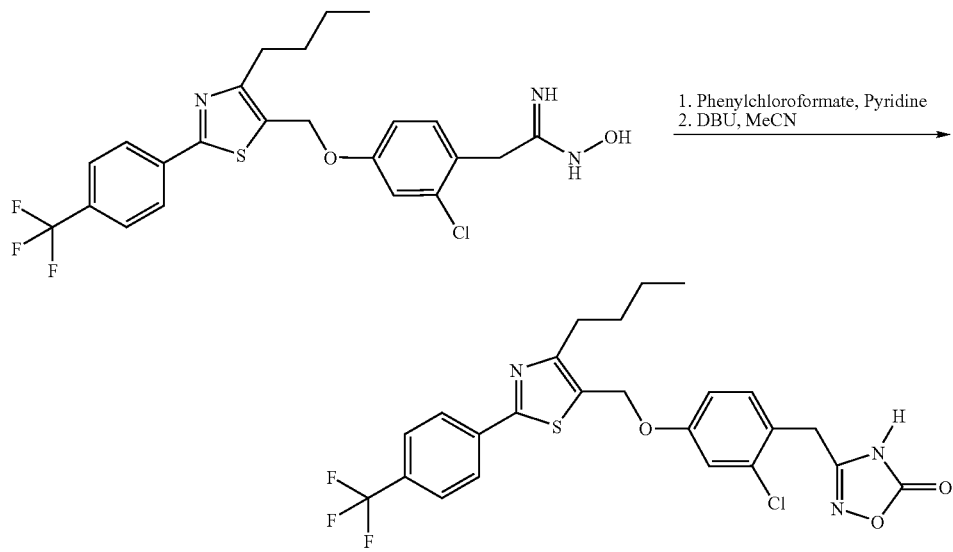

Example 10

2.3 g crude 2-{4-[4-Butyl-2-(4-trifluoromethyl-phenyl)-thiazol-5-ylmethoxy]-2-chloro-phenyl}-N-hydroxy-acetamidine were dissolved in 30 ml dichloromethane. 0.46 ml pyridine and 0.71 ml phenylchloroformate were added and the mixture stirred at room temperature for ten minutes. The mixture was diluted by the addition of 150 ml ethyl acetate, washed with brine and dried over MgSO4. The solvent was evaporated in vacuo. The resulting residue was dissolved in 20 ml acetonitrile and 0.70 ml 1,8-Diazabicyclo[5.4.0]undec-7-ene were added. The mixture was stirred at room temperature for 10 minutes. The mixture was evaporated in vacuo and the resulting crude material was purified by reversed phase HPLC to obtain 820 mg 3-{4-[4-Butyl-2-(4-trifluoromethyl-phenyl)-thiazol-5-ylmethoxy]-2-chloro-benzyl}-4H-[1,2,4]oxadiazol-5-one as an amorphous lyophilisate.
C24H21ClF3N3O3S (523.97), MS (ESI): 524.3 (M+H$^+$).

Example 11

3-{2-Methoxy-4-[4-methyl-2-(4-trifluoromethyl-phenyl)-thiazol-5-ylmethoxy]-phenyl}-4H-[1,2,4]oxadiazol-5-one

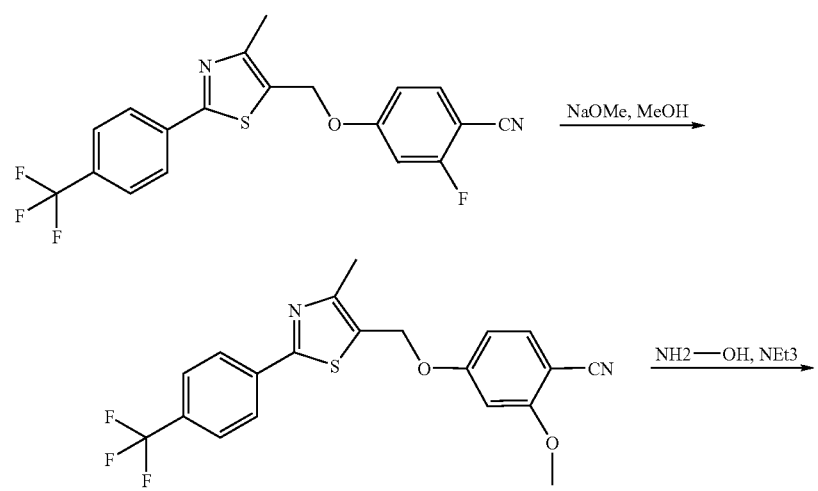

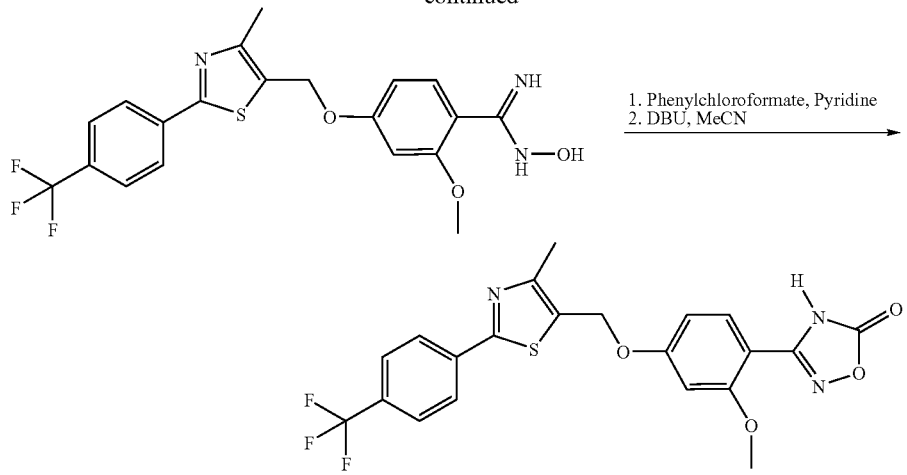

2-Methoxy-4-[4-methyl-2-(4-trifluoromethyl-phenyl)-thiazol-5-ylmethoxy]-benzonitrile

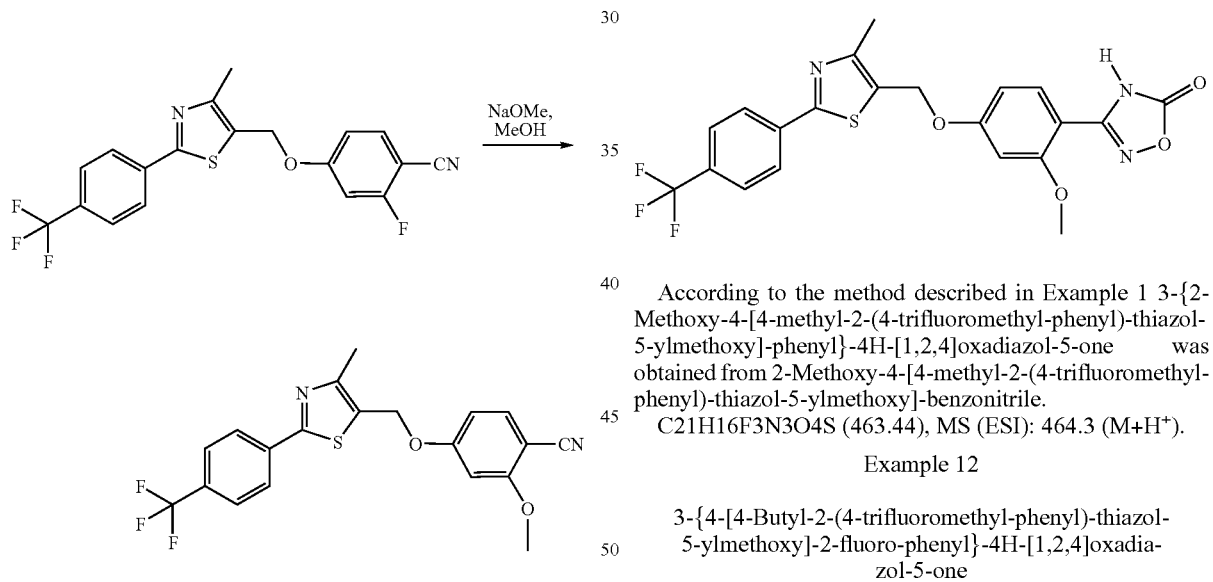

280 mg 2-Fluoro-4-[4-methyl-2-(4-trifluoromethyl-phenyl)-thiazole-5-ylmethoxy]-benzonitrile (intermediate example 1) were dissolved in 10 ml methanol. 390 mg sodium methoxide were added and the reaction mixture stirred at a temperature of 60° C. for two hours. The cooled reaction mixture was diluted by adding 200 ml ethyl acetate and washed three times with portions of 50 ml water. The organic layer was dried over MgSO4 and the solvent removed in vacuo to provide 140 mg 2-Methoxy-4-[4-methyl-2-(4-trifluoromethyl-phenyl)-thiazol-5-ylmethoxy]-benzonitrile as pale yellow solid.

C20H15F3N2O2S (404.41), MS (ESI): 405.4 (M+H$^+$), Rf (n-heptane:ethyl acetate=2:1)=0.32.

3-{2-Methoxy-4-[4-methyl-2-(4-trifluoromethyl-phenyl)-thiazol-5-ylmethoxy]-phenyl}-4H-[1,2,4]oxadiazol-5-one According to the method described in Example 1 3-{2-Methoxy-4-[4-methyl-2-(4-trifluoromethyl-phenyl)-thiazol-5-ylmethoxy]-phenyl}-4H-[1,2,4]oxadiazol-5-one was obtained from 2-Methoxy-4-[4-methyl-2-(4-trifluoromethyl-phenyl)-thiazol-5-ylmethoxy]-benzonitrile.

C21H16F3N3O4S (463.44), MS (ESI): 464.3 (M+H$^+$).

Example 12

3-{4-[4-Butyl-2-(4-trifluoromethyl-phenyl)-thiazol-5-ylmethoxy]-2-fluoro-phenyl}-4H-[1,2,4]oxadiazol-5-one

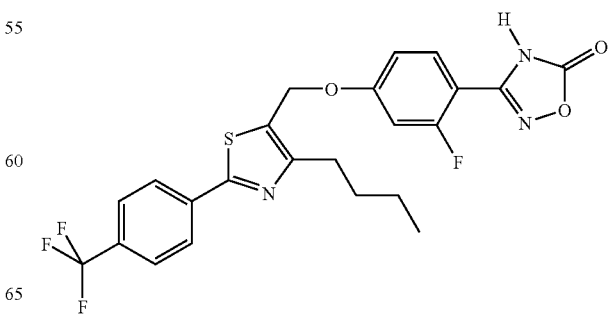

According to the method described in Example 1, 3-{4-[4-butyl-2-(4-trifluoromethyl-phenyl)-thiazol-5-ylmethoxy]-2-fluoro-phenyl}-4H-[1,2,4]oxadiazol-5-one was obtained from 4-butyl-5-chloromethyl-2-(4-trifluoromethyl-phenyl)-thiazole and commercially available 2-fluoro-4-hydroxy-benzonitrile.

C23H19F4N3O3S (493.11), MS (ESI): 494.3 (M+H⁺)

Example 13

3-{4-[4-Butyl-2-(4-trifluoromethyl-phenyl)-thiazol-5-ylmethoxy]-2,6-difluoro-phenyl}-4H-[1,2,4]oxadiazol-5-one

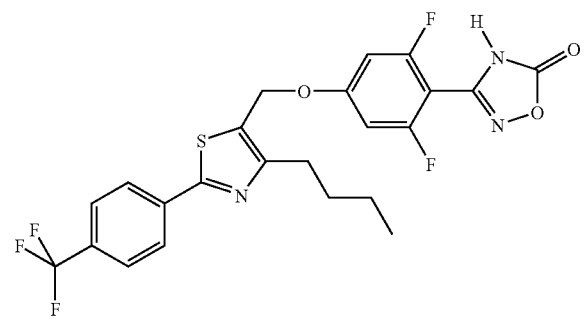

According to the method described in Example 1, 3-{4-[4-butyl-2-(4-trifluoromethyl-phenyl)-thiazol-5-ylmethoxy]-2,6-difluoro-phenyl}-4H-[1,2,4]oxadiazol-5-one was obtained from 4-butyl-5-chloromethyl-2-(4-trifluoromethyl-phenyl)-thiazole and commercially available 2,6-difluoro-4-hydroxy-benzonitrile.

C23H18F5N3O3S (511.10), MS (ESI): 512.2 (M+H⁺)

Example 14

3-{4-[4-Butyl-2-(4-trifluoromethyl-phenyl)-thiazol-5-ylmethylsulfanyl]-phenyl}-4H-[1,2,4]oxadiazol-5-one

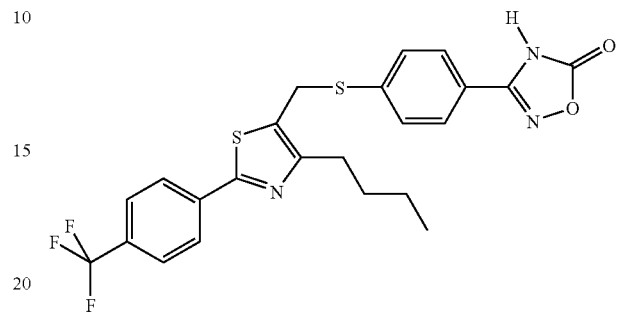

According to the method described in Example 1, 3-{4-[4-butyl-2-(4-trifluoromethyl-phenyl)-thiazol-5-ylmethylsulfanyl]-phenyl}-4H-[1,2,4]oxadiazol-5-one was obtained from 4-butyl-5-chloromethyl-2-(4-trifluoromethyl-phenyl)-thiazole and commercially available 4-mercapto-benzonitrile.

C23H20F3N3O2S2 (491.09), MS (ESI): 492.2 (M+H⁺)

Example 15

3-{4-[4-Butyl-2-(4-trifluoromethyl-phenyl)-thiazol-5-ylmethoxy]-2-trifluoromethyl-phenyl}-4H-[1,2,4]oxadiazol-5-one

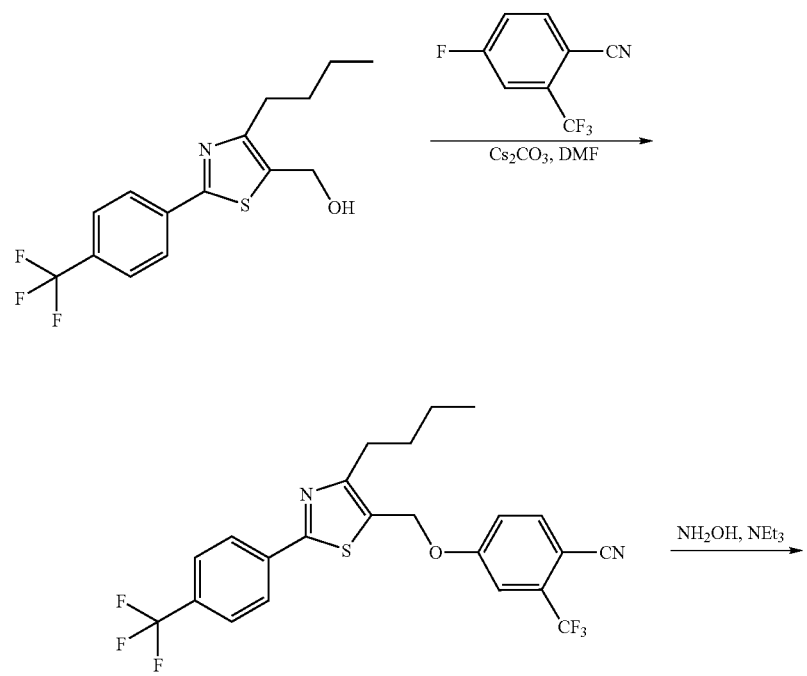

-continued

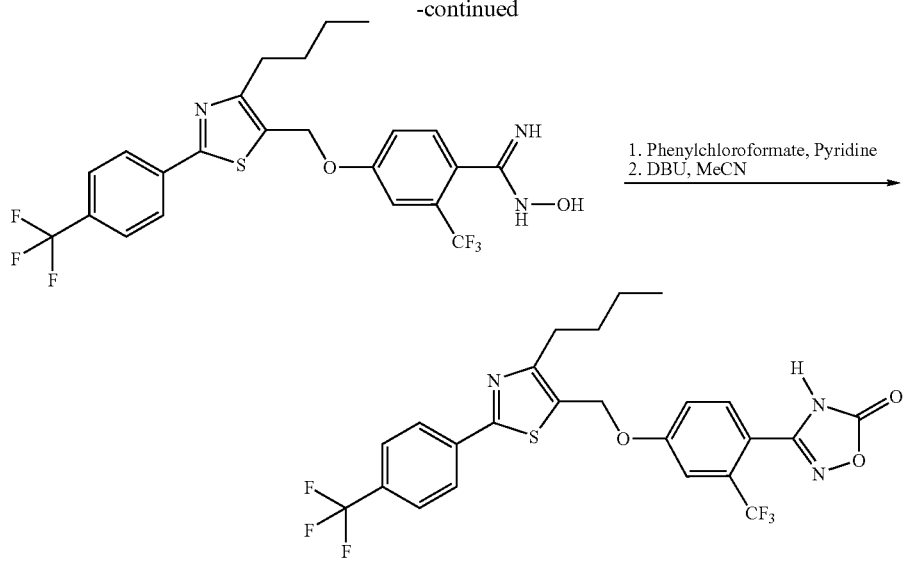

1. Phenylchloroformate, Pyridine
2. DBU, MeCN

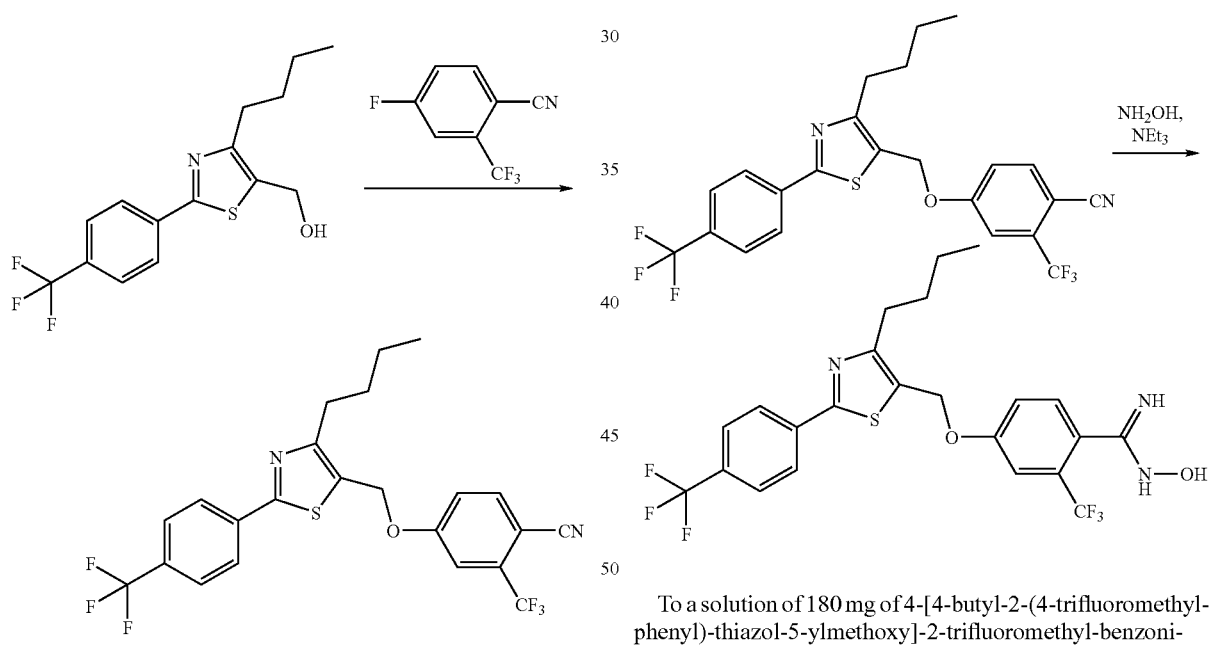

4-[4-Butyl-2-(4-trifluoromethyl-phenyl)-thiazol-5-ylmethoxy]-2-trifluoromethyl-benzonitrile 4-[4-Butyl-2-(4-trifluoromethyl-phenyl)-thiazol-5-ylmethoxy]-N-hydroxy-2-trifluoromethyl-benzamidine To a solution of 100 mg of 4-fluoro-2-trifluoromethyl benzonitrile in 5 ml of anhydrous dimethylformamide was added 200 mg of [4-butyl-2-(4-trifluoromethyl-phenyl)-thiazol-5-yl]-methanol and 0.49 g of cesium carbonate. The resulting mixture was stirred at room temperature overnight, poured onto water and extracted with heptane 1/ethyl acetate 3. The organic extracts were dried over magnesium sulfate, filtered, and concentrated under reduced pressure. The crude product was purified by column chromatography on silica gel (heptane 4/ethyl acetate 1) to give 180 mg of 4-[4-butyl-2-(4-trifluoromethyl-phenyl)-thiazol-5-ylmethoxy]-2-trifluoromethyl-benzonitrile.

C23H18F6N2OS (484.10), MS (ESI): 485 (M+H$^+$).

To a solution of 180 mg of 4-[4-butyl-2-(4-trifluoromethyl-phenyl)-thiazol-5-ylmethoxy]-2-trifluoromethyl-benzonitrile in 5 mL of tetrahydrofuran and 10 ml of methanol was added 267 mg of hydroxylamine hydrochloride followed by 0.55 mL of triethylamine. The resulting mixture was heated to 60° C. overnight. The solvents were removed in vacuo, the resulting residue was poured into water and extracted with ethylacetate. The organic extracts were dried over magnesium sulfate, filtered, and concentrated under reduced pressure. The crude product was purified by column chromatography on silica gel (heptane 1/ethyl acetate 1) to give 90 mg of 4-[4-butyl-2-(4-trifluoromethyl-phenyl)-thiazol-5-ylmethoxy]-N-hydroxy-2-trifluoromethyl-benzamidine and 50 mg of 4-[4-butyl-2-(4-trifluoromethyl-phenyl)-thiazol-5-ylmethoxy]-2-trifluoromethyl-benzamide.

C23H21F6N3O2S (517.49), MS (ESI): 518 (M+H$^+$).

3-{4-[4-Butyl-2-(4-trifluoromethyl-phenyl)-thiazol-5-ylmethoxy]-2-trifluoromethyl-phenyl}-4H-[1,2,4]oxadiazol-5-one

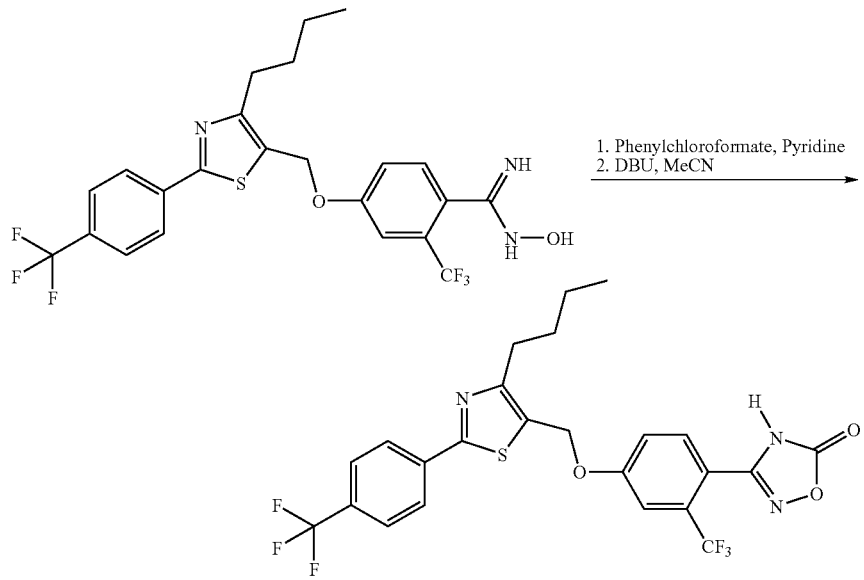

To a solution of 89.3 mg of 4-[4-butyl-2-(4-trifluoromethyl-phenyl)-thiazol-5-ylmethoxy]-N-hydroxy-2-trifluoromethyl-benzamidine in 2 ml of anhydrous dichloromethane were added 92 µl pyridine followed by 21.6 µl phenylchloroformate dropwise. The resulting mixture was stirred at room temperature for 1 h. The solvent was removed in vacuo. To a solution of the resulting residue in 2.5 ml of acetonitrile was added 88 µl of 1,8-diazabicyclo[5.4.0]undec-7-ene. The mixture was stirred under microwave heating at 180° C. for 10 minutes (or stirred at room temperature overnight). The solvent was removed in vacuo and the crude product was purified by column chromatography on silica gel (heptane 1/ethyl acetate 1 then dichloromethane 95/methanol 5 followed by another column with dichloromethane 90/acetone 10) to give 65 mg of 3-{4-[4-butyl-2-(4-trifluoromethyl-phenyl)-thiazol-5-ylmethoxy]-2-trifluoromethyl-phenyl}-4H-[1,2,4]oxadiazol-5-one.

C24H19F6N3O3S (543.10), MS (ESI): 544.4 (M+H$^+$).

Example 16

3-{4-[4-Butyl-2-(4-trifluoromethyl-phenyl)-thiazol-5-ylmethoxy]-2-methyl-phenyl}-4H-[1,2,4]oxadiazol-5-one

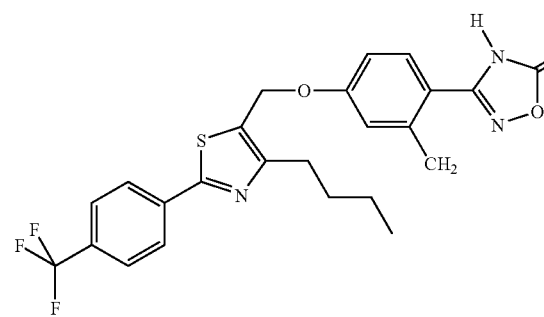

According to the method described in Example 15, 3-{4-[4-Butyl-2-(4-trifluoromethyl-phenyl)-thiazol-5-ylmethoxy]-2-methyl-phenyl}-4H-[1,2,4]oxadiazol-5-one was obtained from [4-butyl-2-(4-trifluoromethyl-phenyl)-thiazole-5-yl]-methanol and commercially available 4-fluoro-2-methyl-benzonitrile.

C24H22F3N3O3S (489.13), MS (ESI): 490.4 (M+H$^+$)

Example 17

3-{2-Bromo-4-[4-butyl-2-(4-trifluoromethyl-phenyl)-thiazol-5-ylmethoxy]-phenyl}-4H-[1,2,4]oxadiazol-5-one

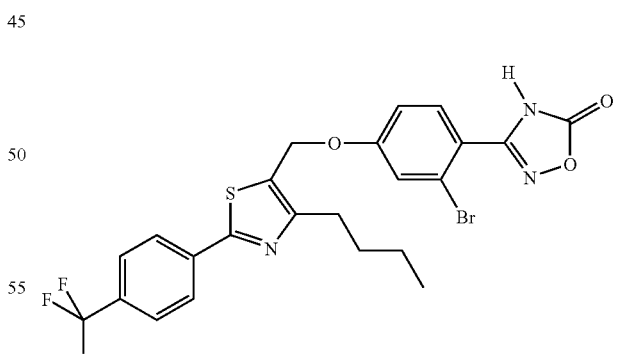

According to the method described in Example 15, 3-{2-bromo-4-[4-butyl-2-(4-trifluoromethyl-phenyl)-thiazol-5-ylmethoxy]-phenyl}-4H-[1,2,4]oxadiazol-5-one was obtained from [4-butyl-2-(4-trifluoromethyl-phenyl)-thiazole-5-yl]-methanol and commercially available 2-bromo-4-fluoro-benzonitrile.

C23H19BrF3N3O3S (553.03), MS (ESI): 554.2 (M+H$^+$)

Example 18

3-{4-[4-Butyl-2-(4-trifluoromethyl-phenyl)-thiazol-5-ylmethoxy]-2-methoxy-phenyl}-4H-[1,2,4]oxadiazol-5-one

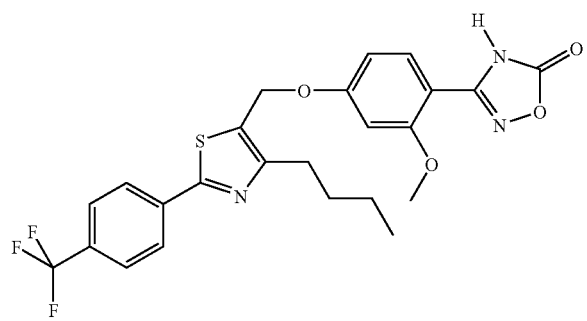

According to the method described in Example 15, 3-{4-[4-butyl-2-(4-trifluoromethyl-phenyl)-thiazol-5-yl-methoxy]-2-methoxy-phenyl}-4H-[1,2,4]oxadiazol-5-one was obtained from [4-butyl-2-(4-trifluoromethyl-phenyl)-thiazole-5-yl]-methanol and commercially available 4-fluoro-2-methoxy-benzonitrile.

C24H22F3N3O4S (505.12), MS (ESI): 506.3 (M+H⁺)

Example 19

3-{4-[4-But-3-enyl-2-(4-trifluoromethyl-phenyl)-thiazol-5-ylmethoxy]-2-chloro-phenyl}-4H-[1,2,4]oxadiazol-5-one

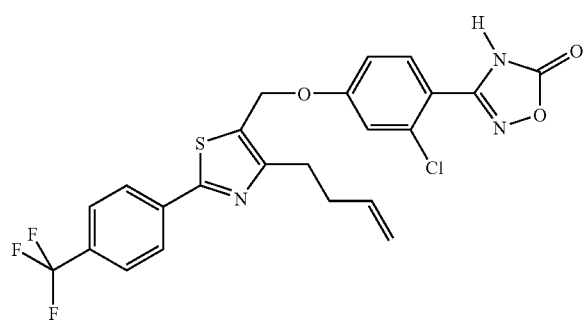

According to the method described in Example 15, 3-{4-[4-but-3-enyl-2-(4-trifluoromethyl-phenyl)-thiazol-5-yl-methoxy]-2-chloro-phenyl}-4H-[1,2,4]oxadiazol-5-one was obtained from [4-but-3-enyl-2-(4-trifluoromethyl-phenyl)-thiazol-5-yl]-methanol and commercially available 4-fluoro-2-chloro-benzonitrile.

C23H17ClF3N3O3S (507.06), MS (ESI): 508 (M+H⁺)

Example 20

3-{2-Chloro-4-[4-(4-hydroxy-butyl)-2-(4-trifluoromethyl-phenyl)-thiazol-5-ylmethoxy]-phenyl}-4H-[1,2,4]oxadiazol-5-one

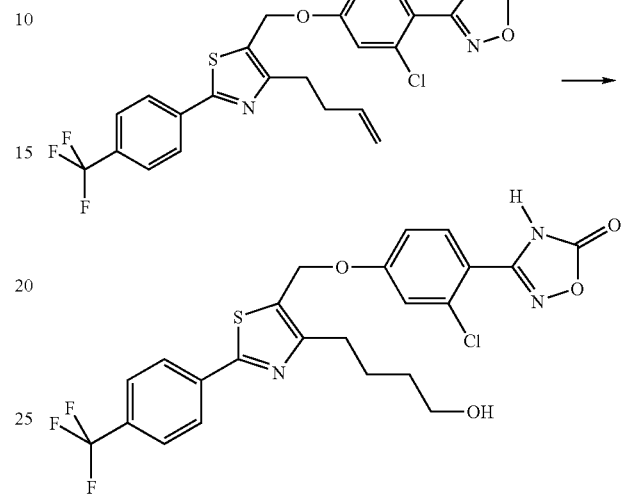

To a solution of 50 mg of 3-{4-[4-but-3-enyl-2-(4-trifluoromethyl-phenyl)-thiazol-5-ylmethoxy]-2-chloro-phenyl}-4H-[1,2,4]oxadiazol-5-one in 2 ml of tetrahydrofuran at 0° C. was added 0.3 ml of a 2M solution of borane-methylsulfide complex in tetrahydrofuran. The resulting mixture was stirred allowing it to warm up to room temperature than stirred at room temperature for 30 minutes. After cooling to 0° C., 0.1 ml of a 5M aqueous solution of sodium hydroxide and 0.1 ml of a 30% aqueous solution of hydrogen peroxide were added. The resulting mixture was stirred allowing it to warm up to room temperature over 1 hour. It was then poured into water, extracted with ethyl acetate, dried over magnesium sulfate, filtered and concentrated under reduced pressure. The crude product was purified by column chromatography on silica gel (gradient of dichloromethane/methanol from 100/0 to 95/5) followed by crystallization from dichloromethane/pentane to give 28 mg of 3-{2-chloro-4-[4-(4-hydroxy-butyl)-2-(4-trifluoromethyl-phenyl)-thiazol-5-ylmethoxy]-phenyl}-4H-[1,2,4]oxadiazol-5-one.

C23H19ClF3N3O4S (525.07), MS (ESI): 526.2 (M+H⁺)

Example 21

3-{2-Chloro-4-[4-(3,4-dihydroxy-butyl)-2-(4-trifluoromethyl-phenyl)-thiazol-5-ylmethoxy]-phenyl}-4H-[1,2,4]oxadiazol-5-one

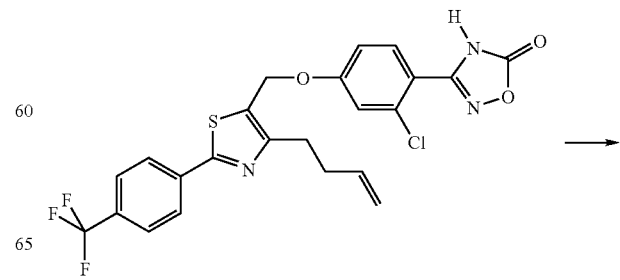

-continued

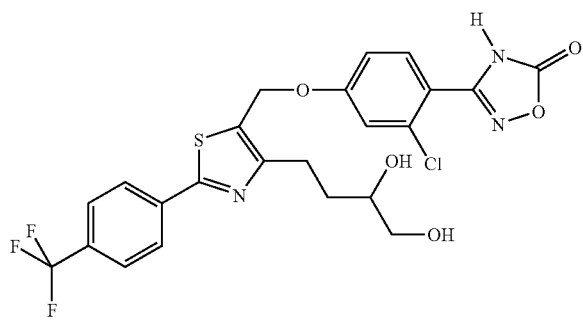

To a mixture of 189 mg of 3-{4-[4-but-3-enyl-2-(4-trifluoromethyl-phenyl)-thiazol-5-ylmethoxy]-2-chloro-phenyl}-4H-[1,2,4]oxadiazol-5-one in 0.4 ml of tetrahydrofuran, 0.2 ml of water and 0.4 ml of tert-butanol were added 0.05 ml of a 25% solution of osmium tetroxide in tert-butanol and 76 mg of N-methyl morpholine oxide. The resulting mixture was stirred at room temperature for 24 hours. It was then poured into a saturated aqueous solution of sodium hydrogenocarbonate, extracted with dichloromethane, dried over magnesium sulfate, filtered and concentrated under reduced pressure. The crude product was purified by column chromatography on silica gel (gradient of dichloromethane/methanol from 100/0 to 95/5) to give 32 mg of 3-{2-chloro-4-[4-(3,4-dihydroxy-butyl)-2-(4-trifluoromethyl-phenyl)-thiazol-5-ylmethoxy]-phenyl}-4H-[1,2,4]oxadiazol-5-one.

C23H19ClF3N3O5S (541.06), MS (ESI): 542.2 (M+H$^+$)

Example 22

5-[4-Butyl-2-(4-trifluoromethyl-phenyl)-thiazol-5-ylmethoxy]-2-(5-oxo-4,5-dihydro-[1,2,4]oxadiazol-3-yl)-benzonitrile To a solution of 100 mg of 3-{2-bromo-4-[4-butyl-2-(4-trifluoromethyl-phenyl)-thiazol-5-ylmethoxy]-phenyl}-4H-[1,2,4]oxadiazol-5-one in 4 ml of pyridine was added 29 mg of copper cyanide. The resulting mixture was stirred under microwave heating at 21° C. for 10 minutes, then concentrated under reduced pressure. The residue was taken into ethyl acetate, washed with a pH 9 aqueous solution of ammonia, dried over magnesium sulfate, filtered and concentrated under reduced pressure. The crude product was purified by preparative thin layer chromatography on silica gel (dichloromethane 95/methanol 5) and precipitated from ethyl acetate/diisopropyl ether/pentane to give 9.5 mg of 5-[4-butyl-2-(4-trifluoromethyl-phenyl)-thiazol-5-ylmethoxy]-2-(5-oxo-4,5-dihydro-[1,2,4]oxadiazol-3-yl)-benzonitrile

C24H19F3N4O3S (500.11), MS (ESI): 501.3 (M+H$^+$)

Example 23

3-{4-[4-Butyl-2-(4-trifluoromethyl-phenyl)-thiazol-5-ylmethoxy]-2-methylsulfanyl-phenyl}-4H-[1,2,4]oxadiazol-5-one -continued

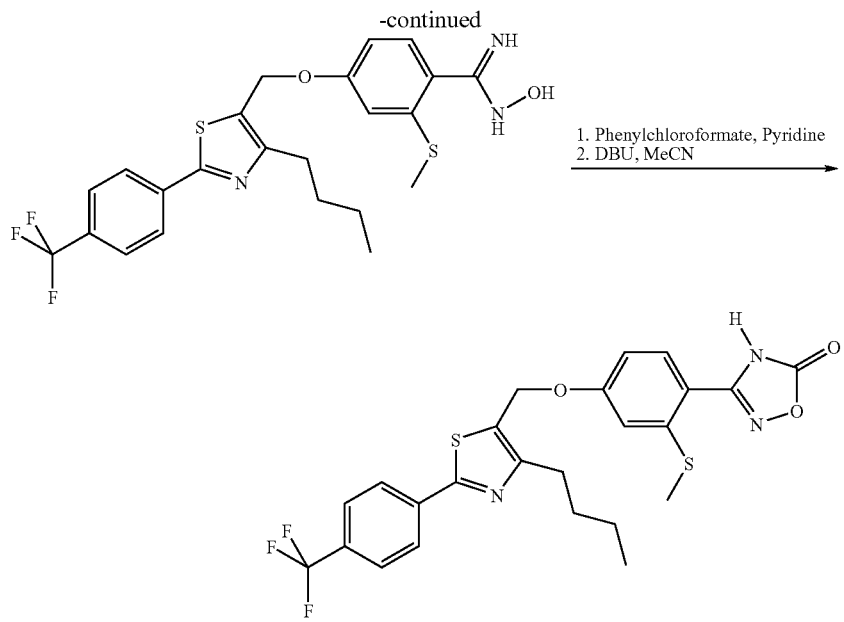

1. Phenylchloroformate, Pyridine
2. DBU, MeCN

To a solution of 50 mg of 4-[4-butyl-2-(4-trifluoromethyl-phenyl)-thiazol-5-ylmethoxy]-2-fluoro-benzonitrile (prepared according to the method described in example 1) in 10 ml of dimethylformamide was added 121 mg of sodium thiomethoxide. The resulting mixture was stirred at room temperature overnight, then poured into water, extracted with diisopropyl ether. The combined organic extracts were washed with water, dried over magnesium sulfate, filtered and concentrated under reduced pressure. The crude product was purified by crystallization from diisopropyl ether/heptane to give 350 mg of 4-[4-butyl-2-(4-trifluoromethyl-phenyl)-thiazol-5-ylmethoxy]-2-methylsulfanyl-benzonitrile, which was transformed into 3-{4-[4-butyl-2-(4-trifluoromethyl-phenyl)-thiazol-5-ylmethoxy]-2-methylsulfanyl-phenyl}-4H-[1,2,4]oxadiazol-5-one according to the method described in example 1.

C24H22F3N3O3S2 (521.10), MS (ESI): 522.3 (M+H$^+$)

Example 24

3-{4-[4-Butyl-2-(4-trifluoromethyl-phenyl)-thiazol-5-ylmethoxy]-2-methylsulfinyl-phenyl}-4H-[1,2,4]oxadiazol-5-one

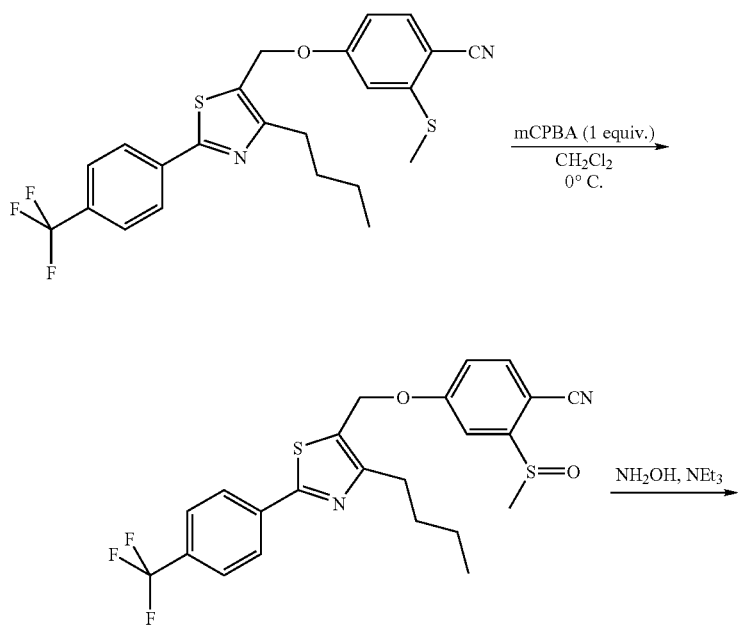

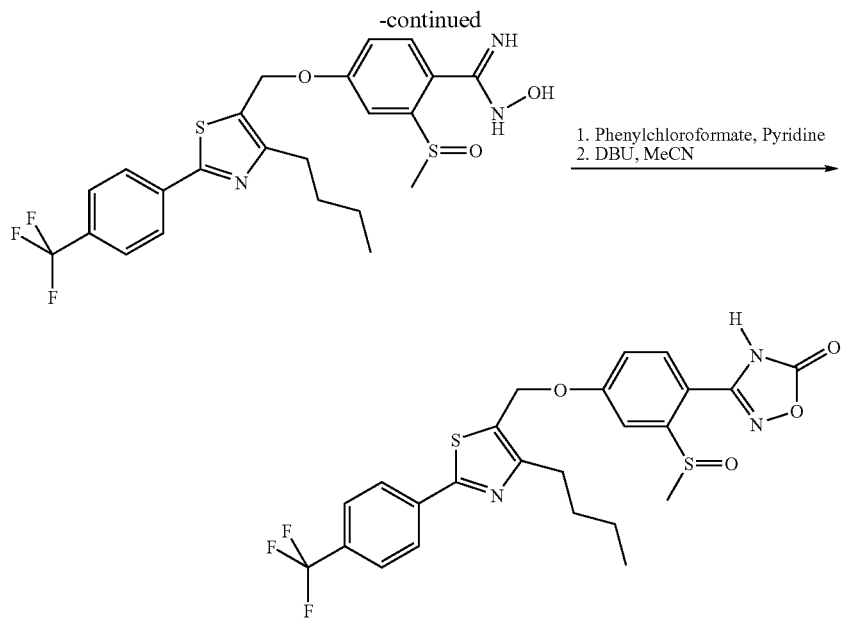

To a solution of 200 mg of 4-[4-butyl-2-(4-trifluoromethyl-phenyl)-thiazol-5-ylmethoxy]-2-methylsulfanyl-benzonitrile (prepared according to the method described in example 23) in 4 ml of dichloromethane at 0° C. was added 74 mg of meta-chloroperbenzoic acid. The resulting mixture was stirred at 0° C. for 2 hours then kept in the freezer overnight. A saturated aqueous solution of sodium hydrogenocarbonate was added and the organic layer was separated. The aqueous layer was extracted with dichloromethane. The combined extracts were dried over magnesium sulfate, filtered and concentrated under reduced pressure to give 203 mg of 4-[4-butyl-2-(4-trifluoromethyl-phenyl)-thiazol-5-ylmethoxy]-2-methylsulfinyl-benzonitrile, which was transformed into 3-{4-[4-butyl-2-(4-trifluoromethyl-phenyl)-thiazol-5-ylmethoxy]-2-methylsulfinyl-phenyl}-4H-[1,2,4]oxadiazol-5-one according to the method described in example 1.

C24H22F3N3O4S2 (537.10), MS (ESI): 538.3 (M+H$^+$)

Example 25

3-{4-[4-Butyl-2-(4-trifluoromethyl-phenyl)-thiazol-5-ylmethoxy]-2-methanesulfonyl-phenyl}-4H-[1,2,4]oxadiazol-5-one

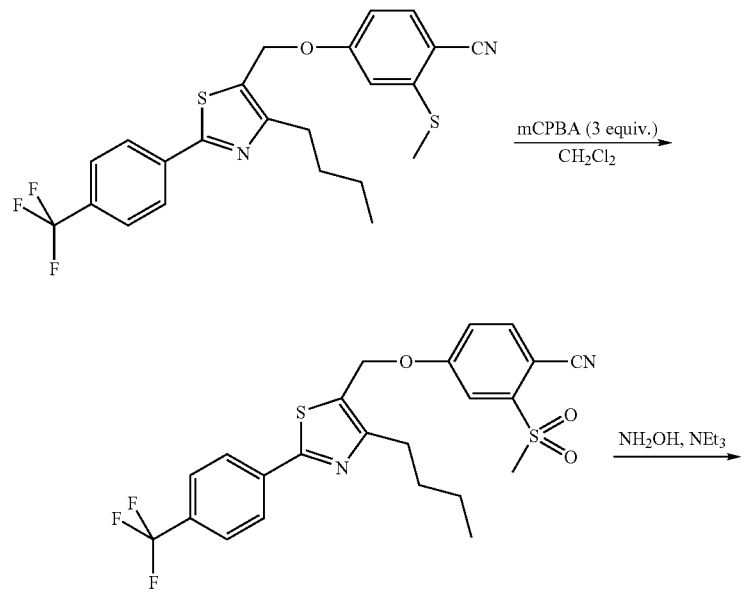

-continued

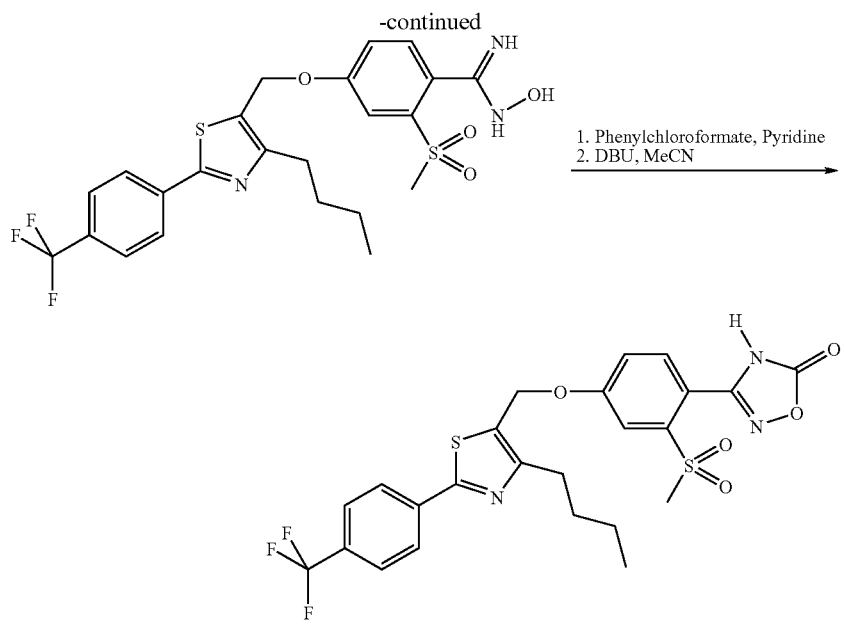

1. Phenylchloroformate, Pyridine
2. DBU, MeCN

To a solution of 200 mg of 4-[4-butyl-2-(4-trifluoromethyl-phenyl)-thiazol-5-ylmethoxy]-2-methylsulfanyl-benzonitrile (prepared according to the method described in example 23) in 20 ml of dichloromethane at 0° C. was added 149 mg of meta-chloroperbenzoic acid. The resulting mixture was stirred at 0° C. for 2 hours than 1 hour at room temperature. After adding another 75 mg of meta-chloroperbenzoic, the reaction mixture was stirred for 3 hours at room temperature. A saturated aqueous solution of sodium hydrogenocarbonate was added and the organic layer was separated. The aqueous layer was extracted with dichloromethane. The combined extracts were dried over magnesium sulfate, filtered and concentrated under reduced pressure to give 210 mg of 4-[4-butyl-2-(4-trifluoromethyl-phenyl)-thiazol-5-ylmethoxy]-2-methanesulfonyl-benzonitrile, which was transformed into 3-{4-[4-butyl-2-(4-trifluoromethyl-phenyl)-thiazol-5-ylmethoxy]-2-methanesulfonyl-phenyl}-4H-[1,2,4]oxadiazol-5-one according to the method described in example 1.

C24H22F3N3O5S2 (553.09), MS (ESI): 554.1 (M+H$^+$)

Example 26

3-{4-[4-Butyl-2-(4-trifluoromethyl-phenyl)-thiazol-5-ylmethanesulfinyl]-phenyl}-4H-[1,2,4]oxadiazol-5-one

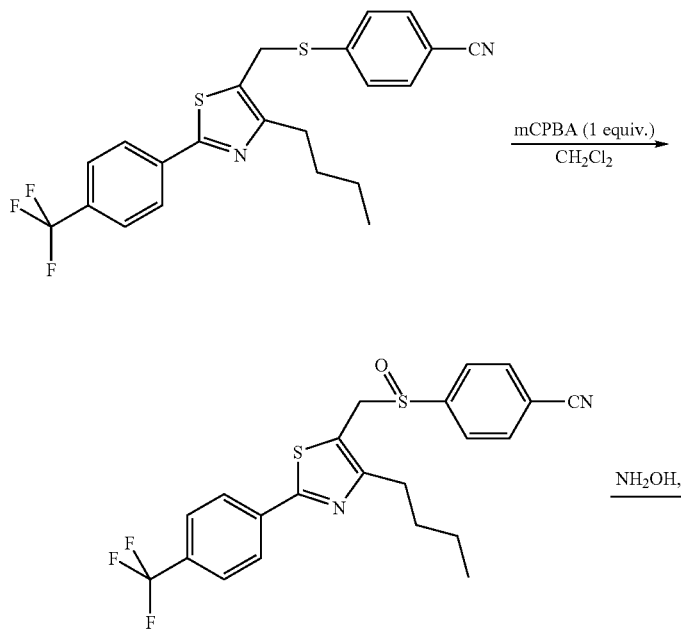

-continued

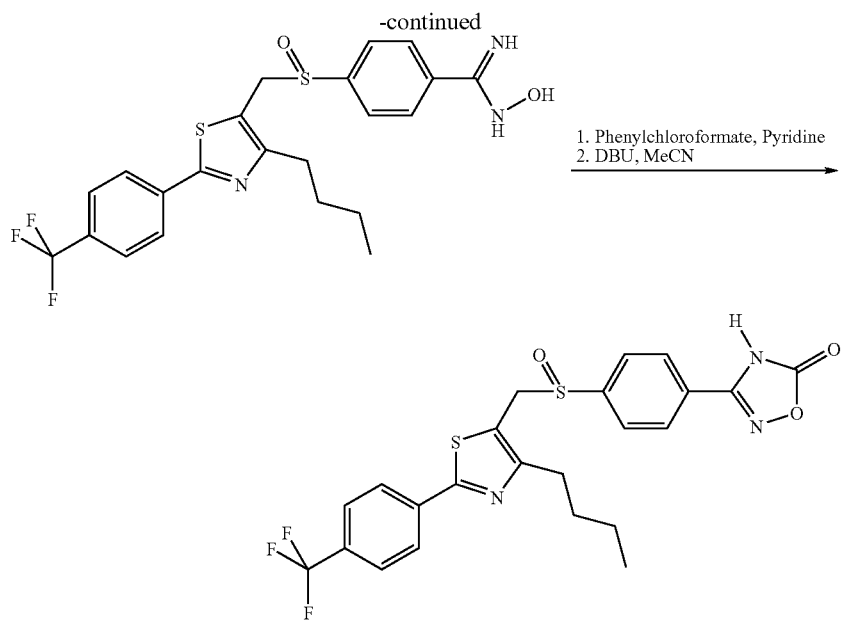

1. Phenylchloroformate, Pyridine
2. DBU, MeCN

To a solution of 200 mg of 4-[4-butyl-2-(4-trifluoromethyl-phenyl)-thiazol-5-ylmethylsulfanyl]-benzonitrile (prepared according to the method described in example 14) in 4 ml of dichloromethane at 0° C. was added 80 mg of meta-chloroperbenzoic acid. The resulting mixture was stirred at 0° C. for 5 hours, at room temperature for 2 hours than kept in the fridge overnight. A saturated aqueous solution of sodium hydrogenocarbonate was added and the organic layer was separated. The aqueous layer was extracted with dichloromethane. The combined extracts were dried over magnesium sulfate, filtered and concentrated under reduced pressure. The crude product was purified by column chromatography on silica gel (gradient of 1 to 4% acetone/dichloromethane) to give 185 mg of 4-[4-butyl-2-(4-trifluoromethyl-phenyl)-thiazol-5-ylmethylsulfinyl]-benzonitrile, which was transformed into 3-{4-[4-butyl-2-(4-trifluoromethyl-phenyl)-thiazol-5-ylmethanesulfinyl]-phenyl}-4H-[1,2,4]oxadiazol-5-one according to the method described in example 1.

$C_{23}H_{20}F_3N_3O_3S_2$ (507.09), MS (ESI): 508 (M+H$^+$)

Example 27

3-{4-[4-Butyl-2-(4-trifluoromethyl-phenyl)-thiazol-5-ylmethylsulfonyl]-phenyl}-4H [1,2,4]oxadiazol-5-one

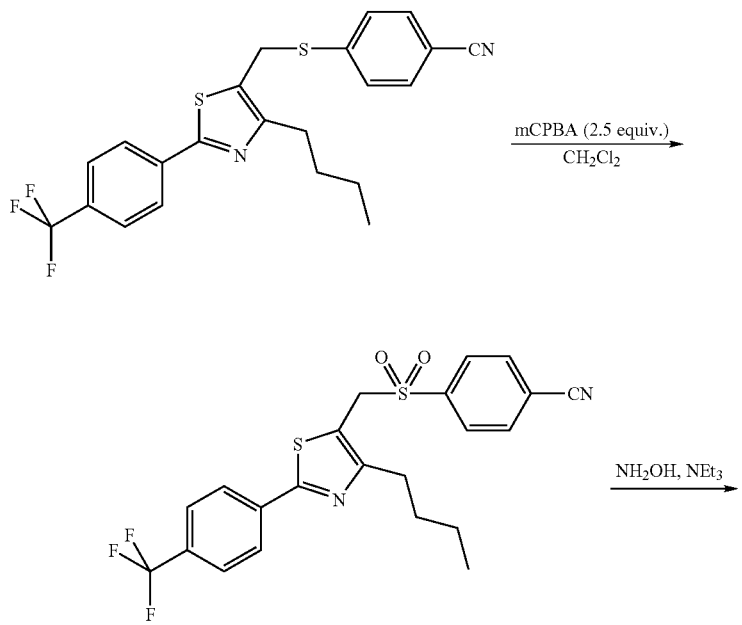

mCPBA (2.5 equiv.)
CH$_2$Cl$_2$

NH$_2$OH, NEt$_3$

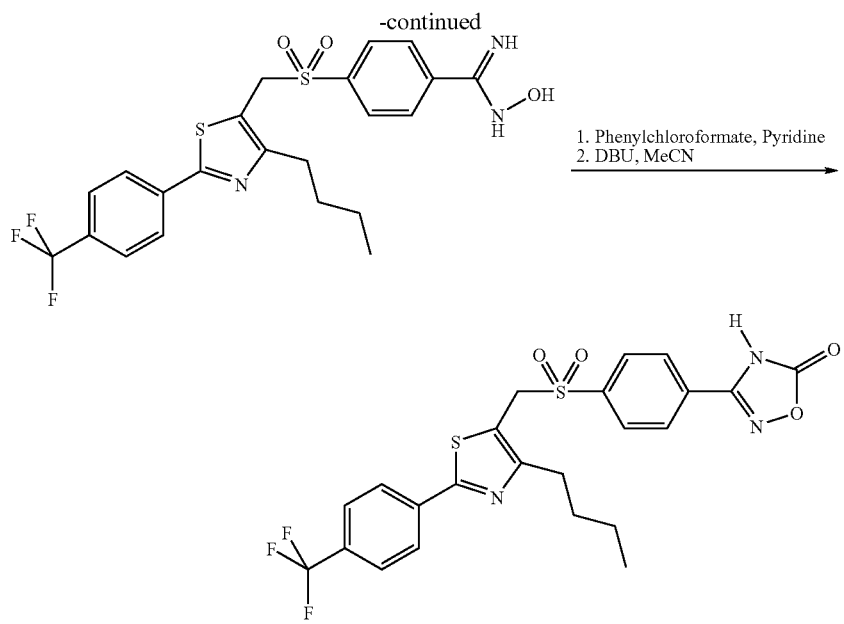

1. Phenylchloroformate, Pyridine
2. DBU, MeCN

To a solution of 200 mg of 4-[4-butyl-2-(4-trifluoromethyl-phenyl)-thiazol-5-ylmethylsulfanyl]-benzonitrile (prepared according to the method described in example 14) in 4 ml of dichloromethane at 0° C. was added 200 mg of meta-chloroperbenzoic acid. The resulting mixture was stirred at 0° C. for 5 hours. A saturated aqueous solution of sodium hydrogenocarbonate was added and the organic layer was separated. The aqueous layer was extracted with dichloromethane. The combined extracts were dried over magnesium sulfate, filtered and concentrated under reduced pressure to give 225 mg of 4-[4-butyl-2-(4-trifluoromethyl-phenyl)-thiazol-5-ylmethylsulfonyl]-benzonitrile, which was transformed into 3-{4-[4-butyl-2-(4-trifluoromethyl-phenyl)-thiazol-5-ylmethanesulfonyl]-phenyl}-4H-[1,2,4]oxadiazol-5-one according to the method described in example 1.

C23H20F3N3O4S2 (523.08), MS (ESI): 522 (M−H+)

Example 28

3-{4-[4-Butyl-2-(4-trifluoromethyl-phenyl)-thiazol-5-ylmethoxymethyl]-2-fluoro-phenyl}-4H-[1,2,4]oxadiazol-5-one

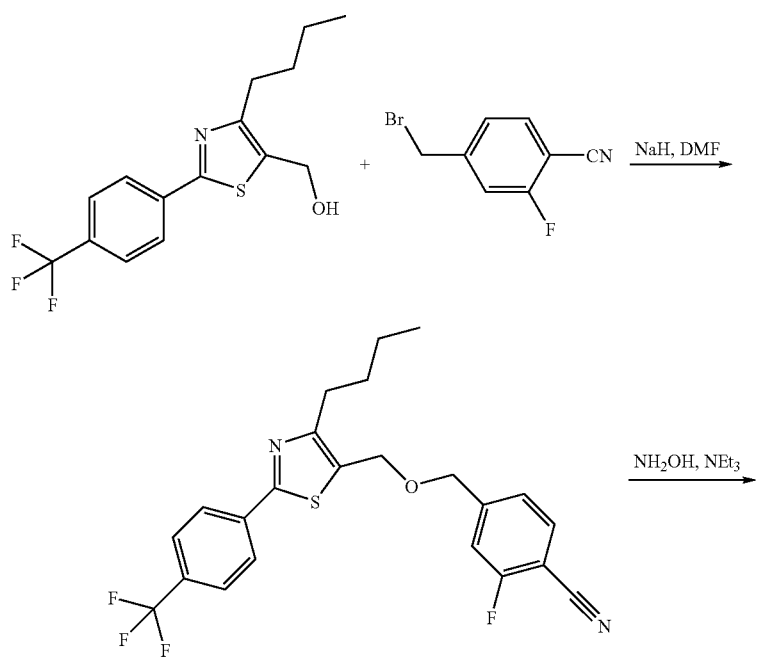

-continued

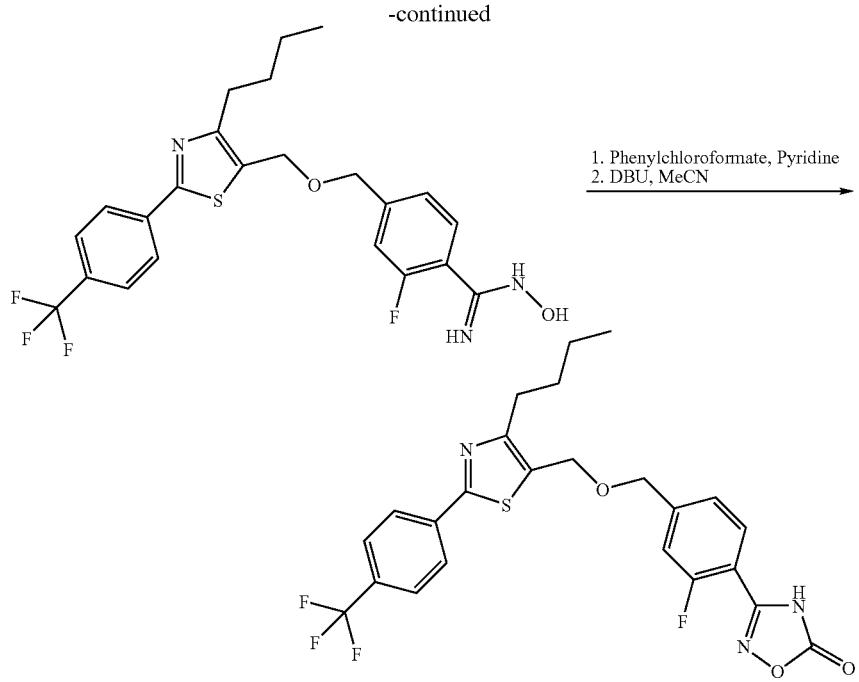

1. Phenylchloroformate, Pyridine
2. DBU, MeCN

To a solution of 2.255 g of [4-butyl-2-(4-trifluoromethyl-phenyl)-thiazole-5-yl]-methanol in 25 ml of dimethylformamide was added 0.286 g of a 60% dispersion of sodium hydride in mineral oil. After stirring for 15 minutes, 3 g of 4-bromomethyl-2-fluoro-benzonitrile was added. The resulting mixture was stirred at room temperature overnight, then poured into water, extracted with diisopropyl ether. The combined organic extracts were washed with water, dried over magnesium sulfate, filtered and concentrated under reduced pressure. The crude product was purified by column chromatography on silica gel (heptane 95/ethyl acetate 5) to give 0.6 g of 4-[4-butyl-2-(4-trifluoromethyl-phenyl)-thiazol-5-yl-methoxymethyl]-2-fluoro-benzonitrile, which was transformed into 3-{4-[4-butyl-2-(4-trifluoromethyl-phenyl)-thiazol-5-ylmethoxymethyl]-2-fluoro-phenyl}-4H-[1,2,4]oxadiazol-5-one according to the method described in example 1.

C24H21F4N3O3S (507.12), MS (ESI): 508.3 (M+H+)

Example 29

3-{4-[4-Methyl-2-(4-trifluoromethyl-phenyl)-thiazol-5-ylmethoxymethyl]-phenyl}-4H-[1,2,4]oxadiazol-5-one

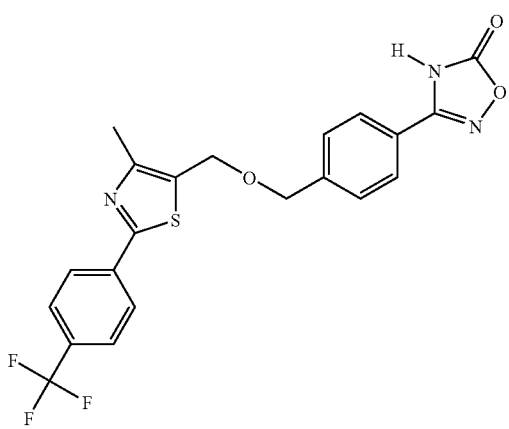

According to the method described in Example 28 4-[4-Methyl-2-(4-trifluoromethyl-phenyl)-thiazol-5-yl-methoxymethyl]-benzonitrile was obtained from [4-Methyl-2-(4-trifluoromethyl-phenyl)-thiazol-5-yl]-methanol and commercially available 4-bromomethyl-benzonitrile. 4-[4-Methyl-2-(4-trifluoromethyl-phenyl)-thiazol-5-yl-methoxymethyl]-benzonitrile was transformed into 3-{4-[4-Methyl-2-(4-trifluoromethyl-phenyl)-thiazol-5-ylmethoxymethyl]-phenyl}-4H-[1,2,4]oxadiazol-5-one according to the method described in example 1.

C21H16F3N3O3S (447.74), MS (ESI): 448 (M+H+)

Example 30

3-[4-(2-Biphenyl-4-yl-5-methyl-oxazol-4-ylmethoxy)-2-chloro-phenyl]-4H-[1,2,4]oxadiazol-5-one

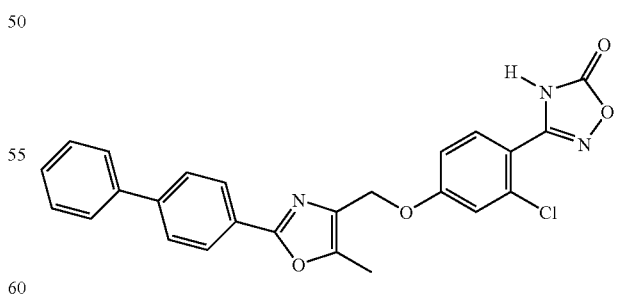

According to the method described in Example 1, 3-[4-(2-Biphenyl-4-yl-5-methyl-oxazol-4-ylmethoxy)-2-chloro-phenyl]-4H-[1,2,4]oxadiazol-5-one was obtained from 4-iodomethyl-5-methyl-2-p-biphenyloxazole and commercially available 2-chloro-4-hydroxy-benzonitrile.

C25H18ClN3O4 (459.89), MS (ESI): 460 (M+H+).

Example 31

3-{2-Chloro-4-[2-(4-methoxy-phenyl)-5-methyl-oxazol-4-ylmethoxy]-phenyl}-4H-[1,2,4]oxadiazol-5-one

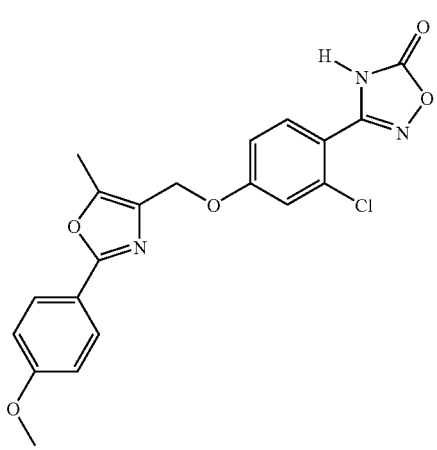

According to the method described in Example 1, 3-{2-Chloro-4-[2-(4-methoxy-phenyl)-5-methyl-oxazol-4-yl-methoxy]-phenyl}-4H-[1,2,4]oxadiazol-5-one was obtained from 4-iodomethyl-2-(4-methoxyphenyl)-5-methyloxazole and commercially available 2-Chloro-4-hydroxy-benzonitrile.

C20H16ClN3O5 (413.82), MS (ESI): 414 (M+H$^+$).

Example 32

3-(2-Chloro-4-{2-[5-methyl-2-(4-trifluoromethyl-phenyl)-thiazol-4-yl]-ethoxy}-phenyl)-4H-[1,2,4]oxadiazol-5-one

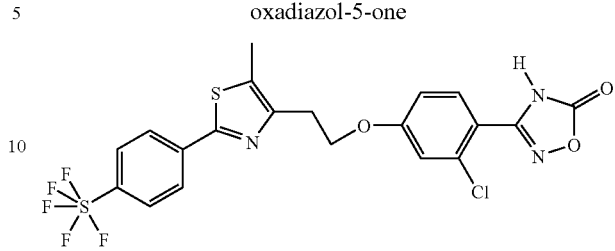

According to the method described in Example 9, 2-Chloro-4-{2-[5-methyl-2-(4-pentafluorosulfanyl-phenyl)-thiazol-4-yl]-ethoxy}-benzonitrile was obtained from 2-[5-Methyl-2-(4-pentafluorosulfanyl-phenyl)-thiazol-4-yl]-ethanol and commercially available 2-Chloro-4-hydroxy-benzonitrile. 2-Chloro-4-{2-[5-methyl-2-(4-pentafluorosulfanyl-phenyl)-thiazol-4-yl]-ethoxy}-benzonitrile was transformed into 3-(2-Chloro-4-{2-[5-methyl-2-(4-trifluoromethyl-phenyl)-thiazol-4-yl]-ethoxy}-phenyl)-4H-[1,2,4]oxadiazol-5-one according to the method described in example 1.

C20H15ClF5N3O3S2 (439.93), MS (ESI): 540 (M+H$^+$)

Example 33

3-{2-Chloro-4-[4-methoxymethyl-2-(4-trifluoromethyl-phenyl)-thiazol-5-ylmethoxy]-phenyl}-4H-[1,2,4]oxadiazol-5-one

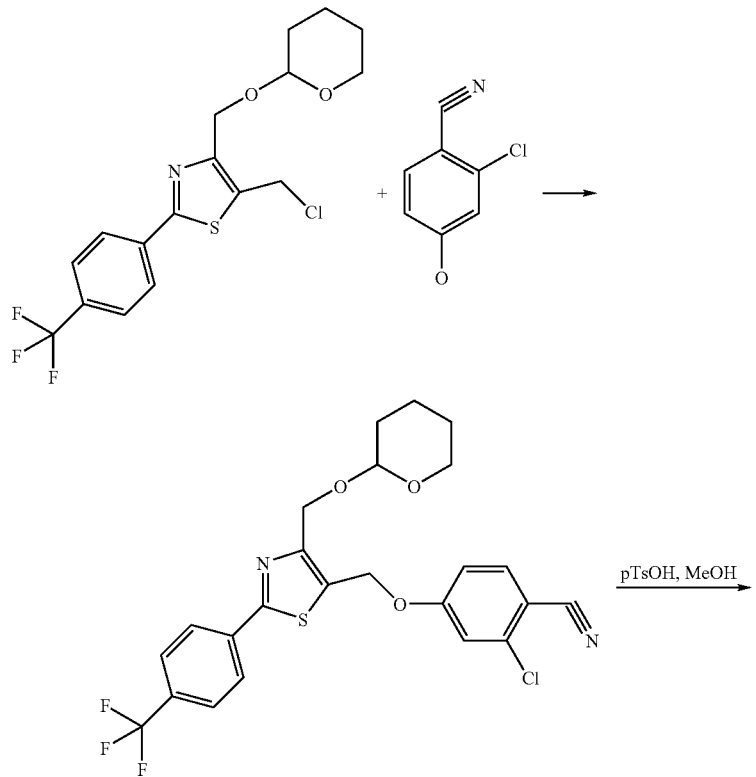

-continued
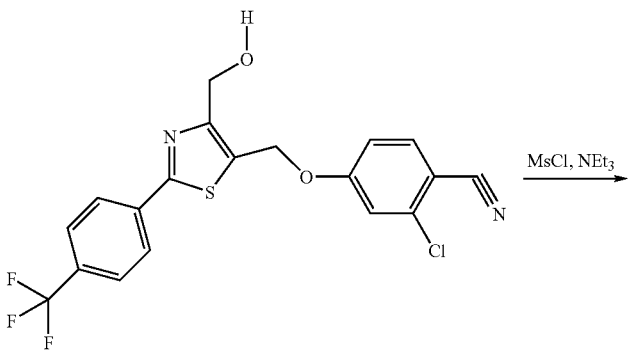
MsCl, NEt3
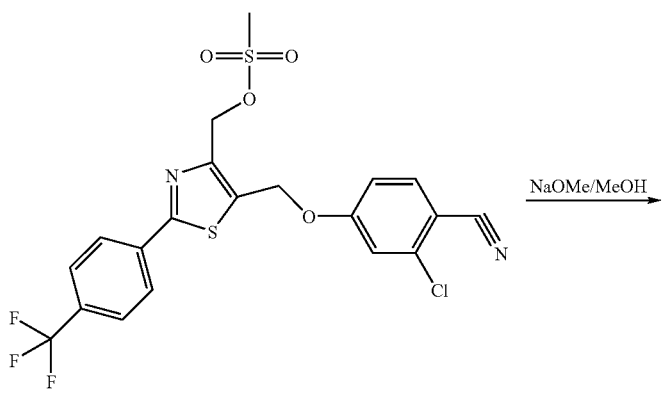
NaOMe/MeOH
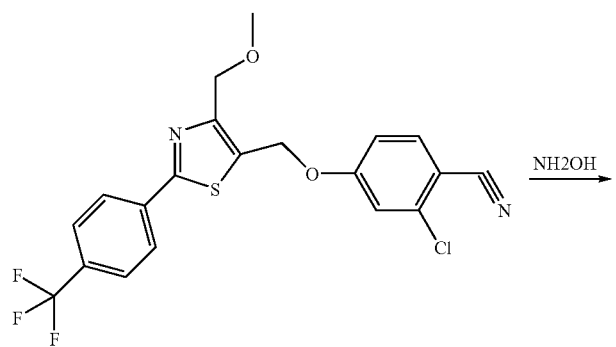
NH2OH
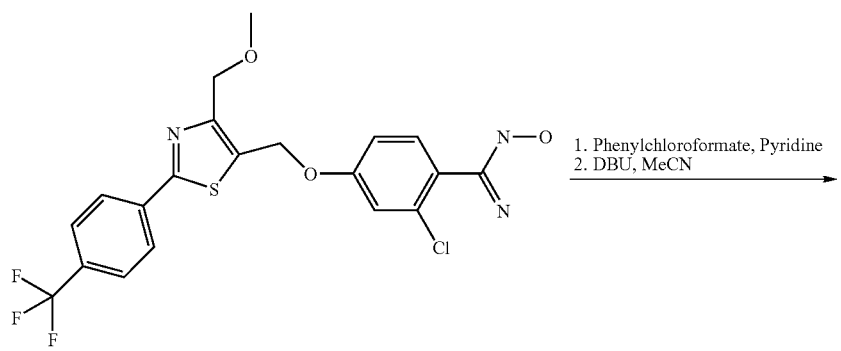
1. Phenylchloroformate, Pyridine
2. DBU, MeCN

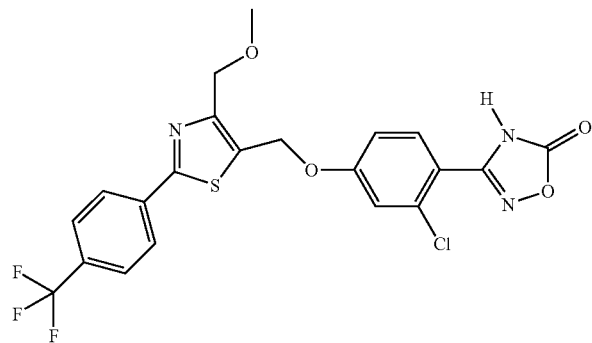

example 33

2-Chloro-4-[4-(tetrahydro-pyran-2-yloxymethyl)-2-(4-trifluoromethyl-phenyl)-thiazol-5-ylmethoxy]-benzonitrile is described in WO2002/067912) thiazole were dissolved in 100 ml dimethylformamide. 5.0 g of cesium carbonate and 1.53 g 2-Chloro-4-hydroxybenzonitrile were added and the mixture was stirred at room temperature overnight. Then 300 ml of ethylacetate were added, the mixture washed three times with saturated NaHCO3 solution and brine then dried over MgSO4. The solvent was removed in vacuo to obtain 4.1 g of crude 2-Chloro-4-[4-(tetrahydro-pyran-2-yloxymethyl)-2-(4-trifluoromethyl-phenyl)-thiazol-5-ylmethoxy]-benzonitrile as yellow oil. This material was used without further purification.

C24H20ClF3N2O3S (508.95), MS (ESI): 509.1 (M+H$^+$), 425.1 (M−THP+H+).

2-Chloro-4-[4-hydroxymethyl-2-(4-trifluoromethyl-phenyl)-thiazol-5-ylmethoxy]-benzonitrile

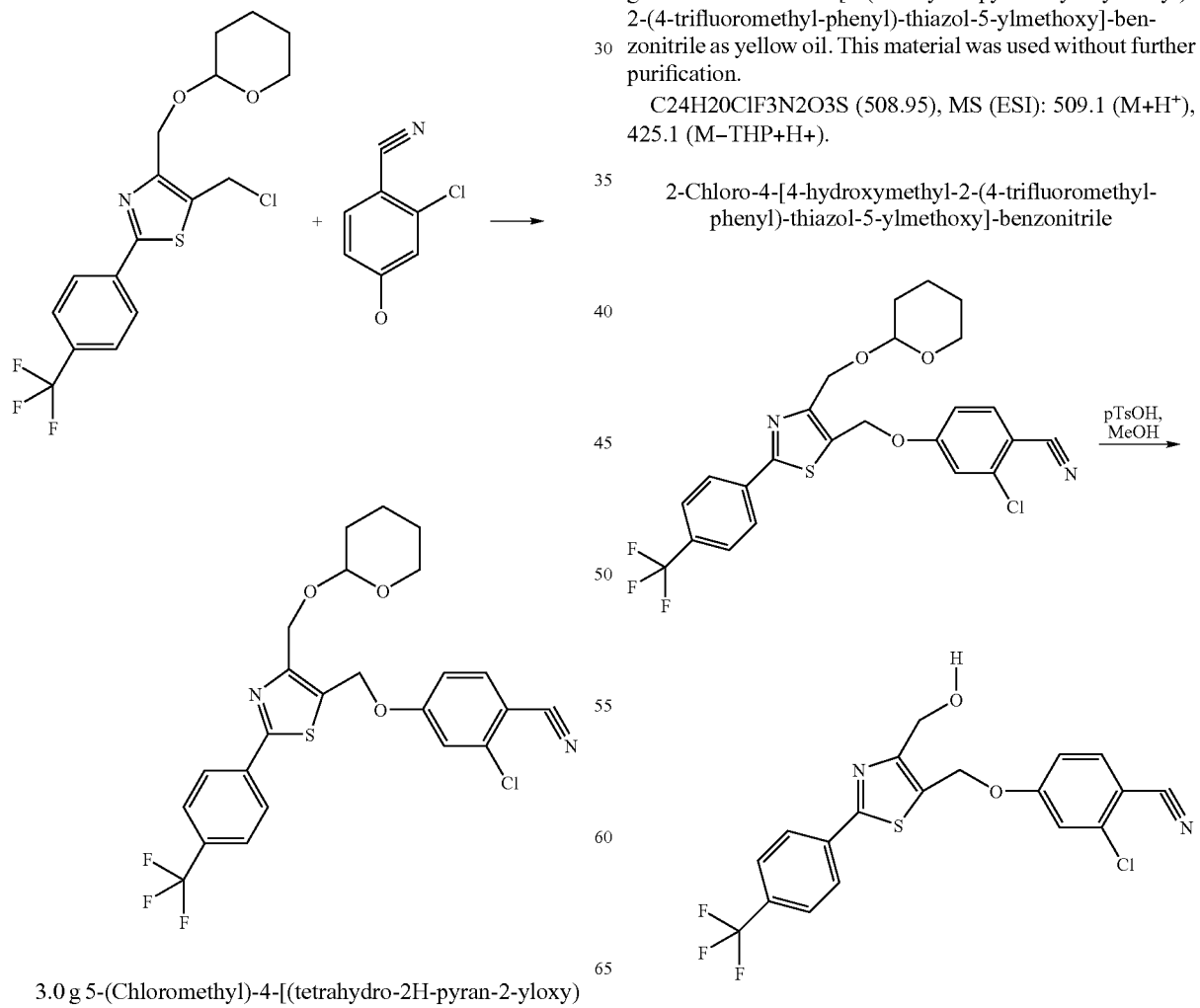

3.0 g 5-(Chloromethyl)-4-[(tetrahydro-2H-pyran-2-yloxy)methyl]-2-[4-(trifluormethyl)phenyl]-1,3-thiazole (synthesis 4.1 g 2-Chloro-4-[4-(tetrahydro-pyran-2-yloxymethyl)-2-(4-trifluoromethyl-phenyl)-thiazol-5-ylmethoxy]-benzonitrile were dissolved in 50 ml methanol. 320 mg p-toluenesulfonic acid monohydrate were added and the mixture was stirred for one hour at room temperature. The solvent was removed in vacuo and the residue was dissolved in ethylacetate and washed twice with saturated NaHCO3 solution and brine then dried over MgSO4. The solvent was removed in vacuo to obtain 3.4 g 2-Chloro-4-[4-hydroxymethyl-2-(4-trifluoromethyl-phenyl)-thiazol-5-ylmethoxy]-benzonitrile as pale yellow solid.

C19H12ClF3N2O2S (424.83), MS (ESI): 425.1 (M+H$^+$), Rf (n-heptan:Ethylacetate=1:1)=0.27.

Methanesulfonic acid 5-(3-chloro-4-cyano-phenoxymethyl)-2-(4-trifluoromethyl-phenyl)-thiazol-4-ylmethyl Ester

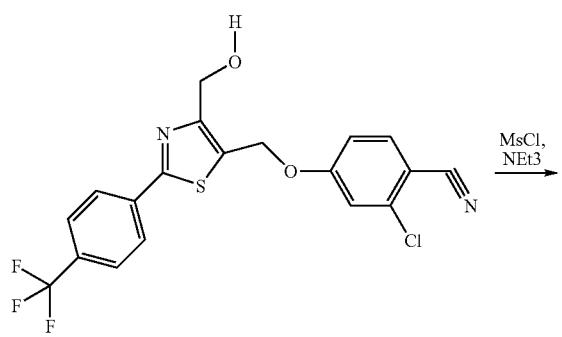

1.8 g 2-Chloro-4-[4-hydroxymethyl-2-(4-trifluoromethyl-phenyl)-thiazol-5-ylmethoxy]-benzonitrile were suspended in 50 ml dichloromethane and cooled in an ice bath. 0.39 ml methanesulfonylchloride and 0.89 ml triethylamine were added. The resulting mixture was stirred at 0° C. for one hour then washed with water and brine, dried over MgSO4. The solvent was removed in vacuo to obtain 1.0 g methanesulfonic acid 5-(3-chloro-4-cyano-phenoxymethyl)-2-(4-trifluoromethyl-phenyl)-thiazol-4-ylmethyl ester as pale yellow solid.

C20H14ClF3N2O4S2 (502.92), MS (ESI): 503.1 (M+H).

2-Chloro-4-[4-methoxymethyl-2-(4-trifluoromethyl-phenyl)-thiazol-5-ylmethyl]-benzonitrile

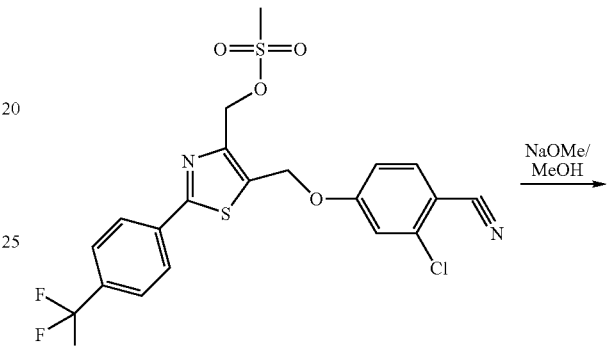

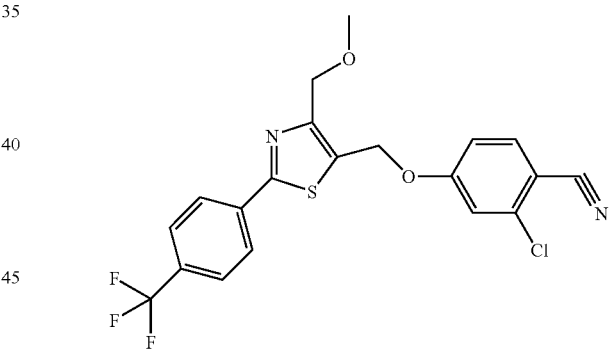

120 mg Methanesulfonic acid 5-(3-chloro-4-cyano-phenoxymethyl)-2-(4-trifluoromethyl-phenyl)-thiazol-4-ylmethyl ester were dissolved in 5 ml methanol. 12.9 mg sodium methoxide were added and the mixture stirred at 50° C. for one hour. The reaction mixture was diluted by addition of 50 ml ethyl acetate, washed with one molar hydrochloric acid then dried over MgSO4. The solvent was removed in vacuo and the residue purified by RP-HPLC to provide 30 mg of 2-chloro-4-[4-methoxymethyl-2-(4-trifluoromethyl-phenyl)-thiazol-5-ylmethoxy]-benzonitrile as lyophilisate.

C20H14ClF3N2O2S (438.86), MS (ESI): 439.1 (M+H).

3-{2-Chloro-4-[4-methoxymethyl-2-(4-trifluorom-ethyl-phenyl)-thiazol-5-ylmethoxy]-phenyl}-4H-[1,2,4]oxadiazol-5-one

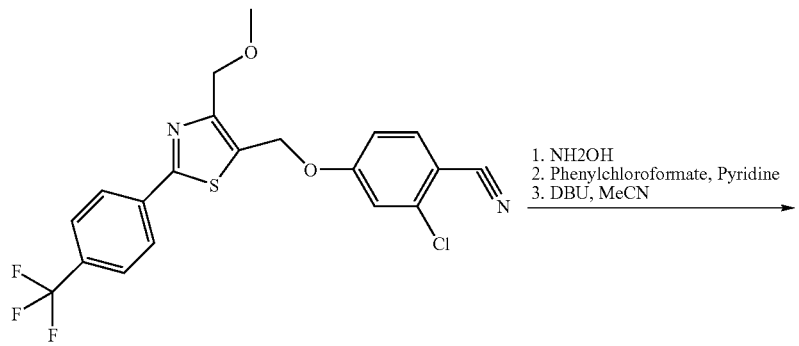

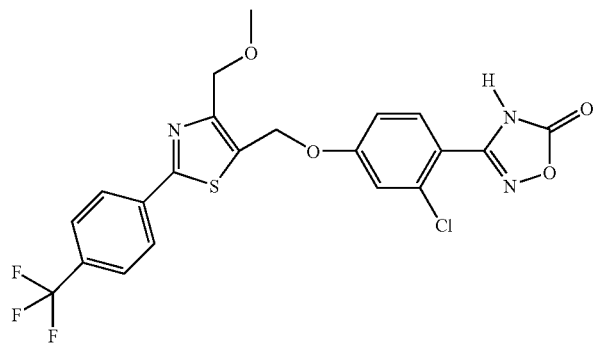

example 33

According to the method described in Example 1, 3-{2-Chloro-4-[4-methoxymethyl-2-(4-trifluoromethyl-phenyl)-thiazol-5-ylmethoxy]-phenyl}-4H-[1,2,4]oxadiazol-5-one was obtained from 2-Chloro-4-[4-methoxymethyl-2-(4-trifluoromethyl-phenyl)-thiazol-5-ylmethoxy]-benzonitrile.

C21H15ClF3N3O4S (497.88), MS (ESI): 498.3 (M+H$^+$).

Example 34

3-{2-Chloro-4-[4-(2-methoxy-ethoxymethyl)-2-(4-trifluoromethyl-phenyl)-thiazol-5-ylmethoxy]-phenyl}-4H-[1,2,4]oxadiazol-5-one 2-Chloro-4-[4-(2-methoxy-ethoxymethyl)-2-(4-trifluoromethyl-phenyl)-thiazol-5-ylmethoxy]-benzonitrile

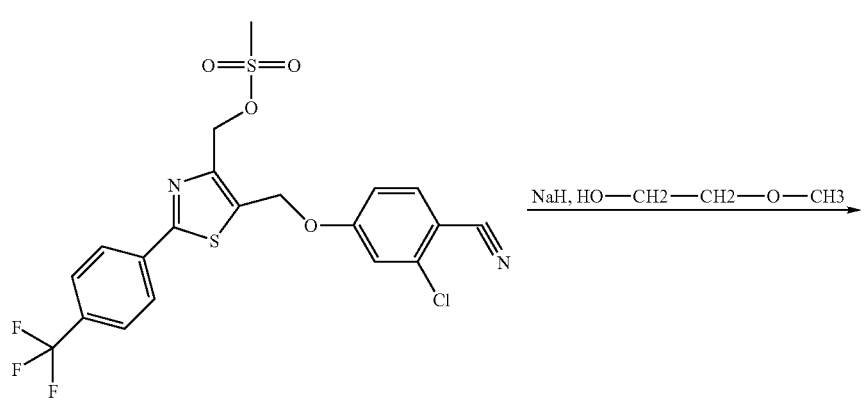

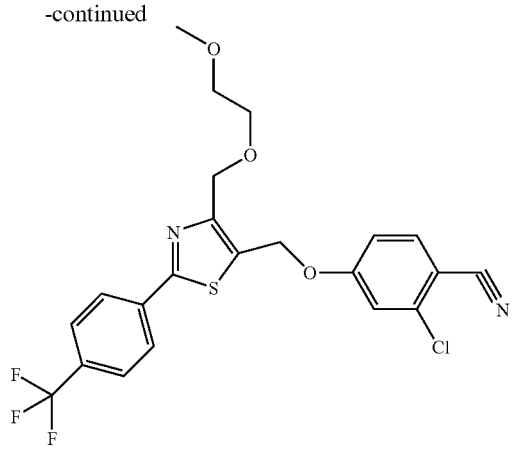

120 mg Methanesulfonic acid 5-(3-chloro-4-cyano-phenoxymethyl)-2-(4-trifluoromethyl-phenyl)-thiazol-4-ylmethyl ester were dissolved in 5 ml 2-methoxyethanol. 10.0 mg sodium hydride were added and the mixture stirred at 50° C. for one hour. The reaction mixture was diluted by addition of 50 ml ethyl acetate, washed with brine then dried over MgSO4. The solvent was removed in vacuo and the residue purified by RP-HPLC to provide 30 mg of 2-Chloro-4-[4-(2-methoxy-ethoxymethyl)-2-(4-trifluoromethyl-phenyl)-thiazol-5-ylmethoxy]-benzonitrile as lyophilisate.

C22H18ClF3N2O3S (482.91), MS (ESI): 483.1 (M+H).

3-{2-Chloro-4-[4-(2-methoxy-ethoxymethyl)-2-(4-trifluoromethyl-phenyl)-thiazol-5-ylmethoxy]-phenyl}-4H-[1,2,4]oxadiazol-5-one

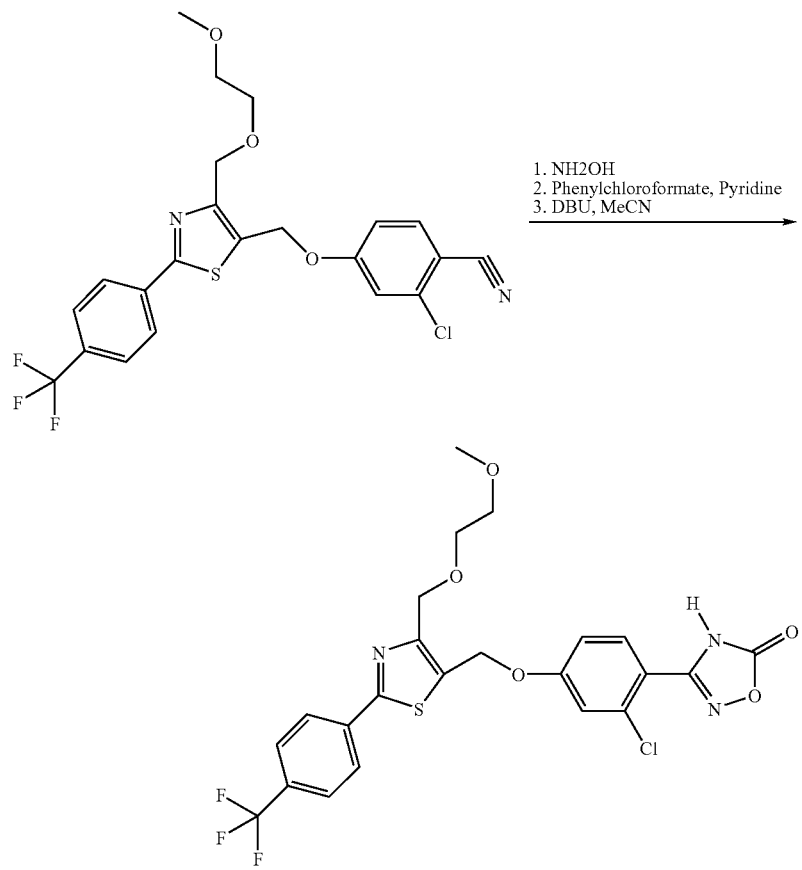

example 34

According to the method described in Example 1, 3-{2-Chloro-4-[4-(2-methoxy-ethoxymethyl)-2-(4-trifluoromethyl-phenyl)-thiazol-5-ylmethoxy]-phenyl}-4H-[1,2,4]oxadiazol-5-one was obtained from 2-Chloro-4-[4-(2-methoxy-ethoxymethyl)-2-(4-trifluoromethyl-phenyl)-thiazol-5-ylmethoxy]-benzonitrile.

C23H19ClF3N3O5S (541.94), MS (ESI): 542.2 (M+H⁺).

Example 35

3-{2-Chloro-4-[4-(2-ethoxy-ethoxymethyl)-2-(4-trifluoromethyl-phenyl)-thiazol-5-ylmethoxy]-phenyl}-4H-[1,2,4]oxadiazol-5-one

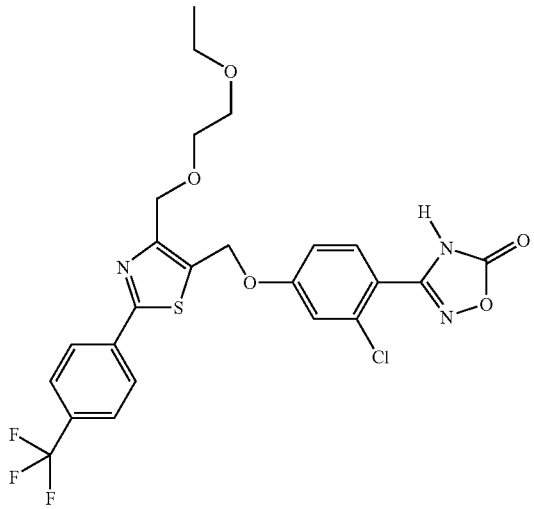

According to the method described in Example 1 and 34, 3-{2-Chloro-4-[4-(2-ethoxy-ethoxymethyl)-2-(4-trifluoromethyl-phenyl)-thiazol-5-ylmethoxy]-phenyl}-4H-[1,2,4]oxadiazol-5-one was obtained from methanesulfonic acid 5-(3-chloro-4-cyano-phenoxymethyl)-2-(4-trifluoromethyl-phenyl)-thiazol-4-ylmethyl ester and 2-ethoxy-ethanol.

C24H21ClF3N3O5S (555.96), MS (ESI): 556.3 (M+H⁺).

Example 36

3-{2-Chloro-4-[4-(3-methoxy-propoxymethyl)-2-(4-trifluoromethyl-phenyl)-thiazol-5-ylmethoxy]-phenyl}-4H-[1,2,4]oxadiazol-5-one

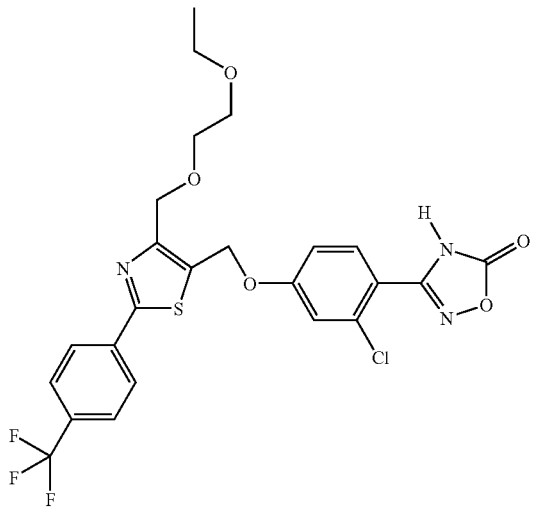

According to the method described in Example 1 and 34, 3-{2-Chloro-4-[4-(3-methoxy-propoxymethyl)-2-(4-trifluoromethyl-phenyl)-thiazol-5-ylmethoxy]-phenyl}-4H-[1,2,4]oxadiazol-5-one was obtained from methanesulfonic acid 5-(3-chloro-4-cyano-phenoxymethyl)-2-(4-trifluoromethyl-phenyl)-thiazol-4-ylmethyl ester and 3-methoxy-1-propanol.

C24H21ClF3N3O5S (555.96), MS (ESI): 556.3 (M+H⁺).

Example 37

3-{4-[5-Methoxymethyl-2-(4-methoxy-phenyl)-oxazol-4-ylmethoxy]-2-methyl-phenyl}-4H-[1,2,4]oxadiazol-5-one

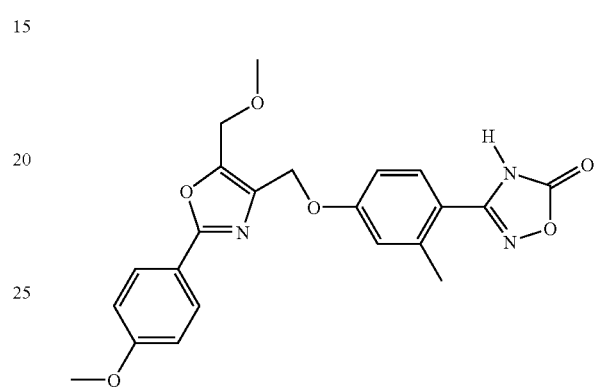

According to the method described in example 15 and example 33, 3-{4-[5-Methoxymethyl-2-(4-methoxy-phenyl)-oxazol-4-ylmethoxy]-2-methyl-phenyl}-4H-[1,2,4]oxadiazol-5-one was obtained from [2-(4-methoxy-phenyl)-5-(tetrahydro-pyran-2-yloxymethyl)-oxazol-4-yl]-methanol and commercially available 4-Fluoro-2-methylbenzonitrile.

C22H21N3O6 (423.43), MS (ESI): 424.2 (M+H⁺).

Example 38

3-{4-[5-(2-Methoxy-ethoxymethyl)-2-(4-methoxy-phenyl)-oxazol-4-ylmethoxy]-2-methyl-phenyl}-4H-[1,2,4]oxadiazol-5-one

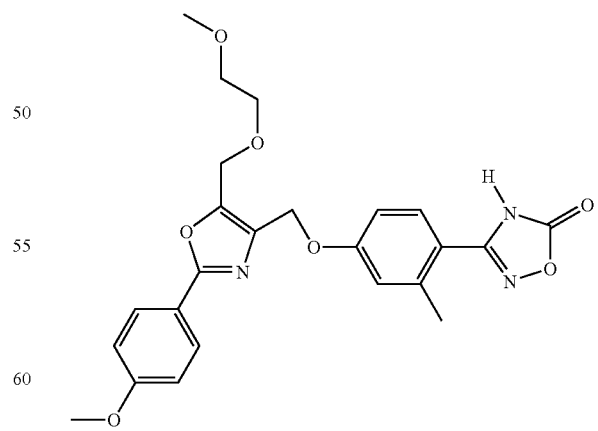

According to the method described in example 15 and example 34, 3-{4-[5-(2-methoxy-ethoxymethyl)-2-(4-methoxy-phenyl)-oxazol-4-ylmethoxy]-2-methyl-phenyl}-4H-[1,2,4]oxadiazol-5-one was obtained from [2-(4-methoxyphenyl)-5-(tetrahydro-pyran-2-yloxymethyl)-oxazol-4-yl]-methanol and commercially available 4-fluoro-2-methylbenzonitrile and 2-methoxy-ethanol.

C24H25N3O7 (467.48), MS (ESI): 468.2 (M+H+).

Example 39

3-{4-[4-Methoxymethyl-2-(4-methoxy-phenyl)-oxazol-5-ylmethoxy]-2-methyl-phenyl}-4H-[1,2,4]oxadiazol-5-one

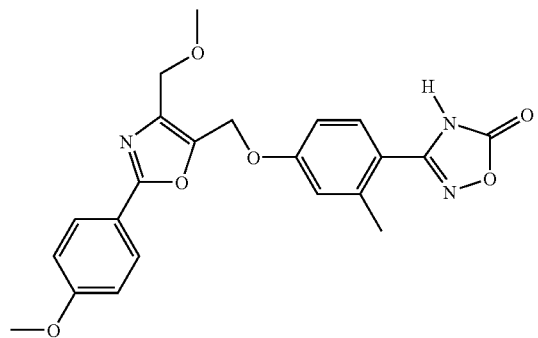

According to the method described in example 15 and example 33, 3-{4-[4-methoxymethyl-2-(4-methoxy-phenyl)-oxazol-5-ylmethoxy]-2-methyl-phenyl}-4H-[1,2,4]oxadiazol-5-one was obtained from [2-(4-methoxy-phenyl)-4-(tetrahydro-pyran-2-yloxymethyl)-oxazol-5-yl]-methanol and commercially available 4-fluoro-2-methylbenzonitrile.

C22H21N3O6 (423.43), MS (ESI): 424.2 (M+H+).

Example 40

3-{4-[4-(2-Methoxy-ethoxymethyl)-2-(4-methoxy-phenyl)-oxazol-5-ylmethoxy]-2-methyl-phenyl}-4H-[1,2,4]oxadiazol-5-one

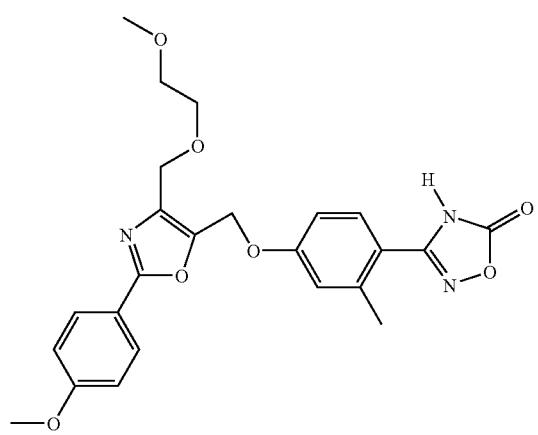

According to the method described in example 15 and example 34, 3-{4-[4-(2-methoxy-ethoxymethyl)-2-(4-methoxy-phenyl)-oxazol-5-ylmethoxy]-2-methyl-phenyl}-4H-[1,2,4]oxadiazol-5-one was obtained from [2-(4-methoxy-phenyl)-4-(tetrahydro-pyran-2-yloxymethyl)-oxazol-5-yl]-methanol and commercially available 4-fluoro-2-methylbenzonitrile and 2-methoxy-ethanol.

C24H25N3O7 (467.48), MS (ESI): 468.2 (M+H+).

Example 41

3-{4-[4-(2-Ethoxy-ethoxymethyl)-2-(4-methoxy-phenyl)-oxazol-5-ylmethoxy]-2-methyl-phenyl}-4H-[1,2,4]oxadiazol-5-one

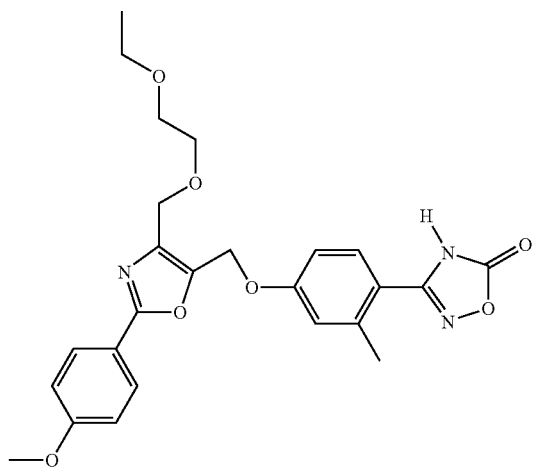

According to the method described in example 15 and example 34, 3-{4-[4-(2-ethoxy-ethoxymethyl)-2-(4-methoxy-phenyl)-oxazol-5-ylmethoxy]-2-methyl-phenyl}-4H-[1,2,4]oxadiazol-5-one was obtained from [2-(4-methoxy-phenyl)-4-(tetrahydro-pyran-2-yloxymethyl)-oxazol-5-yl]-methanol and commercially available 4-fluoro-2-methylbenzonitrile and 2-ethoxy-ethanol.

C25H27N3O7 (481.51), MS (ESI): 482.2 (M+H+).

Example 42

3-{4-[2-(4-Methoxy-phenyl)-4-(3-methoxy-propoxymethyl)-oxazol-5-ylmethoxy]-2-methyl-phenyl}-4H-[1,2,4]oxadiazol-5-one

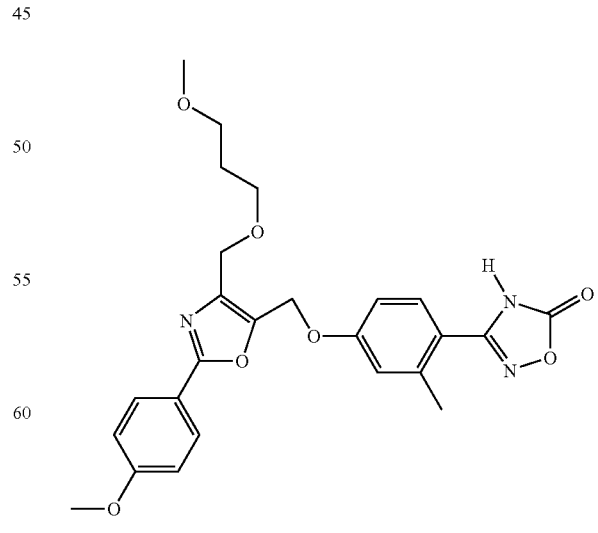

According to the method described in example 15 and example 34, 3-{4-[2-(4-methoxy-phenyl)-4-(3-methoxypropoxymethyl)-oxazol-5-ylmethoxy]-2-methyl-phenyl}-4H-[1,2,4]oxadiazol-5-one was obtained from [2-(4-methoxy-phenyl)-4-(tetrahydro-pyran-2-yloxymethyl)-oxazol-5-yl]-methanol and commercially available 4-fluoro-2-methylbenzonitrile and 3-methoxy-propan-1-ol.

C25H27N3O7 (481.51), MS (ESI): 482.2 (M+H$^+$).

Example 43

3-{4-[4-Ethoxymethyl-2-(4-methoxy-phenyl)-oxazol-5-ylmethoxy]-2-methyl-phenyl}-4H-[1,2,4]oxadiazol-5-one

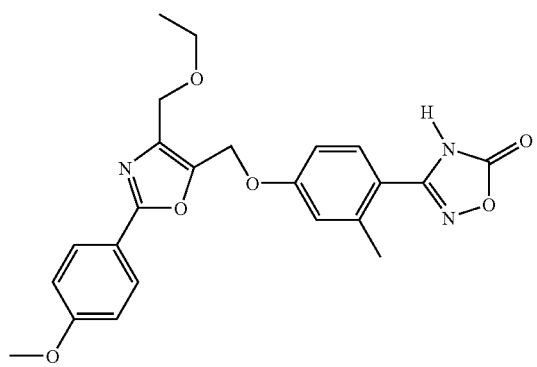

According to the method described in example 15 and example 34, 3-{4-[4-ethoxymethyl-2-(4-methoxy-phenyl)-oxazol-5-ylmethoxy]-2-methyl-phenyl}-4H-[1,2,4]oxadiazol-5-one was obtained from [2-(4-methoxy-phenyl)-4-(tetrahydro-pyran-2-yloxymethyl)-oxazol-5-yl]-methanol and commercially available 4-fluoro-2-methylbenzonitrile and ethanol.

C23H23N3O6 (437.46), MS (ESI): 438.2 (M+H$^+$).

Example 44

3-{4-[4-Benzyloxymethyl-2-(4-methoxy-phenyl)-oxazol-5-ylmethoxy]-2-methyl-phenyl}-4H-[1,2,4]oxadiazol-5-one

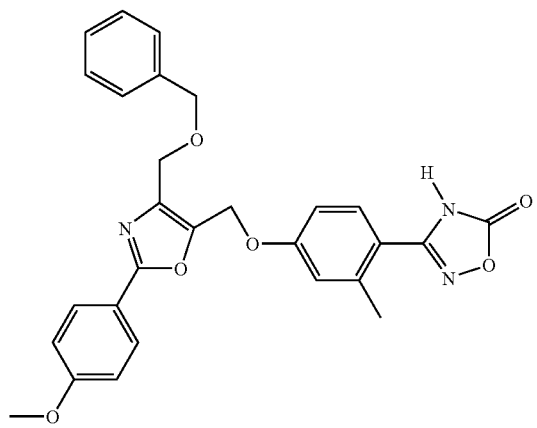

According to the method described in example 15 and example 34, 3-{4-[4-benzyloxymethyl-2-(4-methoxy-phenyl)-oxazol-5-ylmethoxy]-2-methyl-phenyl}-4H-[1,2,4]- oxadiazol-5-one was obtained from [2-(4-methoxy-phenyl)-4-(tetrahydro-pyran-2-yloxymethyl)-oxazol-5-yl]-methanol and commercially available 4-fluoro-2-methylbenzonitrile and phenyl-methanol.

C28H25N3O6 (499.53), MS (ESI): 500.2 (M+H$^+$).

Example 45

3-{2-Chloro-4-[5-methoxymethyl-2-(4-methoxy-phenyl)-oxazol-4-ylmethoxy]-phenyl}-4H-[1,2,4]oxadiazol-5-one

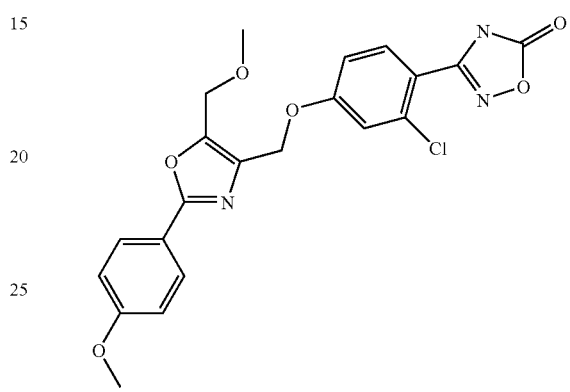

According to the method described in example 1 and example 33, 3-{2-chloro-4-[5-methoxymethyl-2-(4-methoxy-phenyl)-oxazol-4-ylmethoxy]-phenyl}-4H-[1,2,4]oxadiazol-5-one was obtained from methanesulfonic acid 2-(4-methoxy-phenyl)-5-(tetrahydro-pyran-2-yloxymethyl)-oxazol-4-ylmethyl ester and commercially available 2-chloro-4-hydroxy-benzonitrile.

C21H18ClN3O6 (443.85), MS (ES I): 444.2 (M+H$^+$).

Example 46

3-{2-Chloro-4-[5-(2-methoxy-ethoxymethyl)-2-(4-methoxy-phenyl)-oxazol-4-ylmethoxy]-phenyl}-4H-[1,2,4]oxadiazol-5-one

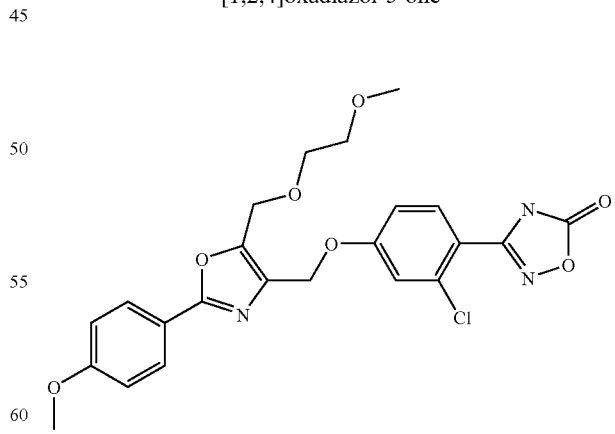

According to the method described in example 1 and example 34, 3-{2-chloro-4-[5-(2-methoxy-ethoxymethyl)-2-(4-methoxy-phenyl)-oxazol-4-ylmethoxy]-phenyl}-4H-[1,2,4]oxadiazol-5-one was obtained from methanesulfonic acid 2-(4-methoxy-phenyl)-5-(tetrahydro-pyran-2-yloxymethyl)-oxazol-4-ylmethyl ester and commercially available 2-chloro-4-hydroxy-benzonitrile and 2-methoxyethanol.

C23H22ClN3O7 (487.90), MS (ESI): 488.2 (M+H+).

Example 47

3-{2-Chloro-4-[4-methoxymethyl-2-(4-methoxy-phenyl)-oxazol-5-ylmethoxy]-phenyl}-4H-[1,2,4]oxadiazol-5-one

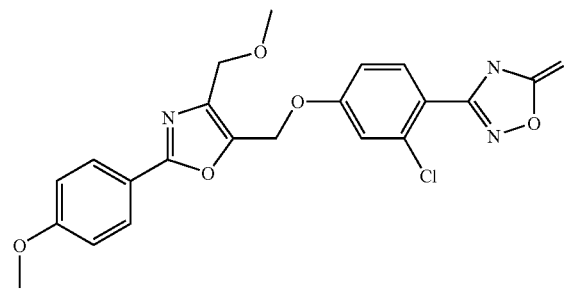

According to the method described in example 1 and example 33, 3-{2-chloro-4-[4-methoxymethyl-2-(4-methoxy-phenyl)-oxazol-5-ylmethoxy]-phenyl}-4H-[1,2,4]oxadiazol-5-one was obtained from 5-chloromethyl-2-(4-methoxy-phenyl)-4-(tetrahydro-pyran-2-yloxymethyl)-oxazole and commercially available 2-chloro-4-hydroxy-benzonitrile.

C21H18ClN3O6 (443.85), MS (ESI): 444.2 (M+H+).

Example 48

3-{2-Chloro-4-[2-(4-methoxy-phenyl)-4-(3-methoxy-propoxymethyl)-oxazol-5-ylmethoxy]-phenyl}-4H-[1,2,4]oxadiazol-5-one

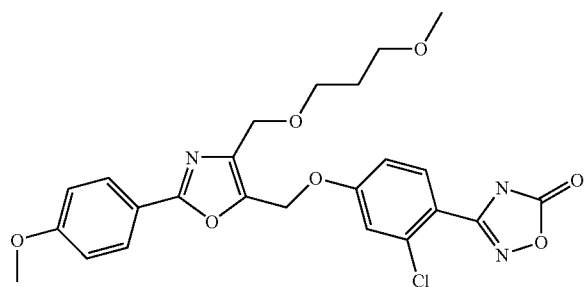

According to the method described in example 1 and example 34, 3-{2-chloro-4-[2-(4-methoxy-phenyl)-4-(3-methoxy-propoxymethyl)-oxazol-5-ylmethoxy]-phenyl}-4H-[1,2,4]oxadiazol-5-one was obtained from 5-chloromethyl-2-(4-methoxy-phenyl)-4-(tetrahydro-pyran-2-yloxymethyl)-oxazole and commercially available 2-chloro-4-hydroxy-benzonitrile and 3-methoxy-propan-1-ol.

C24H24ClN3O7 (501.93), MS (ESI): 502.2 (M+H+).

Example 49

3-{5-Bromo-2-methoxy-4-[4-methyl-2-(4-trifluoromethyl-phenyl)-thiazol-5-ylmethoxy]-phenyl}-4H-[1,2,4]oxadiazol-5-one

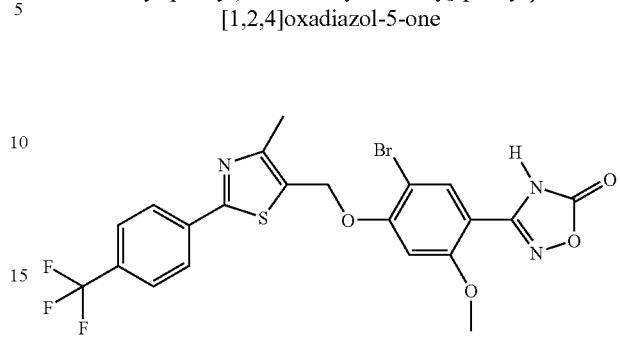

To a solution of 100 mg of 3-{2-methoxy-4-[4-methyl-2-(4-trifluoromethyl-phenyl)-thiazol-5-ylmethoxy]-phenyl}-4H-[1,2,4]oxadiazol-5-one in 1 ml of acetonitrile was added 0.08 g of N-bromosuccinimide. The resulting mixture was heated to 70° C. overnight, concentrated under reduced pressure. The crude product was purified by column chromatography on silica gel (gradient of dichloromethane/methanol from 100/0 to 94/6) and washed with 94/6 dichloromethane/methanol to give 35 mg of 3-{5-bromo-2-methoxy-4-[4-methyl-2-(4-trifluoromethyl-phenyl)-thiazol-5-ylmethoxy]-phenyl}-4H-[1,2,4]oxadiazol-5-one.

C21H15BrF3N3O4S (542.33), MS (ESI): 542.0 (M+H+).

Example 50

3-{4-[4-(3-Benzyloxy-propyl)-2-(4-trifluoromethyl-phenyl)-thiazol-5-ylmethoxy]-2-chloro-phenyl}-4H-[1,2,4]oxadiazol-5-one

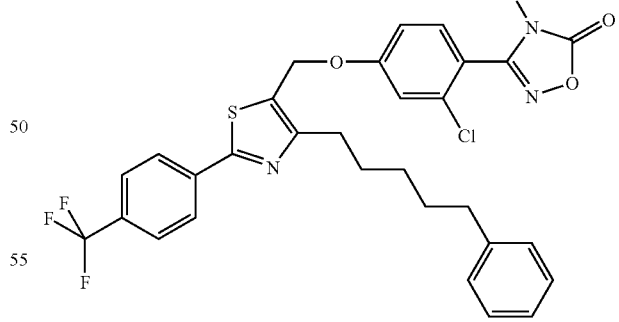

According to the method described in Example 15, 3-{4-[4-(3-benzyloxy-propyl)-2-(4-trifluoromethyl-phenyl)-thiazol-5-ylmethoxy]-2-chloro-phenyl}-4H-[1,2,4]oxadiazol-5-one was obtained from [4-(3-benzyloxy-propyl)-2-(4-trifluoromethyl-phenyl)-thiazol-5-yl]-methanol and commercially available 2-chloro-4-fluoro-benzonitrile.

C29H23ClF3N3O4S (602.03), MS (ESI): 602.2 (M+H+)

Example 51

3-[2-Chloro-4-[4-(3-hydroxy-Propyl)-2-(4-trifluoromethyl-phenyl)-thiazol-5-ylmethoxyl]-phenyl]-4H-[1,2,4]oxadiazol-5-one

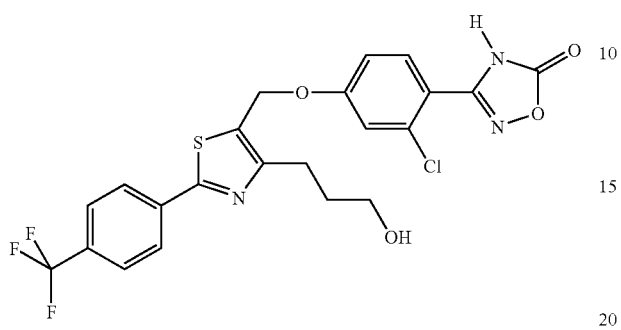

To a solution of 200 mg of 3-{4-[4-(3-benzyloxy-propyl)-2-(4-trifluoromethyl-phenyl)-thiazol-5-ylmethoxy]-2-chloro-phenyl}-4H-[1,2,4]oxadiazol-5-one in 6 ml of dichloromethane cooled to −70° C. was added 0.8 mL of a 1 M solution of boron tribromide in dichloromethane. After stirring for 45 minutes at −60° C., the solution was poured into a mixture of methanol and a saturated aqueous solution of sodium hydrogenocarbonate, filtered and concentrated under reduced pressure. The crude product was purified by column chromatography on silica gel (gradient of dichloromethane/methanol from 100/0 to 90/10) then crystallized from dichloromethane/diisopropylether to give 18 mg of 3-{2-chloro-4-[4-(3-hydroxy-propyl)-2-(4-trifluoromethyl-phenyl)-thiazol-5-ylmethoxy]-phenyl}-4H-[1,2,4]oxadiazol-5-one.

$C_{22}H_{17}ClF_3N_3O_4S$ (511.91), MS (ESI): 512.1 (M+H$^+$)

What is claimed is:

1. A compound of formula I:

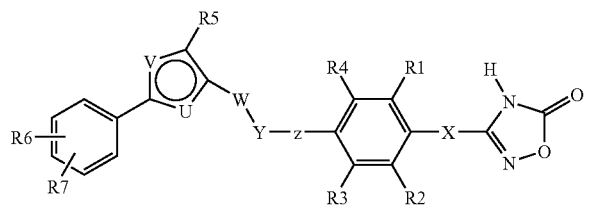

formula I wherein:

X is a bond;

$R_1$, $R_2$, $R_3$ and $R_4$ are independently selected from the group consisting of H, F, Cl, Br, $CF_3$, ($C_1$-$C_4$) alkyl, (C0-C4) alkylene-O—($C_0$-$C_4$) alkylene-H, $SCH_3$, S(O)$CH_3$, S(O)$_2$$CH_3$, CN, $OCF_3$, $OCHF_2$, and $OCH_2F$;

Z is a bond or $CH_2$;

Y is O, S, S(O) or S(O)$_2$;

W is $CH_2$ or $CH_2CH_2$;

V is N and U is selected from the group consisting of S and O, or

U is N and V is selected from the group consisting of S and O;

R5 is selected from the group consisting of (C1-C8) alkyl, (C1-C6) alkylene-O—(C0-C4) alkylene-H, (C0-C6) alkylen-phenyl, (C1-C6) alkylen-O—(C0-C4) alkylen-phenyl, (C3-C6) cycloalkyl, and (C2-C8) alkenyl, wherein the (C1-C8) alkyl or alkylene can be substituted 1-2 times by OH or O—(C1-C4) alkyl; and R6 and R7 are independently selected from the group consisting of H, F, Br, CF3, OCF3, (C1-C6) alkyl, (C0-C4) alkylen-O—(C0-C4) alkylen-H, SCF3, SF5, OCF2-CHF2, OCHF2, OCH2F, O-phenyl, phenyl, and NO2;

or a tautomer or pharmaceutically acceptable salts thereof.

2. The compound according to claim 1 wherein
$R_1$ is selected from the group consisting of H, F, Cl, Br, $CF_3$, ($C_1$-$C_4$) alkyl, O—($C_1$-$C_4$) alkyl, $SCH_3$, S(O)$CH_3$, S(O)$_2$$CH_3$, and CN;
$R_2$ is H or F;
$R_3$ is H, Br or O—($C_1$-$C_4$) alkyl;
$R_4$ is H;
$R_5$ is ($C_1$-$C_6$) alkyl or ($C_2$-$C_6$) alkenyl, wherein the ($C_1$-$C_6$) alkyl can be substituted 1-2 times by OH;
$R_6$ is in para position and is $CF_3$, $SF_5$, $OCH_3$ or phenyl; and
$R_7$ is H or F;
or a tautomer or pharmaceutically acceptable salt thereof.

3. The compound according to claim 1 in wherein:
$R_1$ is Cl or $CH_3$;
$R_2$, $R_3$ and $R_4$ are H;
Z is a bond;
Y is O;
W is $CH_2$;
V is N and U is O;
$R_5$ is ($C_1$-$C_4$) alkylene-H or ($C_1$-$C_4$) alkylene-O—($C_1$-$C_4$) alkylene-O-phenyl, wherein the alkylene can be substituted by O—(C1-C4)alkyl;
R6 is in the para-position and is $CF_3$ or —$OCH_3$; and
R7 is H;
or a tautomer or pharmaceutically acceptable salt thereof.

4. The compound according to claim 1 wherein:
R1 is $OCH_3$ or F;
$R_2$, $R_3$, and $R_4$ are H;
Z is a bond;
Y is O or S;
V is N and U is S or O;
$R_5$ is ($C_1$-$C_4$) alkyl, ($C_1$-$C_4$) alkylene-O—($C_1$-$C_4$) alkylene-H or ($C_1$-$C_4$) alkylene-O—(C1-C4) alkylene-phenyl, wherein the alkylene can be substituted by O—($C_1$-$C_4$) alkyl;
$R_6$ is in the para position and is $CF_3$ or $OCH_3$; and
$R_7$ is H;
or a tautomer or pharmaceutically acceptable salt thereof.

5. The compound according to claim 1 wherein
$R_1$ is H, F, Cl, Br, —$OCH_3$, —$SCH_3$, —$CF_3$, —$CH_3$, CN, —S(O)$CH_3$, or —S(O)$_2$$CH_3$;
$R_2$ is H or F;
$R_3$ is H, —$OCH_3$, or Br;
$R_4$ is H;
V is N and U is S;
$R_5$ is ($C_1$-$C_4$) alkylene-O—(C1-C4) alkylene-H or (C1-C4) alkylene-O—(C1-C4) alkylene-phenyl, wherein the alkylene can be substituted by O—(C1-C4) alkyl;
$R_6$ is p-$CF_3$ or p-$SF_5$; and
$R_7$ is H;
or a tautomer or pharmaceutically acceptable salt thereof.

6. The compound according to claim 1 wherein
$R_1$ is Cl, or —CH3;
$R_2$ is H;
$R_3$ is H;
$R_4$ is H;
Z is a bond;
Y is O;
W is $CH_2$;

V is N, and U is O;

$R_5$ is (C1-C4) alkyl, (C1-C4) alkylene-O—(C1-C4) alkylene-H or (C1-C4) alkylene-O—(C1-C4) alkylene-phenyl, wherein the alkylene can be substituted by O—(C1-C4) alkyl;

$R_6$ is para-OCH3 or p-phenyl, and;

$R_7$ is H;

or a tautomer or pharmaceutically acceptable salt thereof.

7. The compound according to claim 1 wherein
V is N and U is S or O;
or a tautomer or pharmaceutically acceptable salt thereof.

8. The compound according to claim 7 wherein;
U is S; and
Z is a bond;
or a tautomer or pharmaceutically acceptable salt thereof.

9. The compound according to claim 8 wherein;
$R_6$ is in the para-position;
or a tautomer or pharmaceutically acceptable salt thereof.

10. The compound according to claim 9 wherein;
$R_7$ is H or F;
or a tautomer or pharmaceutically acceptable salt thereof.

11. The compound according to claim 10 wherein;
$R_2$, $R_3$, and $R_4$ are H; and
$R_1$ is selected from the group consisting of H, F, Cl, Br, $CF_3$, $(C_1-C_4)$ alkyl, $(C_0-C_4)$ alkylene-O—$(C_0-C_4)$ alkylene-H, —$SCH_3$, $S(O)CH_3$, $S(O)_2CH_3$, and CN;
or a tautomer or pharmaceutically acceptable salt thereof.

12. The compound according to in claim 11 in which
Y is O or S;
or a tautomer or pharmaceutically acceptable salt thereof.

13. The compound according to claim 12 wherein;
W is $CH_2$;
or a tautomer or pharmaceutically acceptable salt thereof.

14. The compound according to claim 13 wherein;
$R_5$ is selected from the group consisting of $(C_1-C_4)$ alkyl and $(C_1-C_4)$ alkylene-O—$(C_0-C_4)$ alkylene-H, wherein the alkylene can be substituted by O—$(C_0-C_4)$ alkylene-H or phenyl;
or a tautomer or pharmaceutically acceptable salt thereof.

15. The compound according to claim 14 wherein
$R_1$ is F, Cl, —$CH_3$, —$OCH_3$;
or a tautomer or pharmaceutically acceptable salt thereof.

16. The compound according to claim 15 wherein
$R_5$ is $(C_1-C_4)$ alkyl;
or a tautomer or pharmaceutically acceptable salt thereof.

17. The compound according to claim 16 wherein
$R_6$ is selected from the group consisting of $CF_3$, $SF_5$, phenyl, and —OCH3;
or a tautomer or pharmaceutically acceptable salt thereof.

18. The compound according to claim 1 which is 3-{2-Chloro-4-[4-methyl-2-(4-trifluoromethyl-phenyl)-thiazole-5-ylmethoxy]-phenyl}-4H-[1,2,4]oxadiazole-5-one; or a tautomer or pharmaceutically acceptable salt thereof.

19. The compound according to claim 1 which is 3-{2-Chloro-4-[4-methyl-2-(4-pentafluorosulfanyl-phenyl)-thiazole-5-ylmethoxy]-phenyl}-4H-[1,2,4]oxadiazole-5-one; or a tautomer or pharmaceutically acceptable salt thereof.

20. The compound according to claim 1 which is 3-{4-[4-Butyl-2-(4-trifluoromethyl-phenyl)-thiazol-5-ylmethoxy]-2-chloro-benzyl}-4H-[1,2,4]oxadiazol-5-one; or a tautomer or pharmaceutically acceptable salt thereof.

21. The compound according to claim 1 which is 3-{2-Methoxy-4-[4-methyl-2-(4-trifluoromethyl-phenyl)-thiazol-5-ylmethoxy]-phenyl}-4H-[1,2,4]oxadiazol-5-one; or a tautomer or pharmaceutically acceptable salt thereof.

22. The compound according to claim 1 which is 3-{4-[4-Methyl-2-(4-trifluoromethyl-phenyl)-thiazol-5-ylmethoxymethyl]-phenyl}-4H-[1,2,4]oxadiazol-5-one; or a tautomer or pharmaceutically acceptable salt thereof.

23. The compound according to claim 1 which is 3-{2-Chloro-4-[4-(2-methoxy-ethoxymethyl)-2-(4-trifluoromethyl-phenyl)-thiazol-5-ylmethoxy]-phenyl}-4H-[1,2,4]oxadiazol-5-one; or a tautomer or pharmaceutically acceptable salt thereof.

24. The compound according to claim 1 which is 3-{5-Bromo-2-methoxy-4-[4-methyl-2-(4-trifluoromethyl-phenyl)-thiazol-5-ylmethoxy]-phenyl}-4H-[1,2,4]oxadiazol-5-one; or a tautomer or pharmaceutically acceptable salt thereof.

25. The compound according to claim 1 in wherein:
$R_1$ is Cl or $CH_3$;
$R_2$, $R_3$ and $R_4$ are H;
Z is a bond;
Y is O
W is $CH_2$;
V is S or O and U is N;
$R_5$ is $(C_1-C_4)$ alkylene-H or $(C_1-C_4)$ alkylene-O—$(C_1-C_4)$ alkylene-O-phenyl, wherein the alkylene can be substituted by O—(C1-C4)alkyl;
$R_6$ is in the para-position and is $CF_3$ or —$OCH_3$; and
R7 is H;
or a tautomer or pharmaceutically acceptable salt thereof.

26. The compound according to claim 1 wherein
V is O and U is N;
or a tautomer or pharmaceutically acceptable salt thereof.

27. The compound according to claim 26 wherein
Z is a bond;
or a tautomer or pharmaceutically acceptable salt thereof.

28. A pharmaceutical composition comprising at least one compound according to claim 1 or a tautomer or pharmaceutically acceptable salt thereof, in combination with a pharmaceutically acceptable carrier or excipient.

29. The pharmaceutical composition according to claim 28, further comprising at least one anti-diabetic, wherein the anti-diabetic is for the treatment of metabolic disorder.

30. A pharmaceutical composition comprising at least one compound according to claim 5 or a tautomer or pharmaceutically acceptable salt thereof, at least one anti-diabetic, and a pharmaceutically acceptable carrier or excipient, wherein the anti-diabetic is for the treatment of metabolic disorder.

31. The pharmaceutical composition according to claim 28, further comprising at least one lipid modulators, wherein the lipid modulator is for the treatment of fatty acid metabolism or glucose utilization disorder.

32. A method for treating diabetes mellitus or dyslipidemia a in a patient in need thereof, comprising administering to the patient a pharmaceutically effective amount of the compound according to claim 1, or a tautomer or pharmaceutically acceptable salt thereof.

* * * * *